United States Patent
Hutchinson et al.

(10) Patent No.: US 6,391,583 B1
(45) Date of Patent: May 21, 2002

(54) METHOD OF PRODUCING ANTIHYPERCHOLESTEROLEMIC AGENTS

(75) Inventors: Charles R. Hutchinson, Cross Plains; Jonathan Kennedy, Madison, both of WI (US); Cheonseok Park, Seol (KR)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/215,694

(22) Filed: Dec. 18, 1998

(51) Int. Cl.$^7$ ............................................. C12P 21/06
(52) U.S. Cl. ................... 435/69.1; 435/125; 435/6; 530/350; 536/23.1
(58) Field of Search .................. 530/350; 435/125, 435/6, 69.1; 536/23.1

(56) References Cited

U.S. PATENT DOCUMENTS

| | | | |
|---|---|---|---|
| 4,231,938 A | 11/1980 | Monaghan et al. | 260/343.5 |
| 4,282,155 A | 8/1981 | Smith et al. | 260/343.5 |
| 4,323,648 A | 4/1982 | Tanzawa et al. | 435/125 |
| 4,342,767 A | 8/1982 | Albers-Schonberg et al. | 424/250 |
| 4,346,227 A | 8/1982 | Terahara et al. | 560/119 |
| 4,444,784 A | 4/1984 | Hoffman et al. | 424/279 |
| 5,030,447 A | 7/1991 | Joshi et al. | 424/80 |
| 5,151,365 A | 9/1992 | Dombrowski et al. | 435/254 |
| 5,159,104 A | 10/1992 | Dabora et al. | 560/119 |
| 5,180,589 A | 1/1993 | Joshi et al. | 424/465 |
| 5,182,298 A | 1/1993 | Helms et al. | 514/455 |
| 5,198,345 A | 3/1993 | Gwynne et al. | 455/69.1 |
| 5,252,474 A | 10/1993 | Gewain et al. | 435/172.3 |
| 5,362,638 A | 11/1994 | Dahiya | 435/125 |
| 5,744,350 A | 4/1998 | Vinci et al. | 435/254.11 |

FOREIGN PATENT DOCUMENTS

| | | | |
|---|---|---|---|
| EP | 0 556 699 A1 | | 8/1993 |
| WO | WO 95/12661 | * | 5/1995 |
| WO | WO 97 00962 A | | 1/1997 |
| WO | WO 98 48019 A | | 10/1998 |

OTHER PUBLICATIONS

J.T. Kealey, et al., "Production of a Polyketide Natural product in Nonpolyketide–producing Prokaryotic and Eukaryotic Hosts," *Proc. Natl. Acad. Sci. USA* 95:505–509, 1998.

J. Kennedy, et al., "Modulation of Polyketide Synthase Activity by Accessory Proteins During Lovastatin Biosynthesis," *Science* 284:1368–1372, 1999.

M. Manzoni, et al., "Production and Purification of Statins from *Aspergillus terreus* Strains," *Biotechnol. Tech.* 12(7):529–532, 1998.

Vinci et al., Journal of Industrial Microbiology, vol. 8, No. 2, pp. 113–119, 1991.*

Alignment: Vinci et al., Acession No. Q92323, 1995.*

Murphy, et al., "Hypothetical 59.3 KDA Protein C17C9.16C in Chromosome I from *Schizosaccharomyces pombe*" 1996 (Database).

Oliver, et al., "Putative Tricarboxylate Transport Protein C19G12.05 from Fission Yeast," 1998 (Database).

Van Peij, et al., "Beta–xylosidase, xlnD Gene from *Aspergillus nidulans*," 1997 (Database).

* cited by examiner

*Primary Examiner*—Karen Cochrane Carlson
*Assistant Examiner*—Hope A. Robinson
(74) *Attorney, Agent, or Firm*—Quarles & Brady LLP

(57) ABSTRACT

A method of increasing the production of lovastatin or monacolin J in a lovastatin-producing or non-lovastatin-producing organism is disclosed. In one embodiment, the method comprises the steps of transforming an organism with the *A. terreus* D4B segment, wherein the segment is translated and where an increase in lovastatin production occurs.

19 Claims, 6 Drawing Sheets

METHOD OF PRODUCING ANTIHYPERCHOLESTEROLEMIC AGENTS

STATEMENT REGARDING FEDERALLY SPONSORED RESEARCH AND DEVELOPMENT

This invention was made with United States government support awarded by the following agencies: NIH Grant No: AI43031. The United States has certain rights in this invention.

CROSS-REFERENCES TO RELATED APPLICATION

Not applicable.

BACKGROUND OF THE INVENTION

Cholesterol and other lipids are transported in body fluids by low-density lipoproteins (LDL) and high-density lipoproteins (HDL). Substances that effectuate mechanisms for lowering LDL-cholesterol may serve as effective antihypercholesterolemic agents because LDL levels are positively correlated with the risk of coronary artery disease.

MEVACOR (lovastatin; mevinolin) and ZOCOR (simvastatin) are members of a group of active antihypercholesterolemic agents that function by inhibiting the rate-limiting step in cellular cholesterol biosynthesis, namely the conversion of hydroxymethylglutarylcoenzyme A (HMG-CoA) into mevalonate by HMG-CoA reductase.

The general biosynthetic pathway of a naturally occurring HMG-CoA reductase inhibitor has been outlined by Moore, et al., who showed that the biosynthesis of mevinolin (lovastatin) by Aspergillus terreus ATCC 20542 begins with acetate and proceeds via a polyketide pathway (R. N. Moore, et al., *J. Amer. Chem. Soc.* 107:3694–3701, 1985). Endo, et al. described similar biosynthetic pathways in *Pencillium citrinum* NRRL 8082 and *Monascus ruber* M-4681 (A. Y. Endo, et al., *J. Antibiot.* 38:444–448, 1985).

The recent commercial introduction of microbial HMG-CoA reductase inhibitors has fostered a need for high yielding production processes. Methods of improving process yield have included scaling up the process, improving the culture medium and simplifying the isolation.

Previous attempts to increase the biosynthesis of HMG-CoA reductase inhibitors at the level of gene expression have focused on increasing the concentration triol polyketide synthase (TPKS), a multifunctional protein with at least six activities as evidenced by the product of the enzymatic activity (Moore, supra, 1985). TPKS is believed to be the rate-limiting enzymatic activity(ies) in the biosynthesis of the HMG-CoA reductase inhibitor compounds.

U.S. Pat. No. 5,744,350 identifies a DNA encoding triol polyketide synthase (TPKS) from *Aspergillus terreus*. "NPKS" is now preferred to TPKS as the acronym for "nonaketide polyketide synthase."

SUMMARY OF THE INVENTION

In one embodiment, the present invention is a method of increasing the production of lovastatin in a lovastatin-producing organism. The method comprises the steps of transforming the organism with a nucleic acid sequence comprising the D4B segment, preferably comprising nucleotides 579–33,000 of SEQ ID NO:18 and 1–5,349 of SEQ ID NO:19. The nucleic acid sequence is transcribed and translated and an increase in lovastatin production occurs. Preferably, this increase is at least 2-fold.

In a preferred form of the present invention, the lovastatin-producing organism is selected from the group consisting *A. terreus* ATCC 20542 and ATCC 20541.

In another embodiment, the method comprises the step of transforming the organism with the corresponding D4B segment isolated from a non-*A. terreus* lovastatin-producing organism.

In another embodiment, the present invention is a method of increasing the production of lovastatin in a lovastatin-producing organism, comprising the step of transforming the organism with the LovE gene, wherein the nucleic acid sequence is transcribed and translated and wherein an increase in lovastatin production occurs.

In another embodiment of the present invention, one may increase the production of monacolin J in a non-lovastatin-producing organism comprising the steps of transforming the organism with a nucleic acid sequence comprising the D4B segment. As a further step, one may additionally transform the organism with an entire LovF gene. If the entire LovF gene is added to the D4B segment, the organism will produce lovastatin.

In another embodiment, the present invention is the lovastatin production gene cluster, preferably SEQ ID NOs:18 and 19, and the individual genes comprising that cluster.

It is an object of the present invention to provide a method for increasing lovastatin and monacolin J production in both lovastatin-producing and non-lovastatin producing organisms.

Other objects, features and advantages of the present invention will become apparent after review of the specification, claims and drawings.

DESCRIPTION OF THE INVENTION

In General

Figure 1:
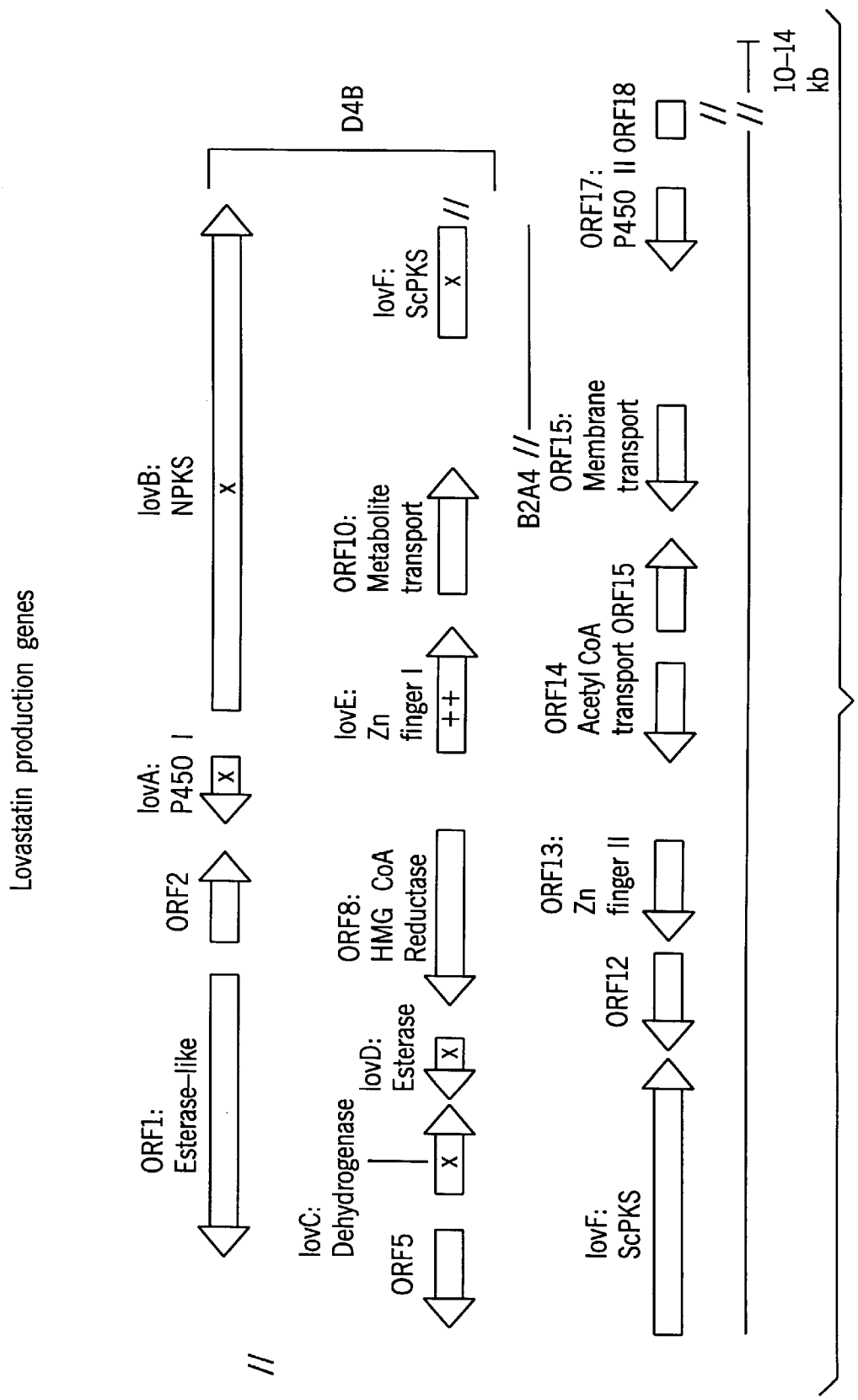
FIG. 1 is a diagram of lovastatin production genes.

The Examples below disclose the cloning and sequencing of a cluster of 17 genes from *A. terreus* ATCC 20542, a strain that natively produces lovastatin (See FIG. 1). These genes flank the NPKS gene, which is known to be required for lovastatin production (see, for example, U.S. Pat. No. 5,744,350).

The DNA sequence of the cluster has been determined and is disclosed below at SEQ ID NOs:18 and 19. Mutations in four of the genes (P450I/LovA, SEQ ID NO:22; dehydrogenase/LovC, SEQ ID NO:24; esterase/LovD, SEQ ID NO:25; and ScPKS/LovF, SEQ ID NO:29) have been isolated and demonstrate that each of these four individual genes is required for lovastatin production. These genes are indicated with an X symbol in FIG. 1 and referred to herein as the "*A. terreus* lovastatin gene cluster."

Another of the genes (Zn Finger I/LovE, SEQ ID NO:27) is thought to regulate the transcription of the other genes and causes a notable increase in lovastatin production when reintroduced into *A. terreus* ATCC 20542.

Applicants have used the following convention in naming the genes and proteins of the present invention. The genes and proteins are first named with either an "ORF" or "Lov" prefix and then named either numerically or alphabetically. "Lov" signifies genes shown to be essential for lovastatin production. Applicants have also included a descriptor name that describes a probable function of the protein. For example, SEQ ID NO:1 is described as the "ORF1/esterase-like protein" because Applicants have compared the amino acid sequence to known esterases.

The portion of the gene cluster between ORF1/esterase-like protein and the mid-region of LovF/SCPKS is referred to as the "D4B segment". The *A. terreus* D4B segment is contained within a plasmid clone deposited as ATCC 98876. As described below, other lovastatin-producing organisms contain an analogous D4B segment comprising analogous genes. The present invention comprises a "D4B segment" isolated from other lovastatin-producing organisms. The arrangement of the genes within the D4B segment may be different in other organisms. We predict that the genes within these other segments will have at least 80% homology, at the nucleic acid level, with the genes disclosed herein. We envision that each of these lovastatin-producing organisms will comprise within their genomes a LovA, LovB, LovC, LovD, LovE and LovF gene.

We have determined that the D4B segment will confer production of monocolin J if the genes are all expressed, as we show below in an example using *A. nidulans*. We envision that adding the LovF gene to the D4B segment genes will result in the production of lovastatin in a non-lovastatin-producing organism.

Table 1, below, summarizes information regarding the different protein and nucleic acid sequences of the present invention. SEQ ID NOs:1–17 are predicted translation products of various members of the gene cluster. SEQ ID NOs:18 and 19 are the entire DNA sequence of the gene cluster. SEQ ID NOs:21–36 are the genomic DNA sequences of the various members of the gene cluster and include the introns. These DNA sequences are reported in the Sequence Listing in the 5'-3' orientation, although, as FIG. 1 indicates, some of these DNA sequences are in the inverted orientation in the actual cluster.

TABLE 1

| SEQ ID NO. | DESCRIPTION | COMMENTS |
|---|---|---|
| SEQ ID NO: 1 | Predicted amino acid sequence of ORF1/Esterase-like protein | Translation of 6 EXONS 6865–6568, 6462–5584, 5520–4822, 4774–3511, 3332–2372, 2301–1813 (reverse complement) FROM SEQ ID NO: 18 |
| SEQ ID NO: 2 | Predicted amino acid sequence of ORF2 | Translation of 1 EXON 7616–8602 FROM SEQ ID NO: 18 |
| SEQ ID NO: 3 | Predicted amino acid sequence of LovA/P4501 protein | Translation of 1 EXON 10951–9980 (reverse complement) FROM SEQ ID NO: 18 |
| SEQ ID NO: 4 | Predicted amino acid sequence of ORF5 | Translation of 1 EXON 22760–21990 (reverse complement) FROM SEQ ID NO: 18 |
| SEQ ID NO: 5 | Predicted amino acid sequence of LovC/Dehydrogenase | Translation of 3 EXONS 23158–23717, 23801–23912, 23991–24410 FROM SEQ ID NO: 18 |
| SEQ ID NO: 6 | Predicted amino acid sequence of LovD/Esterase | Translation of 3 EXONS 26203–26080, 26005–25017, 24938–24810 (reverse complement) FROM SEQ ID NO: 18 |
| SEQ ID NO: 7 | Predicted amino acid sequence of ORF8/HMG CoA Reductase | Translation of 5 EXONS 30062–29882, 29803–29745, 29664–27119, 27035–26779, 26722–26559 (reverse complement) FROM SEQ ID NO: 18 |
| SEQ ID NO: 8 | Predicted amino acid sequence of LovE/Zn Finger I | Translation of 1 EXON 31360–32871 FROM SEQ ID NO: 18 |
| SEQ ID NO: 9 | Predicted amino acid sequence of ORF10/Metabolite transport | Translation of 8 EXONS 1400–1452, 1619–1695, 1770–1996, 2065–2088, 2154–2225, 2332–2865, 2939–3099, 3180–3560 FROM SEQ ID NO: 19 |
| SEQ ID NO: 10 | Predicted amino acid sequence of LovF/ScPKS | Translation of 7 EXONS 4430–4627, 4709–4795, 4870–4927, 4985–5318, 5405–5912, 5986–6565, 6631–12464 FROM SEQ ID NO: 19 |
| SEQ ID NO: 11 | Predicted amino acid sequence of ORF12 | Translation of 3 EXONS 13596–13496, 13451–13063, 12968–12709 (reverse complement) FROM SEQ ID NO: 19 |
| SEQ ID NO: 12 | Predicted amino acid sequence of ORF13/Zn Finger II | Translation of 5 EXONS 16608–16463, 16376–15572, 15519–15346, 15291–14825, 14767–14131 (reverse complement) FROM SEQ ID NO: 19 |
| SEQ ID NO: 13 | Predicted amino acid sequence of ORF14/Acetyl CoA transport protein | Translation of 7 EXONS 19642–19571, 19502–19427, 19352–19227, 19158–19011, 18956–18663, 18587– |

TABLE 1-continued

| SEQ ID NO. | DESCRIPTION | COMMENTS |
|---|---|---|
| | | 18438, 18380–18341 (reverse complement) FROM SEQ ID NO: 19 |
| SEQ ID NO: 14 | Predicted amino acid sequence of ORF15 | Translation of 2 EXONS 20332–20574, 20631–21860 FROM SEQ ID NO: 19 |
| SEQ ID NO: 15 | Predicted amino acid sequence of ORF16/Membrane transport protein | Translation of 5 EXONS 24521–24054, 23996–23936, 23876–23184, 23111–22977, 22924–22818 (reverse complement) FROM SEQ ID NO: 19 |
| SEQ ID NO: 16 | Predicted amino acid sequence of ORF17/P450II protein | Translation of 3 EXONS 28525–27673, 27606–27284, 27211–26837 (reverse complement) FROM SEQ ID NO: 19 |
| SEQ ID NO: 17 | Predicted amino acid sequence of ORF18 (incomplete) | Translation of 2 EXONS 29826–30995, 31054–31328 (incomplete) FROM SEQ ID NO: 19 |
| SEQ ID NO: 18 | DNA sequence of gene cluster-first 33,000 nucleotides | |
| SEQ ID NO: 19 | DNA sequence of cluster-nucleotides 33,001–64,328 (renumbered 1–31, 328) | |
| SEQ ID NO: 20 | DNA sequence of ORF1/Esterase-like gene | Start = 6865 Stop = 1813 SEQ ID NO: 18 |
| SEQ ID NO: 21 | DNA sequence of ORF2 | Start = 7616 Stop = 8602 SEQ ID NO: 18 |
| SEQ ID NO: 22 | DNA sequence of LovA/P450I gene | Start = 10951 Stop = 9980 SEQ ID NO: 18 |
| SEQ ID NO: 23 | DNA sequence of ORF5 | Start = 22760 Stop = 21990 SEQ ID NO: 18 |
| SEQ ID NO: 24 | DNA sequence of LovC/Dehydrogenese | Start = 23158 Stop = 24410 SEQ ID NO: 18 |
| SEQ ID NO: 25 | DNA sequence of LovD/Esterase | Start = 24810 Stop = 26203 SEQ ID NO: 18 |
| SEQ ID NO: 26 | DNA sequence of ORF8/HMG CoA Reductase | Start = 30062 Stop = 26559 SEQ ID NO: 18 |
| SEQ ID NO: 27 | DNA sequence of LovE/Zn Finger I | Start = 31360 Stop = 32871 SEQ ID NO: 18 |
| SEQ ID NO: 28 | DNA sequence of ORF10/Metabolite transport | Start = 1400 Stop = 3560 SEQ ID NO: 19 |
| SEQ ID NO: 29 | DNA sequence of LovF/ScPKS | Start = 4430 Stop = 12464 SEQ ID NO: 19 |
| SEQ ID NO: 30 | DNA sequence of ORF12 | Start = 13596 Stop = 12709 SEQ ID NO: 19 |
| SEQ ID NO: 31 | DNA sequence of ORF13/Zn Finger II | Start = 16608 Stop = 14131 SEQ ID NO: 19 |
| SEQ ID NO: 32 | DNA sequence of ORF14/Acetyl CoA transport gene | Start = 19642 Stop = 18341 SEQ ID NO: 19 |
| SEQ ID NO: 33 | DNA sequence of ORF15 | Start = 20332 Stop = 21860 SEQ ID NO: 19 |
| SEQ ID NO: 34 | DNA sequence of ORF16/Membrane transport protein | Start = 24521 Stop = 22818 SEQ ID NO: 19 |
| SEQ ID NO: 35 | DNA sequence of ORF17/P450II gene | Start = 28525 Stop = 26837 SEQ ID NO: 19 |
| SEQ ID NO: 36 | DNA sequence of ORF18 (incomplete) | Start = 29826 to 31328 (incomplete) SEQ ID NO: 19 |

Table 1 also notes the translation start and stop points in the various gene sequences.

The sequence of the NPKS gene is not listed in SEQ ID NOs:21–36. This gene is characterized in U.S. Pat. No. 5,744,350. However, SEQ ID NOs:18 and 19 do contain the sequence of the NPKS gene within the context of the entire gene cluster.

To perform many embodiments of the present invention, one will need to recreate various genes or a portion of the gene cluster described herein. Applicants have provided sequence data in the Sequence Listing sufficient to allow one of skill in the art to construct numerous probes suitable to recreate the genes from an *A. terreus* genomic library. Applicants have also described below various methods for isolating *A. terreus* DNA.

Figure 4:
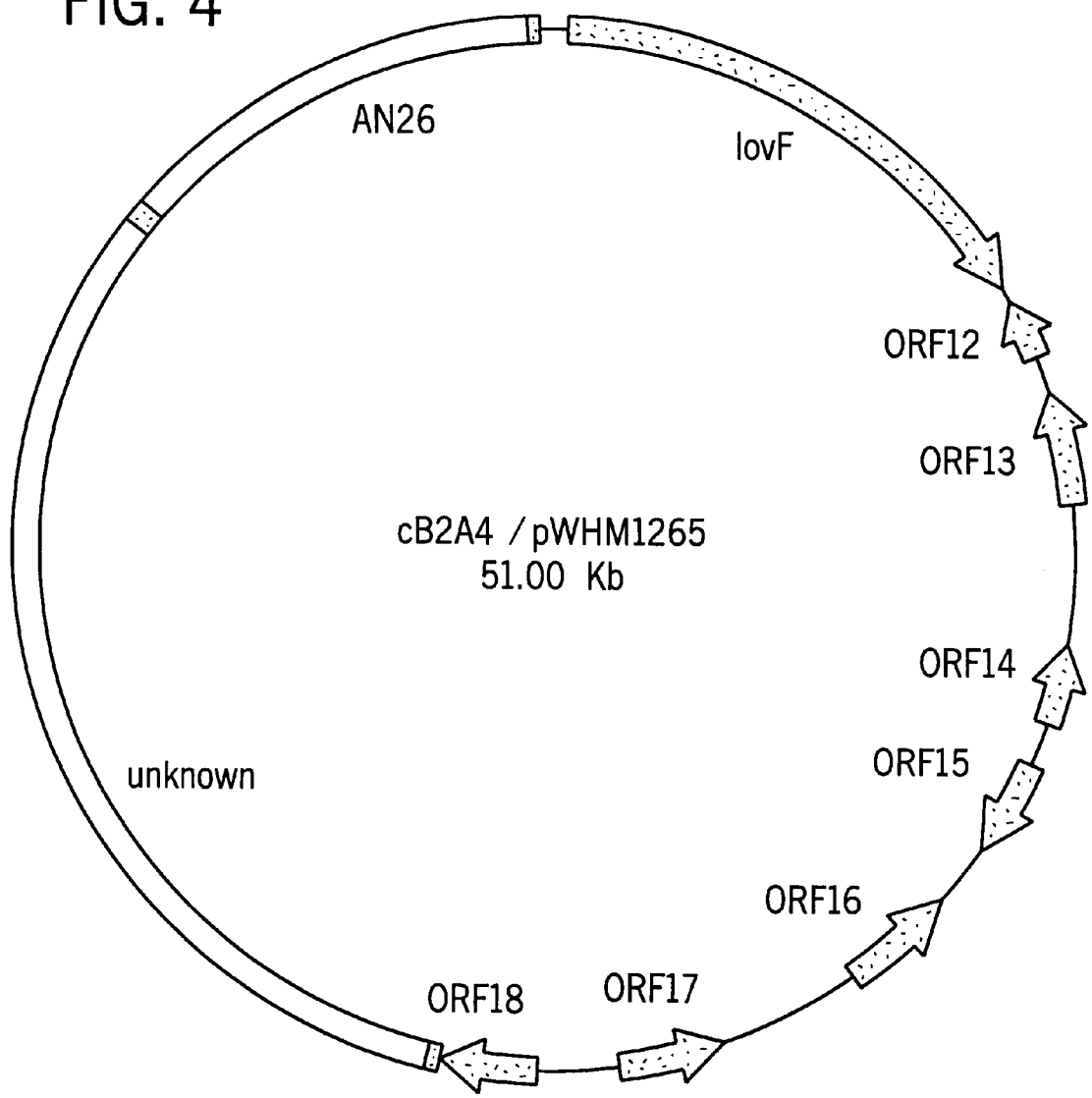
FIG. 4 is a schematic drawing of plasmid pWHM1264/CB24A.

Additionally, Applicants have deposited ATCC Accession No. ATCC 98876, which contains clone pWHM1263 (cD4B) and ATCC Accession No. ATCC 98877 which contains clone pWHM1265 (CB2A4). Both plasmids are described in more detail below. FIG. 4 describes clone CB2A4/pWHM1265, and FIG. 6 describes clone CB4B/pWHM1263. FIG. 1 also indicates the boundaries of the D4B and B2A4 clones.

The clones and their inserts may be prepared from the ATCC deposits by methods known to those of skill in the art. The DNA from the clones may be isolated and any gene within the gene cluster may be isolated and utilized.

Increasing the Production of Lovastatin by Lovastatin-producing Fungi and Yeast

In one embodiment, the present invention is a method of increasing the production of lovastatin in a lovastatin-producing fungi and yeast, preferably *A. terreus* ATCC20542 and ATCC20541. Other examples of suitable lovastatin-producing fungi and yeast are listed in Table 2, below.

TABLE 2

Microorganisms other than *A. terreus* reported to produce lovastatin (mevinolin)

Monascus (17 of 124 strains screened) species[1]
    *M. ruber*
    *M. purpureus*
    *M. pilosus*
    *M. vitreus*
    *M. pubigerus*
*Penicillium sp.*[1]
*Hypomyces sp.*
*Doratomyces sp.*
*Phoma sp.*
*Eupenicillium sp.*
*Gymnoascus sp.*
*Trichoderma sp.*
*Pichia labacensis*[2]
*Candida cariosilognicola*
*Aspergilus oryzea*[3]
*Doratomyces stemonitis*
*Paecilomyces virioti*
*Penicillum citrinum*
*Penicillin chrysogenum*
*Scopulariopsis brevicaulis*
*Trichoderma viride*

[1]. P. Juzlova, L. Martinkova, V. Kren. Secondary Metabolites of the fungus Monascus: a review. J. Ind. Microbiol. 16:163–170 and references cited therein (1996).
[2]. N. Gunde-Cimerman, A. Plemenitas and A. Cimerman. A hydroxymethylglutaryl-CoA reductase inhibitor synthesized by yeasts. FEMS Microbiol. Lett. 132:39–43 (1995).
[3]. A. A. Shindia. Mevinolin production by same fungi. Folio Microbiol. 42:477–480 (1997).

By "increasing the production" we mean that the amount of lovastatin produced is increased by at least 2-fold, preferably by at least 5-fold. The examples below demonstrate two preferred methods for analyzing strains for lovastatin production. In method A, the spore suspension is inoculated into a flask of SEED medium and grown. The resulting seed culture is used to inoculate FM media and grown for six days. In fermentation method B, one inoculates 50 ml of RPM media and grows this larger culture for 7 days.

Both cultures are extracted, pH adjusted, mixed with ethyl acetate and shaken for two hours. For analysis, 1 ml of the ethyl acetate layer is dried under a nitrogen stream and resuspended in methanol. For TLC analysis, a small amount of the extract is run on C18 reverse phase TLC plates in a solvent system of methanol; 0.1% phosphoric acid. The TLC plates are developed by spraying with phosphomolybdic acid in methanol and heating with a heat gun. The extracts are compared with authentic lovastatin, monacolin J. monacolin L and dihydromonocolon L.

If one wishes HPLC analysis, the examples below describe the use of a Waters Nova-Pak C18 column used with a solvent system of acetonitrile and phosphoric acid. A Waters 996 Photodiode Array Detector will detect the metabolites. Lovastatin was detected at 238 nm.

In one embodiment, one would transform a lovastatin-producing fungi or yeast with the lovE/zinc finger I gene, preferably comprising the nucleotides of SEQ ID NO:27. The examples below predict that this will result in an increase of at least 5–7 fold. Preferably, the increase will be at least 2.0-fold.

One may also transform a lovastatin-producing fungi or yeast with the LovE gene isolated from other lovastatin-producing fungi or yeast. One may obtain this gene by use of a probe derived from SEQ ID NO:27 by methods known to those of skill in the art.

One may also transform lovastatin-producing fungi and yeast with the D4B segment of the lovastatin production gene cluster (see FIG. 1), preferably as found in ATCC accession number 98876. Alternatively, one may transform lovastatin-producing fungi or yeast with the entire gene cluster, as diagramed in FIG. 1.

We envision that to successfully increase lovastatin production, one may also wish to transform less than the entire gene cluster. Preferably, one may determine what the smallest possible segment is by deleting various portions of the gene cluster and determining whether lovastatin production is continually increased. Similarly, if one begins with the D4B segment, one may delete various portions for the segment and determine whether lovastatin production is continually increased by at least 2-fold.

Figure 3:
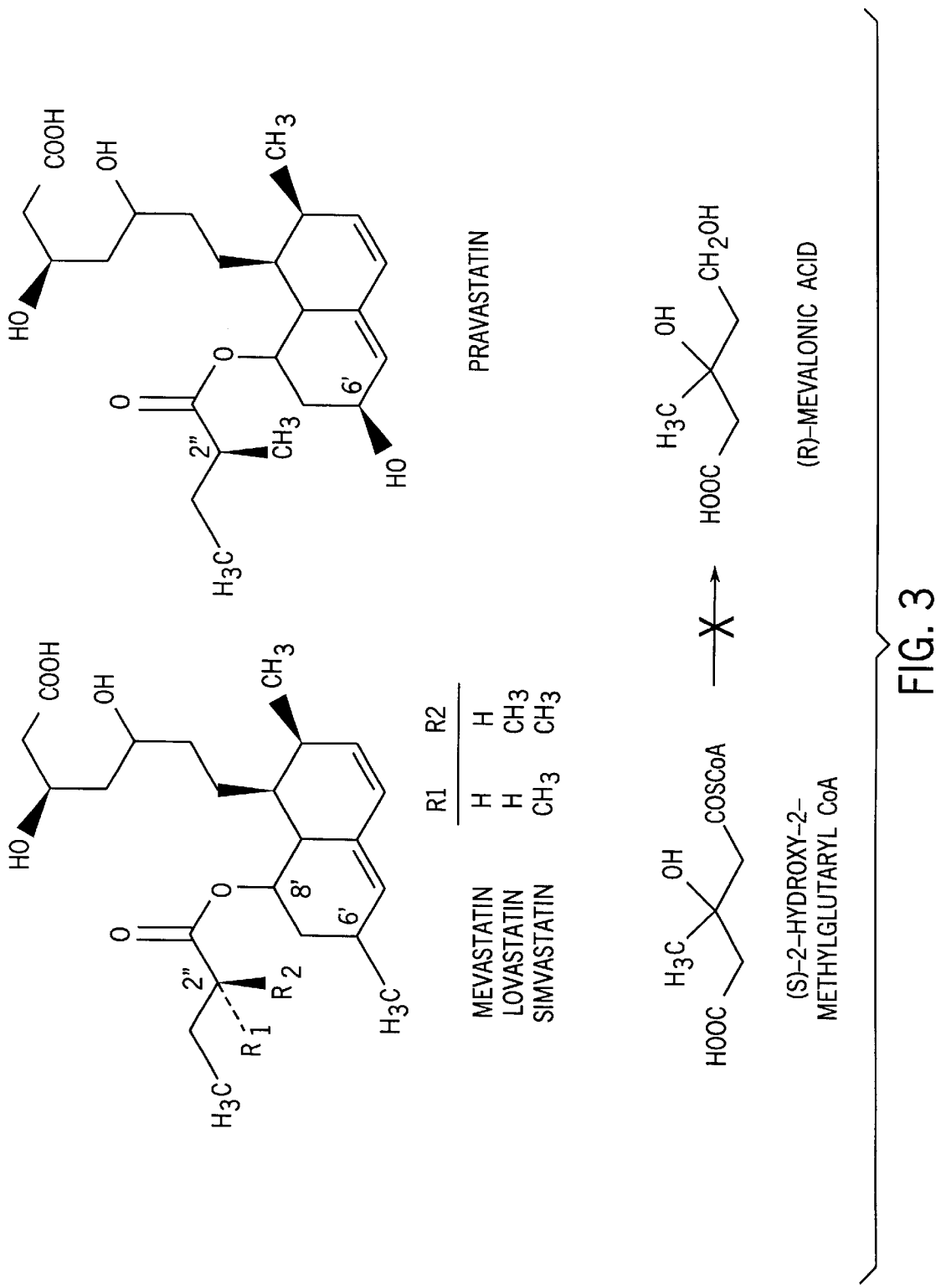
FIG. 3 is a comparative diagram of statins.

Modification of the LovB/NPKS gene would produce other HMG CoA inhibitors. For example, FIG. 3 diagrams the relationship between mevastatin, lovastatin, simvastatin and pravastatin. In one example, the methyl transferase domain of the NPKS gene may be replaced with an inactive form to make pravastatin. The HMG-CoA reductase inhibitors within this invention include, but are not limited to, compactin (ML-236B), lovastatin, simvastatin, pravastatin and mevastatin.

In another embodiment of the present invention, one may transform a lovastatin-producing organism with the genes described above and obtain the production of an HMG CoA reductase inhibitor with a structure different from monacolin J, monacolin L or lovastatin. Alterations in the side chain attached to C8 are the most likely possibility but other alterations may occur. These alterations would happen through the native biochemistry of the organism.

If one wishes to express the *A. terreus* genes in yeast, one may wish to consult examples in which others have engineered fungal secondary metabolism genes for expression in yeast. (See for example, J. T. Kealey, et al., *Proc. Natl. Acad. Sci. USA* 95:505–509 (1998)). The exact approach could be used with the NPKS (LovB) and ScpKS (LovF) genes, and a somewhat simpler approach with the other lovastatin genes in their cDNA forms.

Production of HMG-CoA Reductase Inhibitors by Fungi and Yeast That Do Not Natively Produce Inhibitors In another embodiment, the present invention is the production of HMG-CoA reductase inhibitors, such as lovastatin, by fungi and yeast that do not natively produce lovastatin. An example of a suitable fungi or yeast is *A. nidulans* and *S. cerevisiae*, respectively.

Figure 2:
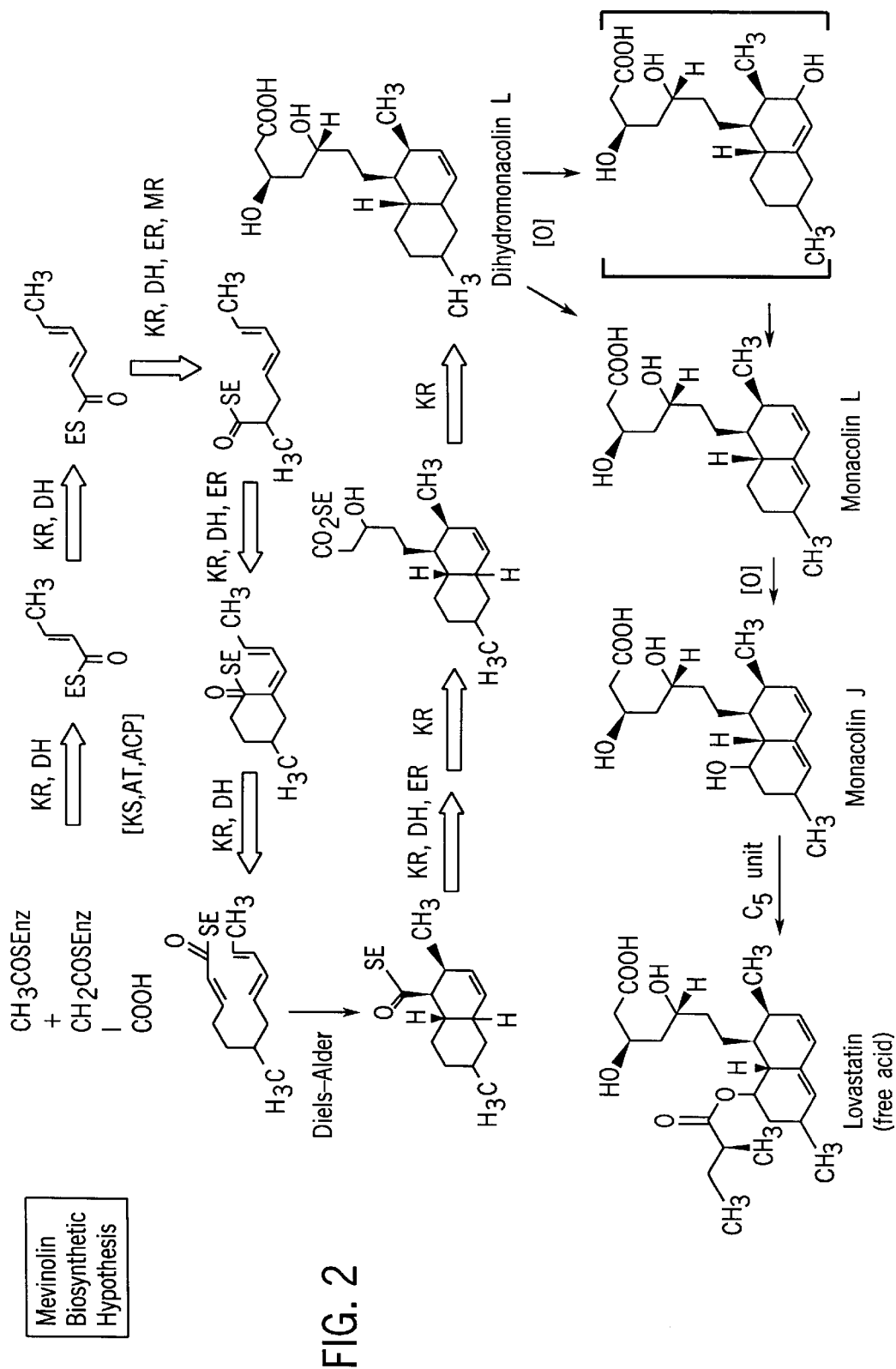
FIG. 2 is a schematic diagram of a hypothetical mevinolin/lovastatin biosynthesis pathway.

For this embodiment one preferably transforms the genes within the D4B segment into the non-inhibitor-producing strain. By this method, one would produce monacolin J (See FIG. 2) which could be chemically converted to lovastatin by one of skill in the art.

Monacolin J, in its lactone form obtained by treatment with anhydrous acid under dehydrative conditions, is preferably treated with a derivative of (2S)-2-methybutyric acid, in which the carboxyl group has been suitable activated for undergoing esterification, and the resulting lovastatin is isolated by conventional methods. For example, see WO 33538, U.S. Pat. No. 4,444,784 and *J. Med. Chem.* 29:849 (1986). These are citations for synthesis of simvastatin from monacolin J. One would use the same method, but use the (2S)-2-methylbutyrate derivative to make lovastatin.

In another embodiment of the present invention, one would transform the genes within the D4B segment, including an entire LovF/SCPKS gene, into the non-inhibitor-producing organism. By this method, one would produce lovastatin in a non-lovastatin-producing organism.

In another embodiment of the present invention, one may transform a non-lovastatin-producing organism with the genes described above and obtain the production of an HMG CoA reductase inhibitor with a structure different from monacolin J, monacolin L or lovastatin, as described above.

Modification of the LovB/NPKS gene would produce other inhibitors. For example, FIG. 3 diagrams the relationship between mevastatin, lovastatin, simvastatin and pravastatin. In one example, the methyl transferase domain of the NPKS gene may be replaced with an inactive form to make pravastatin. The HMG-CoA reductase inhibitors within this invention include, but are not limited to, compactin (ML-236B), lovastatin, simvastatin, pravastatin and mevastatin.

Production of Intermediate Materials

In another embodiment, the present invention is a method of isolating intermediate materials in the production of lovastatin and analogs such as mevastatin and simvastatin. For example, the Examples below demonstrate the disruption of the lovastatin projection gene cluster with mutagenized LovC, LovD, LovF, LovA or LovB genes. Disruption of many of these genetic elements of the lovastatin production gene cluster will result in accumulation of intermediate materials. Therefore, to practice this embodiment of the present invention, one would transform a suitable lovastatin-producing host with a mutagenized gene within the D4B segment, as described below.

Many other mutations would be suitable to destroy the function of LovC, LovD, LovF, LovA or LovB. All that is necessary is these genes be disrupted to the extent that they are non-functional.

Production of Lovastatin Analogs

In another embodiment, the present invention provides a method for engineering the production of lovastatin analogs in such organisms as fungi or yeast, using monacolin J as the starting point.

Isolated DNA Segments

In another embodiment, the present invention is a DNA segment capable of conferring lovastatin or monacolin J production or increase in lovastatin or monacolin J production in yeast or fungi. In a preferred example, this segment is the "D4B segment" that is deposited at ATCC 98876. The nucleotide sequence of this segment is found in residues 579–33,000 of SEQ ID NO:18 and residues 1–5,349 of SEQ ID NO:19.

In another embodiment, the present invention is the entire *A. terreus* lovastatin gene cluster, as exemplified by SEQ ID NOs:18 and 19 and ATCC deposits 98876 and 98877.

The present invention is also the individual genes that make up the *A. terreus* lovastatin gene cluster. Therefore, the present invention is a nucleic acid segment selected from the group of consisting of SEQ ID NOs:20–36. Preferably, the present invention is the coding region found within SEQ ID NOs:20–36 and described in Table 1. The present invention is also a mutagenized version of SEQ ID NOs:22, 24, 25 and 29, wherein the gene is mutagenized to be non-functional in terms of lovastatin or monacolin J production.

Organisms with Increased Lovastatin or Monacolin J Production

In another embodiment, the present invention are the organisms described above. These organisms include lovastatin-producing organisms, preferably yeast and fungi, that have been engineered to display at least a 2-fold increase in lovastatin or monacolin J production. The organisms also include non-lovastatin-producing organisms, preferably yeast or fungi, that have been engineered to produce monacolin J or lovastatin.

Antifungal Compounds

Applicants note that lovastatin, monocolin J, monocolin L and dihydromonocolin L all have varying degrees of antifungal activity. Applicants envision that the present invention is also useful for providing antifungal compounds and organisms engineered to express antifungal compounds. Preferably, one would measure the antifungal properties of a compound in the manner of N. Lomovskaya, et al., *Microbiology* 143:875–883, 1997. Measurement of inhibition of yeast growth can be found in R. Ikeura, et al., *J. Antibiotics* 41:1148, 1988. The same general methods could be used for all fungi. Both of these references are hereby incorporated by reference.

EXAMPLES

1. General Methods and Procedures

Construction of an *A. terreus* ATCC20542 Genomic Library

*A. terreus* ATCC20542 genomic DNA was partially digested with Sau3AI so as to produce an average fragment size of 40–50 kb. The partially digested genomic DNA was then separated on a sucrose gradient and the 40–50 kb fraction was collected. Cosmid AN26 (Taylor and Borgmann, *Fungal Genet. Newsletter* 43, 1996) was prepared by digestion with ClaI, dephosphorylated with CIP, then digested with BamHI to create the two cosmid arms. Ligation reactions with genomic DNA fragments and cosmid arms were optimized and packaged using Gigapack III XL packaging extract (Stratagene). The packaged cosmid library was infected into *E. coli* JM109 and plated out onto LB agar (Sambrook, et al., *Molecular Cloning. A Laboratory Manual.* 2nd ed. Cold Spring Harbour Laboratory Press, 1989; other standard methods used can be found here also) with ampicillin (50 µg/ml) plates. After checking for the presence of insert DNA in a selection of clones, 5000 colonies were picked into LB plus 50 µg/ml ampicillin filled microtitre plates and grown overnight at 37° C. The colonies were replica plated onto nylon membranes (Amersham Hybond-N). Glycerol was added at a final concentration of 15% (v/v) to the microtitre plates and these were stored at −70° C.

Isolation of Genomic Clones Containing the Lovastatin Biosynthesis Cluster

A 2.8 kb EcoRI fragment from pTPKS100 containing part of the NPKS gene (Vinci, et al., U.S. Pat. No. 5,744,350) was gel-isolated and labelled with digoxigenin using the Genius Kit II (Boehringer Mannheim). This labelled fragment was hybridized (65° C., 5×SSC) with the nylon membranes containing the A. terreus genomic library, then washed (65° C., 0.1×SSC). Two positive clones were identified, pWHM1263 (cD4B) and pWHM1264 (cJ3A). Two of these clones, pWHM1263 (cD4B) and pWHM1265 (cB2A4), have been deposited in the ATCC (American Type Culture Collection, 10801 University Boulevard, Manassas, Va. 20110) at accession number ATCC 98876 and 98877, respectively, under the terms and conditions of the Budapest Treaty. The presence of the NPKS gene was confirmed initially by restriction digestion and later by DNA sequencing.

Overlapping clones were found by repeating the hybridization process using labelled fragments from both ends of the insert in pWHM1263. This resulted in the isolation of pWHM1265-1270 (cB2A4, cL3E2, cJ3B5, cO2B5, cR3B2, cW3B1) from downstream of the NPKS gene and pWHM1271 (cQ1F1) from upstream of NPKS. All these clones were transformed into E. coli strain STBL2 (Stratagene) to help prevent rearrangements.

Figure 6:
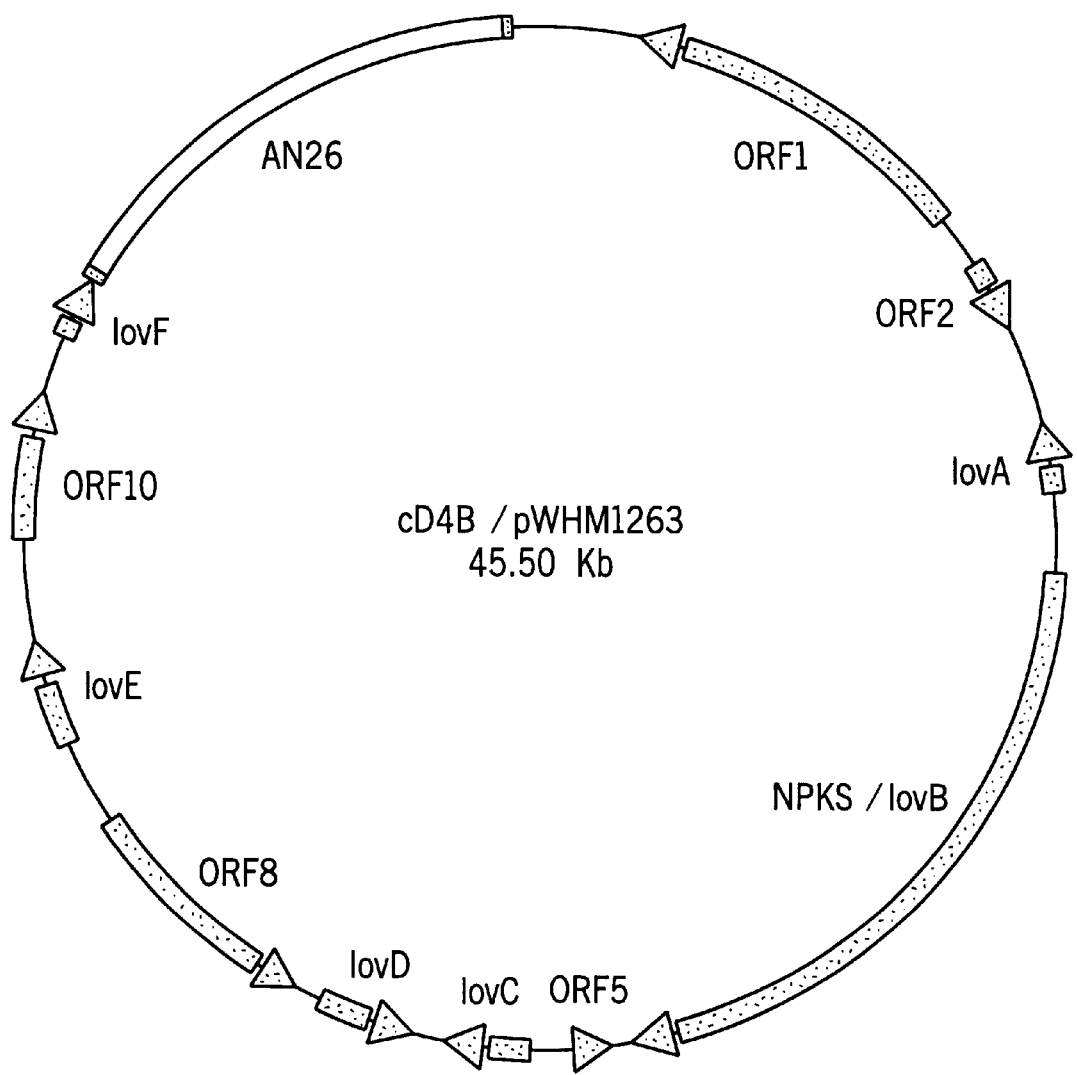
FIG. 6 is a schematic drawing of plasmid CD4B/pWHM1263.

FIG. 4 is a diagram of the cB2A4/pWHM1265 clone. This clone contains an insert of approximately 43 kb in AN26 and includes the nucleotide sequence from at least nucleotides 4988 of SEQ ID NO:19 to nucleotide 31,328 of SEQ ID NO:19 and 10–14 kb of uncharacterized DNA. FIG. 6 is a schematic diagram of cD4B/pWHM1263. This clone contains a 37,770 bp insert in AN26 and contains nucleotides 579–33,000 of SEQ ID NO:18 and nucleotides 1–5,349 of SEQ ID NO:19.

Sequencing Strategy and Analysis

A series of overlapping subclones (pWHM1272-pWHM1415) were constructed in pSPORT1 (Gibco-BRL) and pGEM3 (Promega). Plasmid DNAs for sequencing were prepared using the QiaPrep spin miniprep kit (Qiagen). Cycle sequencing was carried out using the AmpliTaq FS or BigDye reagents (ABI) and were analyzed using a ABI model 373 or 377 DNA Sequencer. Primer walking was performed by synthesis of 18–22 bp oligonucleotide primers based on the sequenced DNA strand, with the help of the Oligo 4.05 program (National Biosciences, Inc.). Every region of DNA was sequenced at least once on both strands. Direct sequencing of cosmids and PCR products was used to confirm adjoining regions where no overlapping clones existed. DNA sequence analysis and manipulations were performed using SeqMan (DNASTAR) and SeqEd (ABI) software. Assignments of putative ORFS, including putative introns, were performed with the aid of BLAST 2.0 searches (Atschul, et al., Nucl. Acids Res. 25:3389–3402, 1997), and the Genetics Computer Group (GCG) programs (Program Manual for the Wisconsin Package, Version 8, September 1994, Genetics Computer Group, Madison, Wis.), version 8.1.

Isolation and Characterization of lovF (ScPKS, ORF11), lovD (EST1, ORF7), lovC (DH, ORF6), and lovA (P450I, ORF3) Mutants lovF To disrupt the polyketide synthase gene, lovF, a 1.7 kb EcoRI fragment internal to the lovF gene was subcloned from pWHM1265 into pSPORT1 to give pWHM1291. The ScPKS fragment was then subcloned from this vector, as an Acc65I-HindIII fragment, into pPLOA (Vinci, et al., U.S. Pat. No. 5,744,350) to give pWHM1416. This vector contains the phleomycin (Zeocin, obtained from InVitrogen) resistance gene for selection in A. terreus. A. terreus ATCC20542 was then transformed to Zeocin resistance with this plasmid as described below. Transformants were screened for lovastatin production as described below (Method A). In one of the transformants, WMH1731, lovastatin production was abolished and a new compound accumulated. This new compound comigrated with monacolin J on TLC and HPLC according to the methods described below. Semi-preparative HPLC was used to partially purify the major product which was then analyzed by HPLC-MS. The same mass and fragmentation pattern as authentic monacolin J was observed. To confirm the disruption of the lovF gene, total genomic DNA was prepared from wild-type A. terreus ATCC20542 and the WMH1731 mutant strain. The genomic DNA was digested with BamHI and HindIII, electrophoresed on an agarose gel and capillary blotted onto a nylon membrane. The membrane was hybridized with the 1.7 kb EcoRI fragment from pWHM1416 labelled using the Genius II kit (Boehringer Mannheim) using the conditions described previously. The wild-type strain had hybridizing bands at 4.2 kb for BamHI and 11.5 kb for HindIII. As predicted, the WMH1731 mutant strain had hybridizing bands at 6.5 kb and 2.2 kb for BamHI and 11 kb and 7.8 kb for HindIII confirming the homologous integration of a single copy of pWHM1416 at the lovF locus.

lovD

To disrupt the putative esterase/carboxypeptidase-like gene, lovD, a 4.8 kb NotI-EcoRI fragment from pWHM1263 was subcloned into pSPORT1 to give pWHM1274. This plasmid was digested with HindIII and BsiWI and a 1.8 kb fragment was isolated. The plasmid was also digested with HindIII and BamHI and the 6.6 kb fragment was isolated. pPLOA was digested with BamHI and Acc65I and the 2.1 kb fragment containing the phleomycin resistance marker was purified. These three fragments were ligated together and used to transform competent E. coli cells. The expected plasmid, pWHM1417, containing the phleomycin resistance gene flanked by the beginning and the end of the lovD gene was isolated. This plasmid was linearized by digestion with XbaI or RsrII before being used to transform A. terreus ATCC20542 to Zeocin resistance. Transformants were screened for lovastatin production as described below (Method A). In one of the transformants, WMH1732, lovastatin production was abolished and a new compound accumulated. This new compound comigrated with monacolin J on TLC and HPLC according to the methods described below. Semi-preparative HPLC was used to partially purify the major product which was then analyzed by HPLC-MS. The same mass and fragmentation pattern as authentic monacolin J was observed. To confirm the disruption of the lovD gene, total genomic DNA was prepared from wild type A. terreus ATCC20542 and the WMH1732 mutant strain. The genomic DNA was digested with ApaI, run out on an agarose gel and capillary blotted onto a nylon membrane. The membrane was hybridized with the 4.8 kb NotI-EcoRI fragment from pWHM1274 labelled using the Genius II kit using the conditions described previously. The wild-type strain had hybridizing bands at 9 kb, 8.4 kb and 1.5 kb. As predicted the mutant strain had hybridizing bands at 9 kb, 8 kb, 3 kb and 1.5 kb confirming the homologous integration of a single copy of pWHM1417 at the lovD locus.

lovA

To disrupt the cytochrome P450 I gene, lovA, an 11 kb Acc65I-EcoRI fragment from pWHM1263 was subcloned into pGEM3 to give pWHM1272. From this plasmid a 2.1 kb ApaI-SnaBI fragment was purified and ligated to ApaI-EcoRV digested PPLOA to give p450Phleo (pWHM1418). From this plasmid a 4.2 kb ApaI-NotI fragment was purified and ligated with a 1.8 kb EagI-KpnI fragment from pWHM1272 and ApaI-KpnI digested pGEM7 to give p450Dphleo (pWHM1419) which contains the lovA gene disrupted by the phleomycin resistance gene. This plasmid was then digested with KpnI and ApaI and the resulting fragment was used to transform A. terreus ATCC20542 to Zeocin resistance. Transformants were screened for lovastatin production as described below (Method A). In one of the transformants, WMH1733, lovastatin production was abolished and two new compounds accumulated. Genomic DNA was prepared from this strain and from A. terreus ATCC20542, digested with EagI, run out on an agarose gel, and capillary blotted onto a nylon membrane. The membrane was hybridized with the 6 kb ApaI-KpnI fragment from pWHM1419 labelled using the Genius II kit using the conditions described previously. The wild-type strain had hybridizing bands at 2.0 kb, 1.9 kb and 1.1 kb. Mutant strain WMH1733 had hybridizing bands at 2.5 kb, 2.0 kb, 1.1 kb and 0.7 kb confirming the homologous integration of a single copy of the fragment from pWHM1419 at the lovA locus.

lovC

To disrupt the dehydrogenase-like gene, lovC, a 2 kb EcoRI-BglII fragment from pTPKS100 was ligated with a 1.7 kb EcoRI-SacI fragment from pWHM1274 and BglII-SacI digested litmus 28 (New England Biolabs) to produce pDH1 (pWHM1420). Another plasmid pDH2 (pWHM1421) was constructed from a 2.2 kb Acc65I-SacI fragment from pWHM1274, a 2.1 kb HindIII-SacI fragment from pPLOA containing the phleomycin resistance gene and HindIII-Acc65I digested litmus 28. The disruption vector pDH-dis (pWHM1422) was constructed by ligating together a 2.5 kb BglII-HpaI fragment from pWHM1420, a 4.3 kb EcoRV-KpnI fragment from pWHM1421 and BglII-KpnI digested litmus 28. This plasmid was digested with BglII and KpnI and the resulting 6.8 kb fragment was used to transform A. terreus ATCC20542 to Zeocin resistance. Transformants were screened for lovastatin production as described below (Method A). In two of the transformants, WMH1734 and WMH1735, lovastatin production was abolished. Genomic DNA was prepared from these strains and from A. terreus ATCC20542, digested with EagI, run out on an agarose gel, and capillary blotted onto a nylon membrane. The membrane was hybridized with the 6.8 kb Bgl II-KpnI fragment from pWHM1422 labelled using the Genius II kit using the conditions described previously. The wild type strain had hybridizing bands at 5 kb, 1.5 kb and 1.3 kb. Mutant strain WMH1734 had hybridizing bands at 4.9 kb, 1.3 kb, 1.0 kb and 0.7 kb confirming the homologous integration of a single copy of the fragment from pWHM1422 at the lovC locus. The other mutant strain, WMH1735, had a similar banding pattern but with additional hybridizing bands indicating that multiple integration events had occurred, one of which was at the lovC locus.

Figure 5:
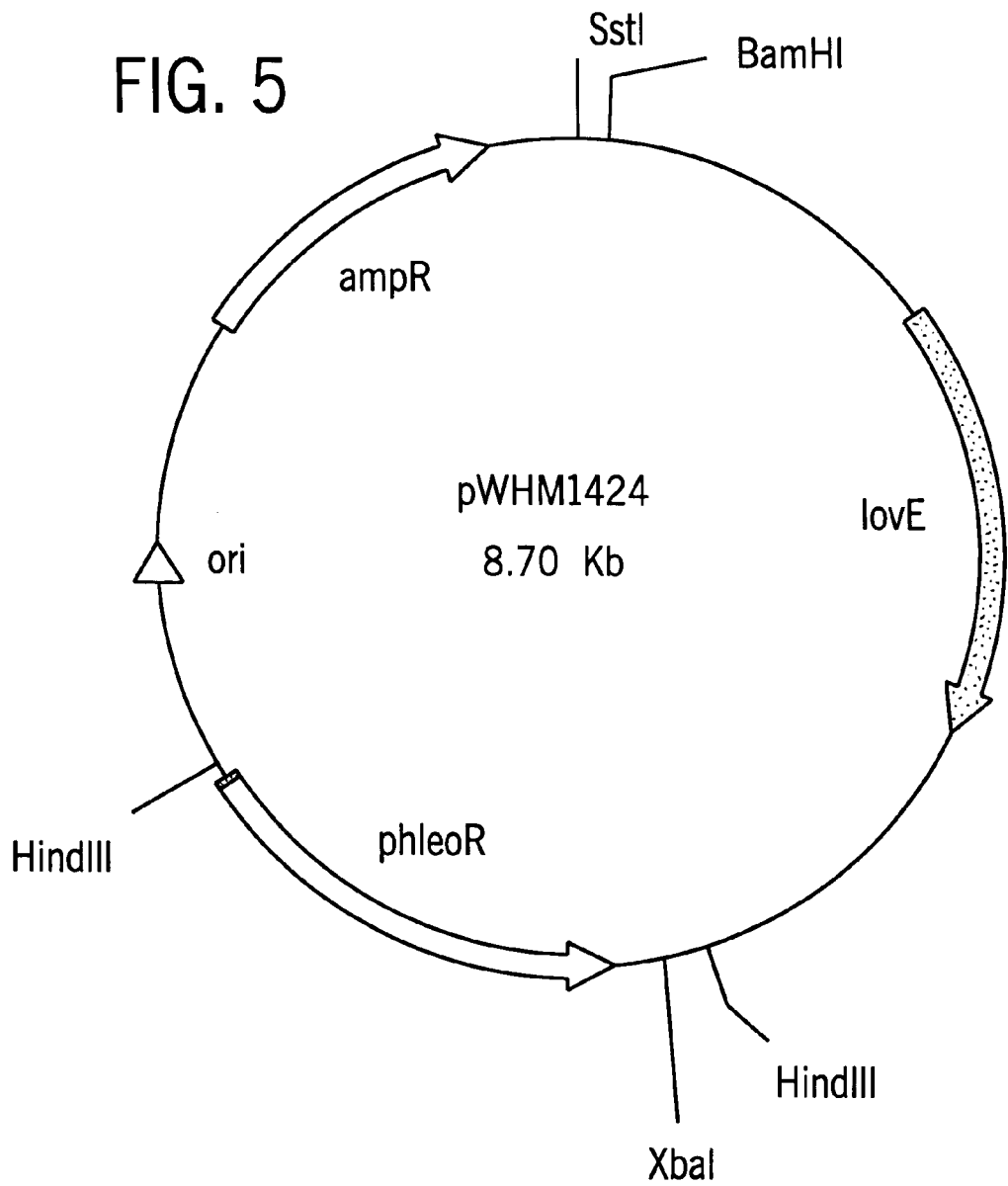
FIG. 5 is a schematic drawing of plasmid pWHM1424.

Construction and Characterization of the A. terreus Strain With Extra Copies of lovE A 10.4 kb NotI-EcoRI fragment containing the putative regulatory gene, lovE was subcloned from pWHM1263 to pSPORT1 to give pWHM1276. From this plasmid a 3.9 kb HindIII-BamHI fragment was subcloned into pGEM7 to give pWHM1423. The regulatory gene was subcloned from this vector into pPLOA as an SstI-XbaRI fragment to give pWHM1424 (FIG. 5). pWHM1424 contains nucleotides 30,055–33,000 from SEQ ID NO:18 and nucleotides 1–1,026 from SEQ ID NO:19.

Extra copies of the regulatory gene were introduced into A. terreus ATCC20542 by transformation to Zeocin resistance with pWHM1424. Transformants were fermented (method A) and screened for lovastatin production initially by TLC analysis. Most of the transformants appeared to be producing significantly more lovastatin than the wild-type strain. The yields of lovastatin from the two transformant strains, WMH1736 and WMH1737, which had the most elevated levels compared to the wild-type was quantified by HPLC as described below. These were found to produce 7-fold and 5-fold more lovastatin than the A. terreus ATCC20542 strain.

Because of the way that the DNA integrates (ectopically), each transformant is or can be unique, genotypically and phenotypically. However, some will be overproducers; others may exhibit no difference, for unknown reasons.

Heterologous Expression of the Lovastatin Biosynthesis Genes

To place the NPKS gene (lovB) under the control of the inducible alcA promoter, the 11.5 kb KpnI-AvrII fragment from pTPKS100 containing the NPKS open reading frame was ligated into pAL3 (Waring, et al., Gene 79:119, 1989) previously digested with KpnI and XbaI. The resulting plasmid was designated pAL3TPKS (WHM1425). The polymerase chain reaction was used to amplify the NPKS gene sequence between the NPKS promoter region just upstream of the translational start codon and a AgeI site internal to NPKS. The design of the forward primer introduced a KpnI site 31 bases from the translational start codon allowing the NPKS to be placed against the alcA promoter but also incorporating upstream elements from the A. terreus system. Amplification was performed using Vent DNA polymerase with pTPKS100 as template and 1 μmol of each primer in a final volume of 100 μl using the manufacturer's buffer recommendations. After an initial denaturation cycle of 10 minutes at 95° C. amplification was achieved with 30 cycles of 95° C. for 1 minute; 55° C. for 1 minute and 72° C. for 1.5 minutes. The final cycle was followed by 10 minutes at 72° C. to ensure complete polymerization. The amplified product (1.7 kb) was digested with KpnI and AgeI and ligated into pWHM1425 that had been digested with the same enzymes and gel isolated. The resulting plasmid was designated pAL3TPKSNT (pWHM1426). The region introduced by PCR was sequenced on a ABI automated DNA sequencer to ensure sequence fidelity. This plasmid was then used to transform A. nidulans strain A722 (Fungal Genetics Stock Centre) to uridine prototrophy.

Transformants were grown by inoculating 0.5 ml of spore suspension ($10^8$ c.f.u./ml) in 50 ml YEPD in a 250 ml unbaffled flask. This was then grown for 20 hours at 250 rpm and 37° C. (New Brunswick Scientific Series 25 Incubator Shaker). The mycelia were then harvested by filtration through Miracloth (Calbiochem), rinsed with sterile, distilled water, and inoculated into fresh 250 ml unbaffled flasks containing 50 ml AMM+lactose+10 mM cyclopentanone and grown for a further 20 hours under the same conditions. The mycelia were harvested by filtration using Miracloth (Calbiochem), squeezed as dry as possible and frozen in liquid nitrogen. Protein extracts for SDS-PAGE and western analysis were prepared as described in Kennedy and Turner, Molec. Gen. Genet. (1996), 253:189–197, 1996.

One transformant, WMH1738, was shown to have a large protein (>200 kDa) visible on a SDS-PAGE gel that cross reacted with the affinity purified NPKS antibodies (Panlabs). This strain WMH1738 was transformed to hygromycin B resistance with pWHM1263. Transformant colonies were screened for lovastatin resistance and for the production of new metabolites as described below and two strains WMH1739 and WMH1740 were chosen for further analysis. Both of these strains were found to be significantly resistant (up to 100 µg/ml on solid media) to lovastatin compared with the host strain. This was analyzed by streaking 10 µl of a spore suspension on solid AMM plates containing lovastatin at 0, 0.1, 0.5, 1, 5, 10, 50 and 100 µg/ml and incubating at 37° C. Strains WMH1739 and WMH1740 were compared to strains WMH1741 and WMH1742 which were derivatives of WMH1738 transformed to hygromycin resistance with AN26. Strains WMH1739 and -1740 exhibited no inhibition of growth at any of these lovastatin concentrations whereas strains WMH1741 and -1742 showed slight inhibition of grown at 5 µg/ml and almost complete growth inhibition at 50 µg/ml. The two lovastatin resistant strains were fermented in lovastatin-producing conditions using fermentation method B and extracts were analyzed for lovastatin related metabolites as described below. Both strains were found to produce new metabolites. One compound that was common to both comigrated with monacolin J on TLC and HPLC analysis by the methods described below. Semi-preparative HPLC was used to partially purify some of this compound, which was then analyzed by HPLC-MS. It had the same mass and fragmentation pattern as authentic monacolin J. The other compound, found in only one of the strains, comigrated with monacolin L on TLC and HPLC.

Methods

Solid medium for growth of *A. terreus*

For the generation of spore suspensions *A. terreus* strains were grown on CM agar at 30° C. for 4 to 5 days.

CM Agar (for CM liquid medium the agar was omitted):
50 ml Clutterbuck's salts (Vinci, et al., U.S. Pat. No. 5,744,350)
2 ml Vogel's trace elements (Vinci, et al., U.S. Pat. No. 5,744,350)
0.5% Difco Bacto tryptone
0.5% Difco Bacto yeast extract
1% glucose
2% Difco Bacto agar
in 1 liter of distilled water Clutterbuck's salts:
12% $NaNO_3$
1.02% KCl
1.04% $MgSO_4.7H_2O$
3.04% $KH_2PO_4$ Vogel's trace elements:
0.004% $ZnCl_2$
0.02% $FeCl_3$
0.001% $CuCl_2$
0.001% $MnCl_2.4H_2O$
0.001% $Na_2B_4O_7.10H_2O$
0.001% $(NH_4)_6Mo_7O_{24}.7H_2O$ For long term storage *A. terreus* spores were suspended in SSS (10% glycerol, 5% lactose) and stored at −70° C.

For the generation of spore stocks *A. nidulans* was grown on the following solid growth medium (ACM) for 3 to 4 days at 37° C.

ACM:
2% Difco Bacto malt extract
0.1% Difco Bacto peptone
2% glucose
2% agar (Difco, Detroit, Mich.)

For strains which required para-aminobenzoic acid (PABA) for growth, PABA was added to a final concentration of 1 µg/ml. For strains which required uracil and uridine these were added at 20 mM and 10 mM, respectively. Spores were suspended in Tween 80—saline solution (0.025% Tween 80, 0.8% NaCl) and stored at 4° C.

AMM:
0.6% (w/v) $NaNO_3$
0.052% (w/v) KCl
0.152% (w/v) $KH_2PO_4$
0.052% (w/v) $MgSO_4.7H_2O$
1% (w/v) glucose
0.1% (v/v) AMM trace elements solution
pH to 6.5 and make up to 1 liter with distilled water.

For preparation of plates 2% (w/v) Difco Bacto agar was added. If required the glucose can be omitted and an alternative carbon source (e.g., lactose added at the same concentration). For the preparation of transformation plates KCl was added at 4.47% (w/v) (0.6 M).

AMM trace elements solution:
0.1% (w/v) $FeSO_4.7H_2O$
0.88% (w/v) $ZnSO_4.7H_2O$
0.04% (w/v) $CuSO_4.5H_2O$
0.015% (w/v) $MnSO_4.4H_2O$
0.01% (w/v) $Na_2B_4O_7.10H_2O$
0.005% $(NH_4)_6Mo_7O_{24}.7H_2O$
distilled water to 1 liter Large Scale Genomic DNA Preparation From *A. terreus* for Genomic Library Construction A 2.5 ml aliquot of spore suspension ($10^8$ c.f.u./ml) was used to inoculate 500 ml of liquid CM medium and grown for 20 hours at 30° C. and 200 rpm. The mycelium was harvested by filtration through Miracloth (Calbiochem) and rinsed extensively with water then TSE [150 mM NaCl, 100 mM $Na_2$EDTA, 50 mM Tris-HCl pH 8.0]. The mycelium was squeezed dry, broken into small pellets and frozen in liquid nitrogen then ground to a fine powder in a pre-chilled pestle and mortar followed by transferral to a 500 ml flask. Fifty ml of extraction buffer [150 mM NaCl, 100 mM $Na_2$EDTA, 50 mM Tris-HCl pH 8.0, 2% (w/v) SDS] and 10 ml of toluene was added to the flask which was shaken at 60 rpm for 72 hours. This mixture was centrifuged at 1000×g for 15 minutes and the supernatant was removed and extracted with an equal volume of chloroform:isoamyl alcohol (24:1 vol/vol). This mixture was centrifuged at 10,000×g for 30 minutes at 15° C. The aqueous layer was carefully removed and 1.1 volumes of ethanol was layered on top. The DNA was spooled out from the resulting suspension and resuspended in 5 ml TE [10 mM Tris-HCl pH 8.0, 1 mM EDTA]+50 µg/ml RNase and 100 µg/ml proteinase K then incubated at 37° C. for 2 hours. The mixture was extracted again with chloroform:isoamyl alcohol (24:1) and the DNA was spooled out as before. Following resuspension in 1 ml of TE the DNA was extracted once with phenol:chloroform:isoamyl alcohol (25:24:1, vol/vol), once with chloroform:isoamyl alcohol (24:1) and precipitated with 0.6 volumes isopropanol. The DNA clot was removed, dried briefly and resuspended in 0.5 ml TE.

Small Scale Genomic DNA Preparation From *A. terreus* for Southern Blot

A 0.5 ml aliquot of spore suspension ($10^8$ c.f.u./ml) was used to inoculate 100 ml of liquid CM and grown for 20 hours at 3° C. and 200 rpm. The mycelium was harvested by filtration through Miracloth (Calbiochem) and rinsed extensively with water then TSE [150 mM NaCl, 100 mM $Na_2$EDTA, 50 mM Tris-HCl pH 8.0]. The mycelium was squeezed dry, broken into small pellets and frozen in liquid nitrogen. The mycelium was ground to a fine powder in a pre-chilled pestle and mortar and transferred to a mortar pre-heated to 65° C. Three ml of lysis buffer [0.5 M NaCl, 10 mM Tris-HCl pH 7.5, 10 mM EDTA, 1% (w/v) SDS] at 65° C. was added and 0.3 ml of 10% (w/v) cetyltrimethylammonium bromide in 0.7 M NaCl. After thorough mixing to form a slurry, 3 ml of phenol:chloroform:isoamyl alcohol (25:24:1) was added. This mixture was transferred to a Corex tube and incubated at 65° C. for 15 minutes. Following centrifugation at 12,000×g for 15 minutes at 40° C. the aqueous phase was carefully removed and re-extracted once with phenol, once with phenol:chloroform:isoamyl alcohol (25:24:1) and once with chloroform:isoamyl alcohol (24:1). The DNA was precipitated from the extract by addition of 0.1 volume of 3 M sodium acetate pH 5 and 0.6 volumes isopropanol then collected by centrifugation (10,000×g, 10 minutes, 40° C.). After washing with 70% ethanol the pellet was briefly dried and resuspended in TE+RNase (50 $\mu$g/ml).

Transformation of *A. terreus*.

A 0.5 ml aliquot of spore suspension ($10^8$ c.f.u./ml) was used to inoculate 100 ml of liquid CM and grown for 20 hours at 30° C. and 200 rpm. The mycelium was harvested by centrifugation at 2000×g for 15 minutes at 40°C. and washed twice with an aqueous solution containing 0.27 M $CaCl_2$ and 0.6 M NaCl. To produce protoplasts the washed mycelia was resuspended in 20 ml of the same solution containing 5 mg/ml Novozym 234 (NovoNordisk) and incubated at 30° C. for 1–3 hours with gentle agitation. Protoplasts were separated from undigested mycelia by filtration through Miracloth (Calbiochem). The protoplast suspension was diluted with an equal volume of STC1700 [1.2 M sorbitol, 10 mM Tris-HCl pH 7.5, 35 mM NaCl] and incubated on ice for 10 minutes. The protoplasts were collected by centrifugation (2000×g, 10 minutes, 40° C.), washed with STC1700 and resuspended in 1 ml STC1700. Plasmid DNA, purified using Qiagen columns, (2–5 $\mu$g in 10 $\mu$l) was added to 150 $\mu$l of protoplast suspension and incubated at room temperature for 25 minutes. PEG solution [60% (w/v) polyethylene glycol 4000, 50 mM $CaCl_2$, 10 mM Tris-HCl pH 7.5] was added to the DNA/protoplasts mixture in three steps: 250 $\mu$l, 250 $\mu$l, and 850 $\mu$l with mixing after each addition. The suspension was incubated at room temperature for 25 minutes then diluted to 10 ml with STC1700. Protoplasts were collected by centrifugation as above and diluted with 500 $\mu$l STC1700. 100 $\mu$l aliquots of this mixture were plated onto osmotically stabilized plates [CM medium containing 3% (w/v) Difco Bacto agar and 23.4% (w/v) mannitol, 15 ml of agar per plate]. After 4 hours growth at 30° C., 25 ml of OL agar [1% (w/v) Difco Bacto peptone, 1% (w/v) Difco Bacto agar, 200 $\mu$g/ml Zeocin] was overlayered onto each dish. The plates were incubated for 3–4 days at 30° C. before transformant colonies were picked. These were streaked to single colonies twice on selective media (CM+100 $\mu$g/ml Zeocin) before spore suspensions were prepared.

Transformation of *A. nidulans*

A 0.5 ml aliquot of spore suspension ($10^8$ c.f.u./ml) was used to inoculate 100 ml of YEPD [2% (w/v) Difco Bacto yeast extract, 2% (w/v) glucose, 0.1% Difco Bacto peptone] liquid medium including necessary supplements and grown for 20 hours at 37° C. and 200 rpm. The mycelia was harvested by centrifugation (2000×g, 10 minutes, 4° C.) and washed twice with 0.6 M KCl. To generate protoplasts the mycelia was resuspended in 20 ml of 0.6 M KCl containing 5 mg/ml Novozym 234 and incubated at 30° C. for 1–2 hours with gentle shaking. Protoplasts were separated from undigested mycelia by filtration through Miracloth (Calbiochem). The protoplasts were harvested by centrifugation as described above and washed twice with 0.6 M KCl, then resuspended in 10 ml 0.6 M KCl+50 mM $CaCl_2$. After counting in a haemocytometer the protoplasts were harvested by centrifugation as before and resuspended to a final concentration of $5 \times 10^8$ protoplasts/ml. To 50 $\mu$l of protoplast suspension, 5 $\mu$l of DNA (2–5 $\mu$g, purified using Qiagen columns) was added, then 12.5 $\mu$l of PEG solution [25% (w/v) PEG 6000, 50 mM $CaCl_2$, 10 mM Tris-HCl pH 7.5] and the mixture was incubated on ice for 20 minutes. A further 0.5 ml of PEG solution was added and the mixture was incubated on ice for a further 5 minutes. A 1 ml aliquot of 0.6 M KCl+50 mM $CaCl_2$ was added and the protoplasts were plated out in 50 $\mu$l, 200 $\mu$l, and 400 $\mu$l aliquots. For transformation to uridine prototrophy, protoplasts were plated out onto AMM+0.6 M KCl plates without adding uridine or uracil supplements. Plates were incubated at 37° C. for 3–4 days when transformants were picked. For transformation to hygromycin B resistance protoplasts were plated out onto AMM+0.6 M KCl plates (15 ml) and incubated for 4 hours at 30° C. 30 ml of 1% peptone, 1% agar, 1 mg/ml hygromycin B was then used to overlay the plates, which were incubated for 3–4 days when transformants were picked. Transformants from both methods were streaked out to single colonies on selective media (i.e., lacking uridine/uracil supplements or containing 1 $\mu$g/ml hygromycin B) twice before spore suspensions were made.

Analysis of Strains for Lovastatin Production

Two fermentation methods were used for the analysis of lovastatin production. In Method A, 0.5 ml of spore suspension ($10^8$ c.f.u./ml) was inoculated into 25 ml of SEED medium in 250 ml unbaffled flasks and grown for 18 hours at 250 rpm and 30° C. (New Brunswick Scientific Model 25 incubator/shaker). A 1 ml portion of the resulting seed culture was used to inoculate 25 ml of FM in a 250 ml unbaffled flask and grown for 6 days in the conditions described above. Fermentation Method B involved inoculating 50 ml of RPM in a 250 ml unbaffled flask with 0.5 ml of spore suspension ($10^8$ c.f.u./ml) and growing at 30° C. and 250 rpm for 7 days in a New Brunswick Scientific Series 25 Incubator Shaker.

SEED medium:
0.5% (w/v) Sigma corn steep liquor
4% (w/v) tomato paste
1% (w/v) oat flour
1% (w/v) glucose
1% (v/v) Vogel's trace elements
distilled water to 1 l FM:
4.5% (w/v) glucose
2.4% (w/v) Sigma peptonized milk
0.25% (w/v) Difco Bacto yeast extract
0.25% (w/v) polyethylene glycol 2000
distilled water up to 1 l RPM:
4% (w/v) lactose
0.3% (w/v) rapeseed meal
0.2% (w/v) $KNO_3$
0.3% (w/v) $KH_2PO_4$
0.05% (w/v) $MgSO_4 \cdot 7H_2O$
0.05% (w/v) NaCl
0.05% (v/v) Sigma antifoam B
0.05% (v/v) trace elements solution
pH to 6.5 and made up to 1 l with distilled water.

Trace elements solution is:
0.16% (w/v) $MnSO_4$
0.34% (w/v) $ZnSO_4 \cdot 7H_2O$ 0.2% (w/v) CoCl$_2$. 6H$_2$O
0.5% (w/v) FeSO$_4$. 7 H$_2$O
made up to 1 liter with distilled water.

The cultures were extracted by adjusting the pH of the media to 3 with HCl, adding an equal volume of ethyl acetate, and shaking the mixture on a New Brunswick Scientific Series 25 incubator/shaker at 250 rpm for 2 hours. For analysis, 1 ml of the ethyl acetate layer was dried under a nitrogen stream and resuspended in 0.1 ml of methanol. For TLC analysis 10 µl of this extract was run on C-18 reverse phase TLC plates (RP-18 F$_{254}$-Merck) in a solvent system of methanol:0.1% phosphoric acid (9:1). TLC plates were developed by spraying with 10% phosphomolybdic acid in methanol and heating with a heat gun. Extracts were compared with authentic lovastatin, monacolin J, monacolin L, and dihydromonacolin L (acid and lactone forms). For HPLC analysis a Waters Nova-Pak C$_{18}$ (3.9×150 mm) column was used with a solvent system of acetonitrile (B) and 0.1% phosphoric acid (A). The column was eluted with a preprogrammed gradient of 0 to 100% B into A over 25 minutes using gradient 7 (Waters Millenium Software) with a flow rate of 1.5 ml/min and metabolites were detected with a Waters 996 Photodiode Array Detector; lovastatin was detected at 238 nm. For purification of metabolites a Waters Prep Nova-Pak HR C$_{18}$ (7.8×300 mm) column was used. The same solvent system as above was used with gradient of 0 to 100% B in A over 75 minutes at a flow rate of 4.5 ml/min. Fractions were collected manually, back extracted with ethyl acetate and dried. For HPLC-MS an Aquapore OD-300 7 micron (1.0×100 mm) column was used with a gradient of 0 to 100% acetonitrile into A (0.05% TFA) over 30 minutes at a flow rate of 0.02 ml/min.

We claim:

1. A method of increasing the production of lovastatin in a lovastatin-producing organism, comprising the steps of transforming the organism with the D4B segment, wherein the segment is transcribed and translated, and wherein an increase in lovastatin to production occurs wherein the increase is at least 5-fold.

2. The method of claim 1 wherein the D4B segment is the *Aspergillus terreus* D4B segment.

3. The method of claim 1, wherein the D4B segment is identical to nucleotides 579–33,000 of SEQ ID NO:18 or 1–5,349 of SEQ ID NO:19.

4. The method of claim 1, wherein the lovastatin-producing organism is selected from the group consisting of *Aspergillus terreus* ATCC 20542 and ATCC 20541.

5. The method of claim 1, wherein the organism is selected from the group consisting of fungi and yeast.

6. The method of claim 1 wherein the nucleic acid sequence is identical to a sequence isolated from ATCC 98876.

7. The method of claim 1 additionally comprising transforming the organism with the entire *Aspergillus terreus* lovastain gene cluster.

8. The method of claim 7 wherein the gene cluster comprises SEQ ID NOs:18 and 19.

9. The method of claim 7 wherein the nucleic acid sequence of the gene cluster is identical to sequences isolated from ATCC 98876 or 98877.

10. A method of increasing the production of monacolin J in a lovastatin-producing organism, comprising the steps of transforming the organism with the D4B segment, wherein the segment is translated, and wherein an increase monacolin J production occurs relative to a non-transformed organism.

11. A method of increasing the production of lovastatin in a lovastatin-producing organism, comprising the step of transforming the organism with the LovE gene, wherein the nucleic acid sequence is translated, wherein an increase in lovastatin production occurs and wherein the increase is at least 5-fold.

12. The method of claim 11 wherein the nucleotide sequence of the LovE gene comprises SEQ ID NO:27.

13. A method of increasing the production of lovastatin in a lovastatin-producing organism comprising the steps of transforming the organism with a nucleic acid sequence comprising a truncated version of the *A. terreus* D4B segment, wherein the nucleic acid sequence is transcribed and translated and wherein an increase in lovastatin production occurs wherein the increase is at least 5-fold relative to a non-transformed organism.

14. A method of increasing the production of lovastatin in a lovastatin-producing organism comprising the steps of transforming the organism with a nucleic acid sequence comprising a truncated version of the *A. terreus* lovastatin-producing gene cluster, wherein the nucleic acid sequence is transcribed and translated and wherein an increase in lovastatin production occurs wherein the increase is at least a 5-fold relative to a non-transformed organism.

15. A method of increasing or conferring the production of monacolin J in a non-lovastatin-producing organism comprising the steps of transforming the organism with a nucleic acid sequence comprising the D4B segment, wherein the nucleic acid sequence is transcribed and translated and wherein an increase in monacolin J production occurs wherein the increase is at least 5-fold relative to a non-transformed organism.

16. The method of claim 15 wherein the D4B segment is the *A. terreus* D4B segment.

17. The method of claim 15 wherein the D4B segment comprises nucleotides 579–33,000 of SEQ IID NO:18 or 1–5,349 of SEQ ID NO:19.

18. The method of claim 15 additionally comprising the step of converting the monacolin J into lovastatin.

19. The method of claim 15 additionally comprising the step of transforming the organism with a nucleic acid sequence comprising the LovF gene, wherein the nucleic acid sequence is transcribed and translated and wherein an increase in lovastatin production occurs.

* * * * *

UNITED STATES PATENT AND TRADEMARK OFFICE
CERTIFICATE OF CORRECTION

PATENT NO. : 6,391,583 B1
DATED : May 21, 2002
INVENTOR(S) : Charles R. Hutchinson et al.

It is certified that error appears in the above-identified patent and that said Letters Patent is hereby corrected as shown below:

<u>Column 7,</u>
Line 64, "same" should read -- some --.

<u>Column 13,</u>
Line 6, "PPLOA" should read -- pPLOA --.

<u>Column 16,</u>
Line 63, "3°" should read -- 30° --.

<u>Column 17,</u>
Lines 10 and 17, "40°" should read -- 4° --.
Lines 23 and 34, "40°" should read -- 4° --.

<u>Column 18,</u>
Line 60, "$MgSO_4$." should read -- $MgSO_4\cdot$ --.
Line 67, the period "." should not be subscript.

<u>Column 19,</u>
Lines 1 and 2, the period "." should not be subscript.

<u>Column 165,</u>
Line 6, "lovastain" should read -- lovastatin --.
Line 45, "lovastatin to production" should read -- lovastatin production --.
Line 45, after "5-fold" insert -- -relative to a non-transformed organism --.

<u>Column 166,</u>
Line 42, after "occurs relative" insert -- -relative to a non-transformed organism --.
Line 48, after "5-fold" insert -- -relative to a non-transformed organism --.

UNITED STATES PATENT AND TRADEMARK OFFICE
CERTIFICATE OF CORRECTION

PATENT NO.    : 6,391,583 B1
DATED         : May 21, 2002
INVENTOR(S)   : Charles R. Hutchinson et al.

It is certified that error appears in the above-identified patent and that said Letters Patent is hereby corrected as shown below:

<u>Column 167,</u>
Line 10, "IID" should read -- ID --.

Signed and Sealed this

Seventeenth Day of June, 2003

JAMES E. ROGAN
*Director of the United States Patent and Trademark Office*

SEQUENCE LISTING

```
<160> NUMBER OF SEQ ID NOS:  36

<210> SEQ ID NO 1
<211> LENGTH: 1529
<212> TYPE: PRT
<213> ORGANISM: Aspergillus terreus

<400> SEQUENCE: 1

Met Ala Ser Leu Leu Phe Phe Thr Val Phe A sn Leu Thr Leu Ala Leu
  1               5                  10                  15

Leu Ser Ser Thr Ala Thr Gly Ala Ala Val P ro Val Ser Arg Pro Thr
                 20                  25                  30

Asp Asp Ser Arg Tyr Ile Asp Phe Asp Ala A la Glu Trp Arg Pro Arg
             35                  40                  45

Ala Lys Arg Asp Asp Ala Leu Lys Val Pro L eu Arg Ile Leu Pro Leu
     50                  55                  60

Gly Ala Ser Ile Thr Trp Gly Tyr Leu Ser S er Thr Gly Asn Gly Tyr
 65                  70                  75                  80

Arg Lys Pro Leu Arg Asp Lys Leu Arg Phe G lu Gly Trp Glu Val Asp
                 85                  90                  95

Met Val Gly Lys Ala His Ser Gly Asp Val I le Thr Gln Val Gln Thr
                100                 105                 110

Ala Ala Ala Asn Ser Leu Ala Tyr Lys Pro A sn Val Val Leu Ile Asn
            115                 120                 125

Ala Gly Thr Asn Asp Cys Asp Tyr Asn Val A sp Pro Ala Asn Ala Gly
        130                 135                 140

Glu Arg Met Arg Ser Leu Ile Glu Thr Leu I le Gly Ala Pro Asp Met
145                 150                 155                 160

Ala Asn Thr Leu Ile Val Leu Ser Thr Leu I le Pro Ser Gly Ser Thr
                165                 170                 175

Thr Leu Glu Ala Asn Arg Pro Ser Val Asn A la Gln Phe Arg Glu Leu
            180                 185                 190

Val Leu Asp Met Arg Glu Ala Gln Asn Val S er Ile Val Leu Ala Asp
        195                 200                 205

Met Asp Pro Pro Ala Pro Ser Pro Gly Asn A sn Trp Ile Thr Tyr Pro
    210                 215                 220

Asp Asn Phe Ala Asp Asn Lys His Pro Asn A sp Tyr Gly Tyr Ser Gln
225                 230                 235                 240

Met Ala Asp Ile Trp Tyr Asn Ala Ile Tyr A sn Ala Ala Val Ala Glu
```

-continued

```
                245                 250                 255
Leu Ile Val Lys Pro Ala Asp Leu Asp Ile S er Ser Thr Gly Thr Cys
                260                 265                 270
Asp Lys Glu Tyr Gly Ser Gly Val Tyr Ala G ly Gly Phe Thr Gln Gln
            275                 280                 285
Gly Ser Gly Glu Asp Asp Gly Ile Tyr Arg H is Asp Ser Glu Tyr Ser
        290                 295                 300
Gly Ala Leu Phe Thr Val Arg Ala Gly Lys G ly Ala Ala Asp Pro Tyr
305                 310                 315                 320
Lys Asp Asp Asp Glu Leu His Phe Phe Phe G ly Arg Leu Tyr Thr Arg
                325                 330                 335
Ala Tyr Asp Asp Met Met Ile Phe His Lys A sp Lys Asp Ser Gly Ala
            340                 345                 350
Val Thr Phe Val Ser Tyr Thr Asn Asn Val H is Thr Glu Glu Gln Glu
            355                 360                 365
Phe Thr Lys Gly Gly Thr Phe Ser Thr His A sn Asn Cys Asn Pro Gly
    370                 375                 380
Gly Val His Phe Ile Asp Ile Asn Gly Asp G ly Leu Asp Asp Tyr Ile
385                 390                 395                 400
Cys Ile Ala Leu Asp Gly Thr Thr Tyr Ala S er Ile Asn Asn Gly Asp
                405                 410                 415
Gly Asp Ala Lys Ser Asn Lys Pro Pro Ser P he Thr Asp Ile Gly Leu
            420                 425                 430
Trp Lys Ser Pro Glu Gly Tyr Asp Gln Ala H is Val Arg Leu Ala Asp
                435                 440                 445
Ile Asp Gly Asp Gly Arg Ala Asp Tyr Cys G ly Leu Ala Asp Asn Gly
    450                 455                 460
Asp Val Thr Cys Trp Arg Asn Gly Trp Ile G lu Asp Ile Pro Ala Tyr
465                 470                 475                 480
Trp Gln Pro Leu Gly Lys Arg Phe Thr Gly L ys Val Met Gly Asp Leu
                485                 490                 495
Arg Gly Val Arg Phe Glu Asp Ile Asn Gly A sp Gly Arg Asp Asp Trp
            500                 505                 510
Met Trp Val Asp Asp Gly Ala Thr Thr T hr Tyr Thr Asn Ser Arg
            515                 520                 525
Ser Cys Ile Lys Gly Glu Ser Gly Asp Gly L eu Asn Val Val Trp Arg
    530                 535                 540
Gln Gly Phe Tyr Gln Asp Ala Asn Ser Gly P ro Ser His Pro Gly Met
545                 550                 555                 560
Gly Val Ile Phe Gly Thr Ser Gly Leu Arg A sp Gln Val Tyr Phe Ala
                565                 570                 575
Arg Leu Tyr Gly Glu Val Ala Asp Phe Gly G lu Leu Gly Arg Gln Asp
            580                 585                 590
Tyr Val Phe Ile Lys Lys Asp Thr Ser Asp L ys Tyr Phe Gly Pro Leu
            595                 600                 605
Tyr Tyr Val His Val Trp Lys Ser Lys Gly A la Gly Gly Ala Lys Ile
        610                 615                 620
Lys Ala Asp Gly Asp Arg Tyr Cys Asn Met M et Gly His Asp Asn Gly
625                 630                 635                 640
Met Met Asp Tyr Ile Trp Ile His Ser Thr G ly His Met Arg Leu Tyr
                645                 650                 655
Pro Asn Arg Gly Leu Val Glu Val Pro Ala A sp Gly Ser Ser Phe Trp
            660                 665                 670
```

-continued

```
Gly Ala Asn Glu Ile Ile Phe Asp Pro Gln Glu Gln Ile Gly Met Lys
            675                 680                 685
Leu Asp Arg Arg Asp Leu His Leu Ala Asp Trp Asp Gly Asp Gly Ala
    690                 695                 700
Cys Asp Ile Ile Trp Thr Asp Pro Asp Asn Leu Asn Arg Ala Gln Val
705                 710                 715                 720
Trp Arg Asn Lys Ile Lys Asp Thr Gly Ser Phe Asp Trp Asp Tyr Asn
                725                 730                 735
Ile Asn Ala Ala Asp Glu Leu Tyr Cys Pro Glu His Arg Gly Leu Gly
            740                 745                 750
Phe Phe Asp Arg Pro Val His Phe Ala Asp Val Ser Gly Asn Gly Lys
        755                 760                 765
Ala Asp Tyr Leu Cys Val Glu Lys Asp Gly Arg Thr Trp Gly Trp Val
    770                 775                 780
Asn Gly Asp Asp Gly Trp Asp Tyr Ile Asp Gln Phe Lys Tyr Ser Glu
785                 790                 795                 800
Glu Lys Asp Arg Ala Asn Leu His Trp Ala Asp Val Asn Gly Asp Gly
                805                 810                 815
Lys Ala Asp Met Ile Trp Thr Asp Lys Phe Ser Gly Asp Gly Ser Val
            820                 825                 830
Trp Tyr Asn Leu Gly Gln Arg Asp Ile Lys Gly Ser Arg Tyr Glu Trp
        835                 840                 845
Gly Pro Gln Gly Pro Lys Tyr Arg Gly Ala Val Glu Gly Ser Cys Thr
    850                 855                 860
Tyr Phe Pro Asp Leu Asn Gly Asp Gly Arg Ala Asp Met His Ser Ile
865                 870                 875                 880
Trp Asn Ser Ile Asn Asn Thr Ala Gln Thr Trp Tyr Asn Glu Cys Ala
                885                 890                 895
Thr Lys Asp His Thr Gly Asp Asp Gly Pro Ile Thr Asn Pro Asn Leu
            900                 905                 910
Pro Val Ser Pro Val Lys Ala Pro Ile Glu Leu Thr Pro His Tyr Gln
        915                 920                 925
Asp Asn Ser Glu Cys Thr Arg Ala Gln Val Gln Thr Leu Phe Glu Glu
    930                 935                 940
Met Gln Tyr Ala Leu Asp Ala Ala Ser Glu Val Ala Tyr Phe Ser Gly
945                 950                 955                 960
Gly Ala Tyr Asp Pro Tyr Arg Asp Ile Phe Phe Ala Glu Ser Leu Thr
                965                 970                 975
Asp Ser Leu Thr Phe Thr Ile Asn Val Arg Tyr Thr Phe Asp Arg Met
            980                 985                 990
Val Thr Met Ile Ser Gly Ser Ser Gln Phe Asp Asp Glu Lys Phe Thr
        995                 1000                1005
Ile Thr Cys Lys Asn Leu Arg Gly Cys Asp Glu Asn Gly Trp Leu Ala
    1010                1015                1020
Met Met Asn Asn Arg Asn Arg Leu Asn Phe Cys Pro Lys Phe Phe Thr
1025                1030                1035                1040
Asp Glu Leu Lys Ser Ser Arg Arg Thr Arg Asp Tyr Val Tyr Gly Trp
                1045                1050                1055
Lys Gly Ala Arg Asp Leu Ala Ala Gly Thr Phe Asn Arg His Cys Ile
            1060                1065                1070
Glu Arg Gly Arg Lys Ala Glu Arg Ala Ala Asn Glu Leu Arg Ile Ala
        1075                1080                1085
```

-continued

```
Gly Asp Ala Asn Trp Gln Arg Arg Leu Leu Cys Pro Asp Pro Asn Asn
    1090                1095                1100
Leu Gly Gln Glu Gly Ile Cys Asp Ser Lys Leu Ser Ala Tyr Asn Ala
1105                1110                1115                1120
Asp Ser Trp Ala Leu Val Val Leu Gly Gly Tyr Tyr Thr Lys Ile Cys
                1125                1130                1135
Gly Arg Gln Ile Pro Leu Pro Glu Glu Ser Ala Ser Ser Ala Asp Asp
            1140                1145                1150
Ser Ser Cys Pro Ala Tyr Asp Asp Ser Tyr Asp Ala Asp Thr Val
        1155                1160                1165
Tyr Gly Val Asn Asp Tyr Val His Phe Gly Asp Ser Tyr Ala Ala Gly
    1170                1175                1180
Met Gly Thr Gly Thr Thr Thr Gly Asp Ser Cys Arg Val Gly Ser Asn
1185                1190                1195                1200
Ser Tyr Gly Lys Leu Val Gln Glu Trp Phe Asp Thr Glu Asp Phe Thr
                1205                1210                1215
Tyr Thr Asn Tyr Ala Cys Ser Gly Asp Thr Thr Val Gly Leu Asn Lys
            1220                1225                1230
Lys Ile Asp Gln Trp Leu Gly Gln Asp Pro Thr Gly Thr Thr Met Ala
        1235                1240                1245
Thr Leu Thr Ile Gly Gly Asn Asp Val Phe Phe Ser Asp Leu Val Ser
    1250                1255                1260
Asn Cys Val Leu Thr Met Trp Trp Tyr Ser Leu Glu Gln Tyr Arg Gln
1265                1270                1275                1280
Trp Cys Leu Glu Thr Glu Glu Lys Ala Arg Asn Leu Met Gln Asp Thr
                1285                1290                1295
Gly Ser Asp Gly Leu Gly Ser Lys Leu Arg Ala Ala Tyr Glu Lys Ile
            1300                1305                1310
Leu Asp Arg Ser Gly Ser Ser Val Tyr Leu Pro Val Ile Leu Ile Tyr
        1315                1320                1325
Ser Cys Arg Ala Val Leu Arg Arg Ala Asp Phe Thr Leu Val Val Gln
    1330                1335                1340
Pro Leu Arg Pro Trp Leu Cys His Leu Leu Gln Arg Arg His His Arg
1345                1350                1355                1360
Leu Arg Leu Asn His Leu Leu Glu Leu Asn Asp Leu Val Arg Met Leu
                1365                1370                1375
Asn Ser Leu Ile Gln Ser Thr Ile Ser Asp Ile Asn Thr Ala Arg Asn
            1380                1385                1390
Thr Glu Gln Ile His Tyr Ile Asp Met Asp Ala Arg Phe Asp Gly His
        1395                1400                1405
Arg Trp Cys Glu Pro Gly Thr Gln Glu Pro Asp Pro Asp Asn Pro Asn
    1410                1415                1420
Thr Tyr Phe Phe Leu Ser Ala Trp Pro Asp Ile Ala Ile Val Gly Asp
1425                1430                1435                1440
Thr Thr Ala Glu Ser Thr Asn Ala Thr Glu Thr Asp Glu Ile Thr Ala
                1445                1450                1455
Leu Met Asn Ser Gly Ser Ile Gln Leu Pro Asp Ala Asp Thr Cys Gln
            1460                1465                1470
Asp Ala Leu Gly Ser Asp Pro Asp Pro Tyr Ala Val Phe Met Cys Asp
        1475                1480                1485
Val Ala Val His Val Lys Ala Asn Ser Ser Ser Leu Ile Ala Gln Ser
    1490                1495                1500
Leu Asp Arg Ala Asn Gln Ala Ile Ala Asn Arg Asp Tyr Ser Ser Gln
```

```
                1505            1510            1515            1520
Asp Val Ser Trp Trp Leu Pro Ser Pro
                        1525

<210> SEQ ID NO 2
<211> LENGTH: 328
<212> TYPE: PRT
<213> ORGANISM: Aspergillus terreus

<400> SEQUENCE: 2

Met Thr Leu Pro Thr Leu Pro Asn Trp Ile Arg Met Cys Val His Leu
 1               5                  10                  15

Ser Leu Thr His Leu His Gln His Arg Ser Pro Lys Tyr Glu Ser Ile
            20                  25                  30

Pro Ile Lys Ser Ile Gln Ala Asn Ser His Arg Ile Leu Ile Ile Leu
        35                  40                  45

Thr Thr Ala Ser Phe Tyr Pro Gln Ile Arg Cys Ile Gln Leu Arg Asn
    50                  55                  60

Ser Thr His Gly Ile Ser Thr Ala Tyr Ile Leu Phe Asn Leu Ile Ser
65                  70                  75                  80

Ala Thr Glu His Phe Thr Ile Leu Phe Ala Leu Leu Val Asn Ser Gly
                85                  90                  95

Gly Asp Val Leu Ile His Glu Pro Pro Thr Thr Gly Asp Gly Leu Asn
            100                 105                 110

Leu Tyr Gln Leu Phe Ala Val Trp Met Gly Cys Leu Val Leu Phe Cys
        115                 120                 125

Gln Ala Ile His Ser Leu His Ala Asn Pro Arg Arg Lys Leu Ile Leu
    130                 135                 140

Leu Thr Ile Tyr Ile Gln Tyr Leu Cys Ile Ser Ile Leu Pro Glu Val
145                 150                 155                 160

Ile Asp Ala Ile Thr Thr Pro Glu Glu Thr Arg Lys Gln Arg Pro Pro
                165                 170                 175

Thr Gly Glu Arg Asn Trp Leu Ile Gly Leu Phe Leu Ser Ala His Ala
            180                 185                 190

Met Thr Val Leu Pro Leu Ser Ala Val Leu Arg Ile Ala Gly Phe Ile
        195                 200                 205

Asp Gln Ser Arg Leu Ile Ser Arg Arg Arg Glu Gln Pro Ser Val
    210                 215                 220

Leu Ser Leu Thr Gly Leu Ala Cys Gln Ala Val Val Phe Ala Leu Val
225                 230                 235                 240

Ser Gly Leu Trp Val Leu Arg Val Gln Gln Pro Val Pro Arg Met Pro
                245                 250                 255

Met Arg Arg Pro Val Asp Trp Met Tyr Trp Tyr His Val Ile Gly Trp
            260                 265                 270

Pro Val Val Asp Asp Ala Val Tyr Ala Leu Gly Gln Trp Val Leu Phe
        275                 280                 285

Trp Tyr Ala Val Cys Trp Arg Ser Arg Gly Asp Ala Arg Asp Glu Ala
    290                 295                 300

Val His Ala Gly Glu Thr Asp Asp Leu Leu Gly Glu Asp Glu Gly His
305                 310                 315                 320

Gly Tyr Gly Gly Thr Gly Thr Ser
                325

<210> SEQ ID NO 3
<211> LENGTH: 323
```

```
<212> TYPE: PRT
<213> ORGANISM: Aspergillus terreus

<400> SEQUENCE: 3

Met Val Gly Ser Lys Leu Ala His Asn Glu Glu Trp Leu Asp Ile Ala
1               5                   10                  15

Lys His His Ala Val Thr Met Ala Ile Gln Ala Arg Gln Leu Arg Leu
            20                  25                  30

Trp Pro Val Ile Leu Arg Pro Leu Val His Trp Leu Glu Pro Gln Gly
        35                  40                  45

Ala Lys Leu Arg Ala Gln Val Arg Arg Ala Arg Gln Leu Leu Asp Pro
    50                  55                  60

Ile Ile Gln Glu Arg Arg Ala Glu Arg Asp Ala Cys Arg Ala Lys Gly
65                  70                  75                  80

Ile Glu Pro Pro Arg Tyr Val Asp Ser Ile Gln Trp Phe Glu Asp Thr
                85                  90                  95

Ala Lys Gly Lys Trp Tyr Asp Ala Ala Gly Ala Gln Leu Ala Met Asp
            100                 105                 110

Phe Ala Gly Ile Tyr Gly Thr Ser Asp Leu Leu Ile Gly Gly Leu Val
        115                 120                 125

Asp Ile Val Arg His Pro His Leu Leu Glu Pro Leu Arg Asp Glu Ile
130                 135                 140

Arg Thr Val Ile Gly Gln Gly Gly Trp Thr Pro Ala Ser Leu Tyr Lys
145                 150                 155                 160

Leu Lys Leu Leu Asp Ser Cys Leu Lys Glu Ser Gln Arg Val Lys Pro
                165                 170                 175

Val Glu Cys Ala Thr Met Arg Ser Tyr Ala Leu Gln Asp Val Thr Phe
            180                 185                 190

Ser Asn Gly Thr Phe Ile Pro Lys Gly Glu Leu Val Ala Val Ala Ala
        195                 200                 205

Asp Arg Met Ser Asn Pro Glu Val Trp Pro Glu Pro Ala Lys Tyr Asp
210                 215                 220

Pro Tyr Arg Tyr Met Arg Leu Arg Glu Asp Pro Ala Lys Ala Phe Ser
225                 230                 235                 240

Ala Gln Leu Glu Asn Thr Asn Gly Asp His Ile Gly Phe Gly Trp His
                245                 250                 255

Pro Arg Ala Cys Pro Gly Arg Phe Phe Ala Ser Lys Glu Ile Lys Met
            260                 265                 270

Met Leu Ala Tyr Leu Leu Ile Arg Tyr Asp Trp Lys Val Val Pro Asp
        275                 280                 285

Glu Pro Leu Gln Tyr Tyr Arg His Ser Phe Ser Val Arg Ile His Pro
    290                 295                 300

Thr Thr Lys Leu Met Met Arg Arg Arg Asp Glu Asp Ile Arg Leu Pro
305                 310                 315                 320

Gly Ser Leu

<210> SEQ ID NO 4
<211> LENGTH: 256
<212> TYPE: PRT
<213> ORGANISM: Aspergillus terreus

<400> SEQUENCE: 4

Met Arg Tyr Gln Ala Ser Pro Ala Leu Val Lys Ala Pro Arg Ala Leu
1               5                   10                  15

Leu Cys Ile His Gly Ala Gly Cys Ser Pro Ala Ile Phe Arg Val Gln
```

```
                20                  25                  30
Leu Ser Lys Leu Arg Ala Ala Leu Arg Glu Asn Phe Glu Phe Val Tyr
            35                  40                  45
Val Thr Ala Pro Phe Pro Ser Ser Ala Gly Pro Gly Ile Leu Pro Val
 50                  55                  60
Phe Ala Asp Leu Gly Pro Tyr Tyr Ser Trp Phe Glu Ser Ser Ser Asp
 65                  70                  75                  80
Asn Asn His Asn Gly Pro Ser Val Ser Glu Arg Leu Ala Ala Val His
                85                  90                  95
Asp Pro Ile Arg Arg Thr Ile Val Asp Trp Gln Thr Gln His Pro His
               100                 105                 110
Ile Pro Ile Val Gly Ala Ile Gly Phe Ser Glu Gly Ala Leu Val Thr
               115                 120                 125
Thr Leu Leu Leu Trp Gln Gln Gln Met Gly His Leu Pro Trp Leu Pro
           130                 135                 140
Arg Met Ser Val Ala Leu Leu Ile Cys Pro Trp Tyr Gln Asp Glu Ala
145                 150                 155                 160
Ser Gln Tyr Met Arg Asn Glu Val Met Lys Asn His Asp Asp Asp Asn
               165                 170                 175
Asp Ser Lys Asp Thr Glu Trp Gln Glu Glu Leu Val Ile Arg Ile Pro
           180                 185                 190
Thr Leu His Leu Gln Gly Arg Asp Asp Phe Ala Leu Ala Gly Ser Lys
           195                 200                 205
Met Leu Val Ala Arg His Phe Ser Pro Arg Glu Ala Gln Val Leu Glu
    210                 215                 220
Phe Ala Gly Gln His Gln Phe Pro Asn Arg Pro Arg Asp Val Leu Glu
225                 230                 235                 240
Val Ile Asn Arg Phe Arg Lys Leu Cys Val Thr Ala Gln Thr Leu Glu
               245                 250                 255

<210> SEQ ID NO 5
<211> LENGTH: 363
<212> TYPE: PRT
<213> ORGANISM: Aspergillus terreus

<400> SEQUENCE: 5

Met Gly Asp Gln Pro Phe Ile Pro Pro Gln Gln Thr Ala Leu Thr
  1               5                  10                  15
Val Asn Asp His Asp Glu Val Thr Val Trp Asn Ala Ala Pro Cys Pro
             20                  25                  30
Met Leu Pro Arg Asp Gln Val Tyr Val Arg Val Glu Ala Val Ala Ile
         35                  40                  45
Asn Pro Ser Asp Thr Lys Met Arg Gly Gln Phe Ala Thr Pro Trp Ala
     50                  55                  60
Phe Leu Gly Thr Asp Tyr Ala Gly Thr Val Val Ala Val Gly Ser Asp
 65                  70                  75                  80
Val Thr His Ile Gln Val Gly Asp Arg Val Tyr Gly Ala Gln Asn Glu
                 85                  90                  95
Met Cys Pro Arg Thr Pro Asp Gln Gly Ala Phe Ser Gln Tyr Thr Val
            100                 105                 110
Thr Arg Gly Arg Val Trp Ala Lys Ile Pro Lys Gly Leu Ser Phe Glu
        115                 120                 125
Gln Ala Ala Ala Leu Pro Ala Gly Ile Ser Thr Ala Gly Leu Ala Met
    130                 135                 140
```

-continued

```
Lys Leu Leu Gly Leu Pro Leu Pro Ser Pro Ser Ala Asp Gln Pro Pro
145                 150                 155                 160

Thr His Ser Lys Pro Val Tyr Leu Val Tyr Gly Gly Ser Thr Ala
                165                 170                 175

Thr Ala Thr Val Thr Met Gln Met Leu Arg Leu Ser Gly Tyr Ile Pro
            180                 185                 190

Ile Ala Thr Cys Ser Pro His Asn Phe Asp Leu Ala Lys Ser Arg Gly
            195                 200                 205

Ala Glu Glu Val Phe Asp Tyr Arg Ala Pro Asn Leu Ala Gln Thr Ile
210                 215                 220

Arg Thr Tyr Thr Lys Asn Asn Leu Arg Tyr Ala Leu Asp Cys Ile Thr
225                 230                 235                 240

Asn Val Glu Ser Thr Thr Phe Cys Phe Ala Ala Ile Gly Arg Ala Gly
                245                 250                 255

Gly His Tyr Val Ser Leu Asn Pro Phe Pro Glu His Ala Ala Thr Arg
                260                 265                 270

Lys Met Val Thr Thr Asp Trp Thr Leu Gly Pro Thr Ile Phe Gly Glu
            275                 280                 285

Gly Ser Thr Trp Pro Ala Pro Tyr Gly Arg Pro Gly Ser Glu Glu Glu
            290                 295                 300

Arg Gln Phe Gly Glu Asp Leu Trp Arg Ile Ala Gly Gln Leu Val Glu
305                 310                 315                 320

Asp Gly Arg Leu Val His His Pro Leu Arg Val Val Gln Gly Gly Phe
                325                 330                 335

Asp His Ile Lys Gln Gly Met Glu Leu Val Arg Lys Gly Glu Leu Ser
                340                 345                 350

Gly Glu Lys Leu Val Val Arg Leu Glu Gly Pro
            355                 360

<210> SEQ ID NO 6
<211> LENGTH: 413
<212> TYPE: PRT
<213> ORGANISM: Aspergillus terreus

<400> SEQUENCE: 6

Met Gly Ser Ile Ile Asp Ala Ala Ala Ala Asp Pro Val Val Leu
  1                 5                  10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
        35                  40                  45

Cys Phe Gly Ala Arg Thr Val Arg Arg Asp Glu Cys Asn Gly Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Ala Arg Leu Arg Glu Arg
        115                 120                 125

Arg Gly Lys Ile Thr Leu Arg His Leu Thr His Thr Ser Gly Leu
    130                 135                 140

Ser Tyr Val Phe Leu His Pro Leu Leu Arg Glu Tyr Met Ala Gln Gly
145                 150                 155                 160
```

His Leu Gln Ser Ala Glu Lys Phe Gly Ile Glx Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
            195                 200                 205

Gln Tyr Leu Gln Glu Asn Ile Cys Ala Pro Leu Gly Ile Thr Asp Met
            210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
            245                 250                 255

Val Tyr Phe Arg Ala Asp Gly Glu Glu Cys Phe Gly Gly Gln Gly Val
            260                 265                 270

Phe Ser Gly Pro Gly Ser Tyr Met Lys Val Leu His Ser Leu Leu Lys
            275                 280                 285

Arg Asp Gly Leu Leu Leu Gln Pro Gln Thr Val Asp Leu Met Phe Gln
            290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
            325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Leu Thr Phe Gly Gly Gly Pro Asn
            355                 360                 365

Ile Val Trp Gln Ile Asp Pro Lys Ala Gly Leu Cys Thr Leu Ala Phe
370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
            405                 410

<210> SEQ ID NO 7
<211> LENGTH: 1068
<212> TYPE: PRT
<213> ORGANISM: Aspergillus terreus

<400> SEQUENCE: 7

Met Asp Pro Val Val Arg Lys Pro Asp Pro Gly Gly Val Gln His Arg
 1               5                  10                  15

Val Thr Lys Ala Leu Arg Ala Ile Val Gly His Ala Cys Arg His Pro
            20                  25                  30

Ile His Thr Leu Leu Val Thr Ala Leu Thr Ala Ala Thr Thr His Leu
        35                  40                  45

His Val Leu Glu Gly Thr Tyr Gln Ala Thr His Arg Glu Ala Ser Ala
    50                  55                  60

Trp Lys Trp Gln Ile Asp Asp Arg Pro Lys Val Pro Glu Asp Gly Gln
65                  70                  75                  80

Ser Asp Phe His Trp Ala Leu Val Thr Leu Asp Leu Pro Gly Ala Ser
            85                  90                  95

Val Asp Ala Ser Ile Pro Phe Ser Asn Thr Leu Ser Gly Phe Leu
            100                 105                 110

Gly Ala Glu Gln Thr Thr Pro Thr Pro Asp Ser Ser Pro Ser Pro Asp

```
            115                 120                 125
His Ser Ala Leu Thr Phe Arg Val Pro Tyr S er Gln Leu Asp Gly Phe
    130                 135                 140

Leu Gln Ala Val Glu Ile Ile Pro Ser Glu L ys Glu Asp Asp Ser Trp
145                 150                 155                 160

Arg Leu Arg Ser Pro Arg Glu Glu Gly Ser P ro Arg Ser Leu Gly His
                165                 170                 175

Trp Leu Gly Ser Ser Trp Leu Ser Phe Leu H is Arg Val His His Ala
                180                 185                 190

Glu Thr Val Asp Leu Val Ile Ile Gly Leu S er Tyr Leu Ala Met Asn
                195                 200                 205

Met Thr Val Val Ser Leu Phe Arg Val Met A rg His Leu Gly Ser Arg
    210                 215                 220

Phe Trp Leu Ala Ala Ser Val Leu Leu Ser G ly Ala Phe Ala Phe Val
225                 230                 235                 240

Leu Gly Leu Gly Ile Thr Thr Cys Asp V al Pro Val Asp Met Leu
                245                 250                 255

Leu Leu Phe Glu Gly Ile Pro Tyr Leu Val L eu Thr Val Gly Phe Glu
                260                 265                 270

Lys Pro Ile Gln Leu Thr Arg Ala Val Leu C ys Val Ser Glu Glu Leu
                275                 280                 285

Trp Gly Gly Gly Gln Arg Gln Val Pro Asn G ly Ala Ser Ser Asp Asp
290                 295                 300

Ser Arg Gln Asn Gln Leu Ile Pro Asn Ile I le Gln Leu Ala Val Asp
305                 310                 315                 320

Arg Glu Gly Trp Tyr Ile Val Arg Ser Tyr L eu Leu Glu Ile Gly Ala
                325                 330                 335

Leu Ala Leu Gly Ala Val Leu Arg Pro Lys A sp Ser Leu Gly His Phe
                340                 345                 350

Cys Phe Leu Ala Ala Trp Thr Leu Leu Ile A sp Ala Val Leu Leu Phe
                355                 360                 365

Thr Phe Tyr Ala Thr Ile Leu Cys Val Lys L eu Glu Ile Thr Arg Ile
                370                 375                 380

Arg Ser Pro Gly Gly Leu Gly Gln Val Asn A la Lys His Pro Ser Gly
385                 390                 395                 400

Ile Phe Gly His Lys Val Lys Ser Thr Asn I le Thr Trp Trp Lys Leu
                405                 410                 415

Leu Thr Val Gly Gly Phe Val Leu Cys His P he Leu Gln Leu Ser Pro
                420                 425                 430

Phe Phe Tyr Arg Val Met Gly Glu Tyr Met A la Asn Gly Thr Leu Pro
                435                 440                 445

Pro Thr Ala Val Ser Pro Phe Lys Glu Ala A la Asn Gly Leu Asn Glu
    450                 455                 460

Ile Tyr Leu Thr Ala Arg Val Glu Gly Phe G lu Thr Arg Val Thr Val
465                 470                 475                 480

Leu Pro Pro Leu Gln Tyr Val Leu Glu Ser A la Gly Phe Asn Ile Ser
                485                 490                 495

Ala Thr Lys Arg Ser Thr Phe Asp Gly Val L eu Asp Gly Leu Glu Ser
                500                 505                 510

Pro Leu Gly Arg Leu Cys Leu Met Gly Ala L eu Val Val Ser Leu Val
                515                 520                 525

Leu Asn Asn His Leu Ile His Ala Ala Arg T rp His Ala Trp Pro Gln
    530                 535                 540
```

-continued

```
Ala Arg Glu Ser Ala Val Pro Asp Gly Ser T yr Leu Ser Val Pro Cys
545                 550                 555                 560

Ser Ala Thr Ala Pro Glu Val Cys Thr Arg P ro Pro Glu Thr Glu
                565                 570                 575

Ala Leu Leu Lys Ser Asn Gln Ala Glu Ser L eu Thr Asp Asp Glu Leu
                580                 585                 590

Val Glu Leu Cys Leu Arg Gly Lys Ile Ala G ly Tyr Ser Leu Glu Lys
            595                 600                 605

Thr Leu Glu Arg Ile Ala Ala Gly Ser Ser A rg Ser Val Thr Arg Leu
        610                 615                 620

Glu Ala Phe Thr Arg Ala Val Arg Ile Arg A rg Ala Ala Val Ser Lys
625                 630                 635                 640

Thr Pro Ser Thr Gln Asn Leu Cys Ser Gly L eu Ala Glu Ser Leu Leu
                645                 650                 655

Pro Tyr Arg Asp Tyr Asn Tyr Glu Leu Val H is Gly Ala Cys Cys Glu
                660                 665                 670

Asn Val Val Gly Tyr Leu Pro Leu Pro Leu G ly Val Ala Gly Pro Met
            675                 680                 685

Val Ile Asp Gly Gln Ala Leu Phe Ile Pro M et Ala Thr Thr Glu Gly
        690                 695                 700

Val Leu Val Ala Ser Ala Ser Arg Gly Cys L ys Ala Ile Asn Ala Gly
705                 710                 715                 720

Gly Gly Ala Thr Thr Met Leu Lys Gly Asp G ly Met Thr Arg Gly Pro
                725                 730                 735

Cys Leu Arg Phe Pro Ser Ala Gln Arg Ala A la Glu Ala Gln Arg Trp
            740                 745                 750

Val Glu Ser Pro Leu Gly His Glu Val Leu A la Ala Ala Phe Asn Ala
        755                 760                 765

Thr Ser Arg Phe Ala Arg Leu Gln Thr Leu T hr Val Ala Gln Ala Gly
        770                 775                 780

Ile Tyr Leu Tyr Ile Arg Phe Arg Thr Thr T hr Gly Asp Ala Met Gly
785                 790                 795                 800

Met Asn Met Ile Ser Lys Gly Val Glu Lys A la Leu Glu Ala Met Ala
                805                 810                 815

Ala Glu Gly Gly Phe Pro Asp Met His Thr V al Thr Leu Ser Gly Asn
                820                 825                 830

Phe Cys Ser Asp Lys Lys Ser Ala Ala Ile A sn Trp Ile Gly Gly Arg
            835                 840                 845

Gly Lys Ser Val Ile Ala Glu Ala Thr Ile P ro Ala Glu Thr Val Arg
        850                 855                 860

Gln Val Leu Lys Thr Asp Val Asp Ala Leu V al Glu Leu Asn Thr Ala
865                 870                 875                 880

Lys Asn Leu Val Gly Ser Ala Met Ala Gly S er Leu Gly Gly Phe Asn
                885                 890                 895

Ala His Ala Ser Asn Leu Val Gln Ala Val P he Leu Ala Thr Gly Gln
                900                 905                 910

Asp Pro Ala Gln Asn Val Glu Ser Ser Ser C ys Ile Thr Thr Met Lys
            915                 920                 925

Asn Ile Asp Gly Asn Leu His Ile Ala Val S er Met Pro Ser Met Glu
        930                 935                 940

Val Gly Thr Ile Gly Gly Gly Thr Ile Leu G lu Ala Gln Gly Ala Met
945                 950                 955                 960
```

-continued

```
Leu Asp Leu Leu Gly Val Arg Gly Ala His Ser Thr Glu Pro Gly Ala
                965                 970                 975
Asn Ala Arg Arg Leu Ala Arg Ile Val Ala Ala Ala Val Leu Ala Gly
            980                 985                 990
Glu Leu Ser Thr Cys Ala Ala Leu Ala Ala Gly His Leu Val Asn Ala
        995                1000                1005
His Met Gln His Asn Arg Thr Ser Lys Asp Ala Ile Ser Gly Thr Glu
    1010                1015                1020
Tyr Gly Ala Ile Arg Thr Pro Val Tyr Val Ile Leu Glu His Ala
1025                1030                1035                1040
Gly Asp Ile His Phe Val Gln Ile Glu Tyr Lys Asn Thr Tyr Leu Arg
                1045                1050                1055
Arg Lys Val Pro Thr Leu Ser Cys Asn Leu Gly Arg
                1060                1065

<210> SEQ ID NO 8
<211> LENGTH: 503
<212> TYPE: PRT
<213> ORGANISM: Aspergillus terreus

<400> SEQUENCE: 8

Met Ala Ala Asp Gln Gly Ile Phe Thr Asn Ser Val Thr Leu Ser Pro
  1                 5                  10                  15
Val Glu Gly Ser Arg Thr Gly Gly Thr Leu Pro Arg Arg Ala Phe Arg
             20                  25                  30
Arg Ser Cys Asp Arg Cys His Ala Gln Lys Ile Lys Cys Thr Gly Asn
         35                  40                  45
Lys Glu Val Thr Gly Arg Ala Pro Cys Gln Arg Cys Gln Gln Ala Gly
 50                  55                  60
Leu Arg Cys Val Tyr Ser Glu Arg Cys Pro Lys Arg Lys Leu Arg Gln
 65                  70                  75                  80
Ser Arg Ala Ala Asp Leu Val Ser Ala Asp Pro Asp Pro Cys Leu His
                 85                  90                  95
Met Ser Ser Pro Pro Val Pro Ser Gln Ser Leu Pro Leu Asp Val Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Thr Asp Glu Ala Ile Asp
    130                 135                 140
Thr Asp Cys Trp Gly Leu Ser Gln Cys Asp Gly Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
            180                 185                 190
Ser Ala Gln Arg Glu Leu Phe Asp Asp Leu Ser Ala Val Ser Gln Glu
        195                 200                 205
Leu Glu Glu Ile Leu Leu Ala Val Thr Val Glu Trp Pro Lys Gln Glu
    210                 215                 220
Ile Trp Thr Arg Ala Ser Pro His Ser Pro Thr Ala Ser Arg Glu Arg
225                 230                 235                 240
Ile Ala Gln Arg Arg Gln Asn Val Trp Ala Asn Trp Leu Thr Asp Leu
                245                 250                 255
His Met Phe Ser Leu Asp Pro Ile Gly Met Phe Phe Asn Ala Ser Arg
            260                 265                 270
```

-continued

```
Arg Leu Leu Thr Val Leu Arg Gln Gln Ala Gln Ala Asp Cys His Gln
            275                 280                 285

Gly Thr Leu Asp Glu Cys Leu Arg Thr Lys Asn Leu Phe Thr Ala Val
        290                 295                 300

His Cys Tyr Ile Leu Asn Val Arg Ile Leu Thr Ala Ile Ser Glu Leu
305                 310                 315                 320

Leu Leu Ser Gln Ile Arg Arg Thr Gln Asn Ser His Met Ser Pro Leu
                325                 330                 335

Glu Gly Ser Arg Ser Gln Ser Pro Ser Arg Asp Asp Thr Ser Ser Ser
            340                 345                 350

Ser Gly His Ser Ser Val Asp Thr Ile Pro Phe Phe Ser Glu Asn Leu
        355                 360                 365

Pro Ile Gly Glu Leu Phe Ser Tyr Val Asp Pro Leu Thr His Ala Leu
    370                 375                 380

Phe Ser Ala Cys Thr Thr Leu His Val Gly Val Gln Leu Leu Arg Glu
385                 390                 395                 400

Asn Glu Ile Thr Leu Gly Val His Ser Ala Gln Gly Ile Ala Ala Ser
                405                 410                 415

Ile Ser Met Ser Gly Glu Pro Gly Glu Asp Ile Ala Arg Thr Gly Ala
            420                 425                 430

Thr Asn Ser Ala Arg Cys Glu Gln Pro Thr Thr Pro Ala Ala Arg
        435                 440                 445

Val Leu Phe Met Phe Leu Ser Asp Glu Gly Ala Phe Gln Glu Ala Lys
    450                 455                 460

Ser Ala Gly Ser Arg Gly Arg Thr Ile Ala Ala Leu Arg Arg Cys Tyr
465                 470                 475                 480

Glu Asp Ile Phe Ser Leu Ala Arg Lys His Lys His Gly Met Leu Arg
                485                 490                 495

Asp Leu Asn Asn Ile Pro Pro
            500
```

<210> SEQ ID NO 9
<211> LENGTH: 542
<212> TYPE: PRT
<213> ORGANISM: Aspergillus terreus

<400> SEQUENCE: 9

```
Met Thr Ser His His Gly Glu Thr Glu Lys Pro Gln Ser Asn Thr Ala
  1               5                  10                  15

Gln Met Gln Ile Asn His Val Thr Gly Leu Arg Leu Gly Leu Val Val
                20                  25                  30

Val Ser Val Thr Leu Val Ala Phe Leu Met Leu Leu Asp Met Ser Ile
            35                  40                  45

Ile Val Thr Ala Ile Pro His Ile Thr Ala Gln Phe His Ser Leu Gly
        50                  55                  60

Asp Val Gly Trp Tyr Gly Ser Ala Tyr Leu Leu Ser Ser Cys Ala Leu
 65                  70                  75                  80

Gln Pro Leu Ala Gly Lys Leu Tyr Thr Leu Leu Thr Leu Lys Tyr Thr
                85                  90                  95

Phe Leu Ala Phe Leu Gly Leu Phe Glu Ile Gly Ser Val Leu Cys Gly
            100                 105                 110

Thr Ala Arg Ser Ser Thr Met Leu Ile Val Gly Arg Ala Val Ala Gly
        115                 120                 125

Met Gly Gly Ser Gly Leu Thr Asn Gly Ala Ile Thr Ile Leu Ser Ala
```

```
            130             135             140
Ala Ala Pro Lys Gln Gln Pro Leu Leu Ile Gly Ile Met Met Gly
145             150                 155             160

Leu Ser Gln Ile Ala Ile Val Cys Gly Pro Leu Leu Gly Gly Ala Phe
                165             170              175

Thr Gln His Ala Ser Trp Arg Trp Cys Phe Tyr Ile Asn Leu Pro Ile
            180             185             190

Gly Ala Phe Ala Thr Phe Leu Leu Val Ile Gln Ile Pro Asn Arg
            195             200         205

Leu Pro Ser Thr Ser Asp Ser Thr Asp Gly Thr Asn Pro Lys Arg
            210             215             220

Arg Gly Ala Arg Asp Val Leu Thr Gln Leu Asp Phe Leu Gly Phe Val
225             230             235             240

Leu Phe Ala Gly Phe Ala Ile Met Ile Ser Leu Ala Leu Glu Trp Gly
                245             250             255

Gly Ser Asp Tyr Ala Trp Asn Ser Ser Val Ile Ile Gly Leu Phe Cys
                260             265             270

Ala Ala Gly Val Ser Leu Val Leu Phe Gly Cys Trp Glu Arg His Val
            275             280             285

Gly Gly Ala Val Ala Met Ile Pro Ile Ser Val Ala Ser Arg Arg Gln
            290             295             300

Val Trp Cys Ser Cys Phe Phe Leu Gly Phe Phe Ser Gly Ala Leu Leu
305             310             315             320

Ile Phe Ser Tyr Tyr Leu Pro Ile Tyr Phe Gln Ala Val Lys Asn Val
                325             330             335

Ser Pro Thr Met Ser Gly Val Tyr Met Leu Pro Gly Ile Gly Gly Gln
            340             345             350

Ile Val Met Ala Ile Val Thr Gly Ala Ile Ile Gly Lys Thr Gly Tyr
            355             360             365

Tyr Val Pro Trp Ala Leu Ala Ser Gly Ile Leu Val Ser Ile Ser Ala
370             375             380

Gly Leu Val Ser Thr Phe Gln Pro Glu Thr Ser Ile Ala Ala Trp Val
385             390             395             400

Met Tyr Gln Phe Leu Gly Gly Val Gly Arg Gly Cys Gly Met Gln Thr
                405             410             415

Pro Val Val Ala Ile Gln Asn Ala Leu Pro Pro Gln Thr Ser Pro Ile
            420             425             430

Gly Ile Ser Leu Ala Met Phe Gly Gln Thr Phe Gly Gly Ser Leu Phe
            435             440             445

Leu Thr Leu Thr Glu Leu Val Phe Ser Asn Gly Leu Asp Ser Gly Leu
450             455             460

Arg Gln Tyr Ala Pro Thr Leu Asn Ala Gln Glu Val Thr Ala Ala Gly
465             470             475             480

Ala Thr Gly Phe Arg Gln Val Pro Ala Pro Leu Ile Ser Arg Val
                485             490             495

Leu Leu Ala Tyr Ser Lys Gly Val Asp His Ala Phe Tyr Val Ala Val
            500             505             510

Gly Ala Ser Gly Ala Thr Phe Ile Phe Ala Trp Gly Met Gly Arg Leu
            515             520             525

Ala Trp Arg Gly Trp Arg Met Gln Glu Lys Gly Arg Ser Glu
    530             535             540
```

<210> SEQ ID NO 10

```
<211> LENGTH: 2532
<212> TYPE: PRT
<213> ORGANISM: Aspergillus terreus

<400> SEQUENCE: 10
```

| | | | | | | | | | | | | | | |
|---|---|---|---|---|---|---|---|---|---|---|---|---|---|---|
|Met|Thr|Pro|Leu|Asp|Ala|Pro|Gly|Ala|Pro|Ala|Pro|Ile|Ala|Met|Val|
|1| | | |5| | | |10| | | | |15| |
|Gly|Met|Gly|Cys|Arg|Phe|Gly|Gly|Ala|Thr|Asp|Pro|Gln|Lys|Leu|
| | | |20| | | | |25| | | | |30| |
|Trp|Lys|Leu|Leu|Glu|Glu|Gly|Gly|Ser|Ala|Trp|Ser|Lys|Ile|Pro|Pro|
| | |35| | | | |40| | | | |45| | |
|Ser|Arg|Phe|Asn|Val|Gly|Gly|Val|Tyr|His|Pro|Asn|Gly|Gln|Arg|Val|
| |50| | | | |55| | | | |60| | | | |
|Gly|Ser|Met|His|Val|Arg|Gly|Gly|His|Phe|Leu|Asp|Glu|Asp|Pro|Ala|
|65| | | | |70| | | | |75| | | | |80|
|Leu|Phe|Asp|Ala|Ser|Phe|Phe|Asn|Met|Ser|Thr|Glu|Val|Ala|Ser|Cys|
| | | | |85| | | | |90| | | | |95| |
|Met|Asp|Pro|Gln|Tyr|Arg|Leu|Ile|Leu|Glu|Val|Val|Tyr|Glu|Ala|Leu|
| | | |100| | | | |105| | | | |110| | |
|Glu|Ala|Ala|Gly|Ile|Pro|Leu|Glu|Gln|Val|Ser|Gly|Ser|Lys|Thr|Gly|
| | |115| | | | |120| | | | |125| | | |
|Val|Phe|Ala|Gly|Thr|Met|Tyr|His|Asp|Tyr|Gln|Gly|Ser|Phe|Gln|Arg|
| |130| | | | |135| | | | |140| | | | |
|Gln|Pro|Glu|Ala|Leu|Pro|Arg|Tyr|Phe|Ile|Thr|Gly|Asn|Ala|Gly|Thr|
|145| | | | |150| | | | |155| | | | |160|
|Met|Leu|Ala|Asn|Arg|Val|Ser|His|Phe|Tyr|Asp|Leu|Arg|Gly|Pro|Ser|
| | | | |165| | | | |170| | | | |175| |
|Val|Ser|Ile|Asp|Thr|Ala|Cys|Ser|Thr|Thr|Leu|Thr|Ala|Leu|His|Leu|
| | | |180| | | | |185| | | | |190| | |
|Ala|Ile|Gln|Ser|Leu|Arg|Ala|Gly|Glu|Ser|Asp|Met|Ala|Ile|Val|Ala|
| | |195| | | | |200| | | | |205| | | |
|Gly|Ala|Asn|Leu|Leu|Leu|Asn|Pro|Asp|Val|Phe|Thr|Thr|Met|Ser|Asn|
| |210| | | | |215| | | | |220| | | | |
|Leu|Gly|Phe|Leu|Ser|Ser|Asp|Gly|Ile|Ser|Tyr|Ser|Phe|Asp|Ser|Arg|
|225| | | | |230| | | | |235| | | | |240|
|Ala|Asp|Gly|Tyr|Gly|Arg|Gly|Glu|Gly|Val|Ala|Ala|Ile|Val|Leu|Lys|
| | | | |245| | | | |250| | | | |255| |
|Thr|Leu|Pro|Asp|Ala|Val|Arg|Asp|Gly|Asp|Pro|Ile|Arg|Leu|Ile|Val|
| | | |260| | | | |265| | | | |270| | |
|Arg|Glu|Thr|Ala|Ile|Asn|Gln|Asp|Gly|Arg|Thr|Pro|Ala|Ile|Ser|Thr|
| | |275| | | | |280| | | | |285| | | |
|Pro|Ser|Gly|Glu|Ala|Gln|Glu|Cys|Leu|Ile|Gln|Asp|Cys|Tyr|Gln|Lys|
| |290| | | | |295| | | | |300| | | | |
|Ala|Gln|Leu|Asp|Pro|Lys|Gln|Thr|Ser|Tyr|Val|Glu|Ala|His|Gly|Thr|
|305| | | | |310| | | | |315| | | | |320|
|Gly|Thr|Arg|Ala|Gly|Asp|Pro|Leu|Glu|Leu|Ala|Val|Ile|Ser|Ala|Ala|
| | | | |325| | | | |330| | | | |335| |
|Phe|Pro|Gly|Gln|Gln|Ile|Gln|Val|Gly|Ser|Val|Lys|Ala|Asn|Ile|Gly|
| | | |340| | | | |345| | | | |350| | |
|His|Thr|Glu|Ala|Val|Ser|Gly|Leu|Ala|Ser|Leu|Ile|Lys|Val|Ala|Leu|
| | |355| | | | |360| | | | |365| | | |
|Ala|Val|Glu|Lys|Gly|Val|Ile|Pro|Pro|Asn|Ala|Arg|Phe|Leu|Gln|Pro|
| |370| | | | |375| | | | |380| | | | |
|Ser|Lys|Lys|Leu|Leu|Lys|Asp|Thr|His|Ile|Gln|Ile|Pro|Leu|Cys|Ser|

-continued

```
385                 390                 395                 400

Gln Ser Trp Ile Pro Thr Asp Gly Val Arg A rg Ala Ser Ile Asn Asn
                405                 410                 415

Phe Gly Phe Gly Gly Ala Asn Ala His Ala I le Val Glu Gln Tyr Gly
                420                 425                 430

Pro Phe Ala Glu Thr Ser Ile Cys Pro Pro A sn Gly Tyr Ser Gly Asn
                435                 440                 445

Tyr Asp Gly Asn Leu Gly Thr Asp Gln Ala H is Ile Tyr Val Leu Ser
450                 455                 460

Ala Lys Asp Glu Asn Ser Cys Met Arg Met V al Ser Arg Leu Cys Asp
465                 470                 475                 480

Tyr Ala Thr His Ala Arg Pro Ala Asp Asp L eu Gln Leu Leu Ala Asn
                485                 490                 495

Ile Ala Tyr Thr Leu Gly Ser Arg Arg Ser A sn Phe Arg Trp Lys Ala
                500                 505                 510

Val Cys Thr Ala His Ser Leu Thr Gly Leu A la Gln Asn Leu Ala Gly
                515                 520                 525

Glu Gly Met Arg Pro Ser Lys Ser Ala Asp G ln Val Arg Leu Gly Trp
                530                 535                 540

Val Phe Thr Gly Gln Gly Ala Gln Trp Phe A la Met Gly Arg Glu Leu
545                 550                 555                 560

Ile Glu Met Tyr Pro Val Phe Lys Glu Ala L eu Leu Glu Cys Asp Gly
                565                 570                 575

Tyr Ile Lys Glu Met Gly Ser Thr Trp Ser I le Ile Glu Glu Leu Ser
                580                 585                 590

Arg Pro Glu Thr Glu Ser Arg Val Asp Gln A la Glu Phe Ser Leu Pro
                595                 600                 605

Leu Ser Thr Ala Leu Gln Ile Ala Leu Val A rg Leu Leu Trp Ser Trp
                610                 615                 620

Asn Ile Gln Pro Val Ala Val Thr Ser His S er Ser Gly Glu Ala Ala
625                 630                 635                 640

Ala Ala Tyr Ala Ile Gly Ala Leu Thr Ala A rg Ser Ala Ile Gly Ile
                645                 650                 655

Ser Tyr Ile Arg Gly Ala Leu Thr Ala Arg A sp Arg Leu Ala Ser Val
                660                 665                 670

His Lys Gly Gly Met Leu Ala Val Gly Leu S er Arg Ser Glu Val Gly
                675                 680                 685

Ile Tyr Ile Arg Gln Val Pro Leu Gln Ser G lu Glu Cys Leu Val Val
                690                 695                 700

Gly Cys Val Asn Ser Pro Ser Val Thr V al Ser Gly Asp Leu Ser
705                 710                 715                 720

Ala Ile Ala Lys Leu Glu Glu Leu Leu His A la Asp Arg Ile Phe Ala
                725                 730                 735

Arg Arg Leu Lys Val Thr Gln Ala Phe His S er Ser His Met Asn Ser
                740                 745                 750

Met Thr Asp Ala Phe Arg Ala Gly Leu Thr G lu Leu Phe Gly Ala Asp
                755                 760                 765

Pro Ser Asp Ala Ala Asn Ala Ser Lys Asp V al Ile Tyr Ala Ser Pro
                770                 775                 780

Arg Thr Gly Ala Arg Leu His Asp Met Asn A rg Leu Arg Asp Pro Ile
785                 790                 795                 800

His Trp Val Glu Cys Met Leu His Pro Val G lu Phe Glu Ser Ala Phe
                805                 810                 815
```

```
Arg Arg Met Cys Leu Asp Glu Asn Asp His Met Pro Lys Val Asp Arg
            820                 825                 830

Val Ile Glu Ile Gly Pro His Gly Ala Leu Gly Gly Pro Ile Lys Gln
            835                 840                 845

Ile Met Gln Leu Pro Glu Leu Ala Thr Cys Asp Ile Pro Tyr Leu Ser
        850                 855                 860

Cys Leu Ser Arg Gly Lys Ser Ser Leu Ser Thr Leu Arg Leu Leu Ala
865                 870                 875                 880

Ser Glu Leu Ile Arg Ala Gly Phe Pro Val Asp Leu Asn Ala Ile Asn
                885                 890                 895

Phe Pro Arg Gly Cys Glu Ala Ala Arg Val Gln Val Leu Ser Asp Leu
            900                 905                 910

Pro Pro Tyr Pro Trp Asn His Glu Thr Arg Tyr Trp Lys Glu Pro Arg
        915                 920                 925

Ile Ser Gln Ser Ala Arg Gln Arg Lys Gly Pro Val His Asp Leu Ile
        930                 935                 940

Gly Leu Gln Glu Pro Leu Asn Leu Pro Leu Ala Arg Ser Trp His Asn
945                 950                 955                 960

Val Leu Arg Val Ser Asp Leu Pro Trp Leu Arg Asp His Val Val Gly
            965                 970                 975

Ser His Ile Val Phe Pro Gly Ala Gly Phe Val Cys Met Ala Val Met
            980                 985                 990

Gly Ile Ser Thr Leu Cys Ser Ser Asp His Glu Ser Asp Asp Ile Ser
            995                 1000                1005

Tyr Ile Leu Arg Asp Val Asn Phe Ala Gln Ala Leu Ile Leu Pro Ala
    1010                1015                1020

Asp Gly Glu Glu Gly Ile Asp Leu Arg Leu Thr Ile Cys Ala Pro Asp
1025                1030                1035                1040

Gln Ser Leu Gly Ser Gln Asp Trp Gln Arg Phe Leu Val His Ser Ile
            1045                1050                1055

Thr Ala Asp Lys Asn Asp Trp Thr Glu His Cys Thr Gly Leu Val Arg
        1060                1065                1070

Ala Glu Met Asp Gln Pro Pro Ser Ser Leu Ser Asn Gln Gln Arg Ile
    1075                1080                1085

Asp Pro Arg Pro Trp Ser Arg Lys Thr Ala Pro Gln Glu Leu Trp Asp
1090                1095                1100

Ser Leu His Arg Val Gly Ile Arg His Gly Pro Phe Phe Arg Asn Ile
1105                1110                1115                1120

Thr Cys Ile Glu Ser Asp Gly Arg Gly Ser Trp Cys Thr Phe Ala Ile
            1125                1130                1135

Ala Asp Thr Ala Ser Ala Met Pro His Ala Tyr Glu Ser Gln His Ile
        1140                1145                1150

Val His Pro Thr Thr Leu Asp Ser Ala Val Gln Ala Ala Tyr Thr Thr
    1155                1160                1165

Leu Pro Phe Ala Gly Ser Arg Ile Lys Ser Ala Met Val Pro Ala Arg
    1170                1175                1180

Val Gly Cys Met Lys Ile Ser Ser Arg Leu Ala Asp Leu Glu Ala Arg
1185                1190                1195                1200

Asp Met Leu Arg Ala Gln Ala Lys Met His Ser Gln Ser Pro Ser Ala
            1205                1210                1215

Leu Val Thr Asp Val Ala Val Phe Asp Glu Ala Asp Pro Val Gly Gly
    1220                1225                1230
```

```
Pro Val Met Glu Leu Glu Gly Leu Val Phe Gln Ser Leu Gly Ala Ser
    1235                1240                1245

Leu Gly Thr Ser Asp Arg Asp Ser Thr Asp Pro Gly Asn Thr Cys Ser
1250                1255                1260

Ser Trp His Trp Ala Pro Asp Ile Ser Leu Val Asn Pro Gly Trp Leu
1265                1270                1275                1280

Glu Lys Thr Leu Gly Thr Gly Ile Gln Glu His Glu Ile Ser Leu Ile
        1285                1290                1295

Leu Glu Leu Arg Arg Cys Ser Val His Phe Ile Gln Glu Ala Met Glu
        1300                1305                1310

Ser Leu Ser Val Gly Asp Val Glu Arg Leu Ser Gly His Leu Ala Lys
        1315                1320                1325

Phe Tyr Ala Trp Met Gln Lys Gln Leu Ala Cys Ala Gln Asn Gly Glu
        1330                1335                1340

Leu Gly Pro Glu Ser Ser Ser Trp Thr Arg Asp Ser Glu Gln Ala Arg
1345                1350                1355                1360

Cys Ser Leu Arg Ser Arg Val Val Ala Gly Ser Thr Asn Gly Glu Met
        1365                1370                1375

Ile Cys Arg Leu Gly Ser Val Leu Pro Ala Ile Leu Arg Arg Glu Val
        1380                1385                1390

Asp Pro Leu Glu Val Met Met Asp Gly His Leu Leu Ser Arg Tyr Tyr
        1395                1400                1405

Val Asp Ala Leu Lys Trp Ser Arg Ser Asn Ala Gln Ala Ser Glu Leu
    1410                1415                1420

Val Arg Leu Cys Cys His Lys Asn Pro Arg Ala Arg Ile Leu Glu Ile
1425                1430                1435                1440

Gly Gly Gly Thr Gly Gly Cys Thr Gln Leu Val Val Asp Ser Leu Gly
        1445                1450                1455

Pro Asn Pro Pro Val Gly Arg Tyr Asp Phe Thr Asp Val Ser Ala Gly
    1460                1465                1470

Phe Phe Glu Ala Ala Arg Lys Arg Phe Ala Gly Trp Gln Asn Val Met
    1475                1480                1485

Asp Phe Arg Lys Leu Asp Ile Glu Asp Asp Pro Glu Ala Gln Gly Phe
    1490                1495                1500

Val Cys Gly Ser Tyr Asp Val Val Leu Ala Cys Gln Val Leu His Ala
1505                1510                1515                1520

Thr Ser Asn Met Gln Arg Thr Leu Thr Asn Val Arg Lys Leu Leu Lys
        1525                1530                1535

Pro Gly Gly Lys Leu Ile Leu Val Glu Thr Thr Arg Asp Glu Leu Asp
        1540                1545                1550

Leu Phe Phe Thr Phe Gly Leu Leu Pro Gly Trp Trp Leu Ser Glu Glu
    1555                1560                1565

Pro Glu Arg Gln Ser Thr Pro Ser Leu Ser Pro Thr Met Trp Arg Ser
    1570                1575                1580

Met Leu His Thr Thr Gly Phe Asn Gly Val Glu Val Glu Ala Arg Asp
1585                1590                1595                1600

Cys Asp Ser His Glu Phe Tyr Met Ile Ser Thr Met Met Ser Thr Ala
        1605                1610                1615

Val Gln Ala Thr Pro Met Ser Cys Ser Val Lys Leu Pro Glu Val Leu
        1620                1625                1630

Leu Val Tyr Val Asp Ser Ser Thr Pro Met Ser Trp Ile Ser Asp Leu
    1635                1640                1645

Gln Gly Glu Ile Arg Gly Arg Asn Cys Ser Val Thr Ser Leu Gln Ala
```

-continued

```
            1650                1655                1660
Leu Arg Gln Val Pro Pro Thr Glu Gly Gln Ile Cys Val Phe Leu Gly
1665                1670                1675                1680
Glu Val Glu His Ser Met Leu Gly Ser Val Thr Asn Asp Asp Phe Thr
            1685                1690                1695
Leu Leu Thr Ser Met Leu Gln Leu Ala Gly Gly Thr Leu Trp Val Thr
            1700                1705                1710
Gln Gly Ala Thr Met Lys Ser Asp Asp Pro Leu Lys Ala Leu His Leu
            1715                1720                1725
Gly Leu Leu Arg Thr Met Arg Asn Glu Ser His Gly Lys Arg Phe Val
            1730                1735                1740
Ser Leu Asp Leu Asp Pro Ser Arg Asn Pro Trp Thr Gly Asp Ser Arg
1745                1750                1755                1760
Asp Ala Ile Val Ser Val Leu Asp Leu Ile Ser Met Ser Asp Glu Lys
            1765                1770                1775
Glu Phe Asp Tyr Ala Glu Arg Asp Gly Val Ile His Val Pro Arg Ala
            1780                1785                1790
Phe Ser Asp Ser Ile Asn Gly Gly Glu Glu Asp Gly Tyr Ala Leu Glu
            1795                1800                1805
Pro Phe Gln Asp Ser Gln His Leu Leu Arg Leu Asp Ile Gln Thr Pro
            1810                1815                1820
Gly Leu Leu Asp Ser Leu His Phe Thr Lys Arg Asn Val Asp Thr Tyr
1825                1830                1835                1840
Glu Pro Asp Lys Leu Pro Asp Asp Trp Val Glu Ile Glu Pro Arg Ala
            1845                1850                1855
Phe Gly Leu Asn Phe Arg Asp Ile Met Val Ala Met Gly Gln Leu Glu
            1860                1865                1870
Ser Asn Val Met Gly Phe Glu Cys Ala Gly Val Val Thr Ser Leu Ser
            1875                1880                1885
Glu Thr Ala Arg Thr Ile Ala Pro Gly Leu Ala Val Gly Asp Arg Val
            1890                1895                1900
Cys Ala Leu Met Asn Gly His Trp Ala Ser Arg Val Thr Thr Ser Arg
1905                1910                1915                1920
Thr Asn Val Val Arg Ile Pro Glu Thr Leu Ser Phe Pro His Ala Ala
            1925                1930                1935
Ser Ile Pro Leu Ala Phe Thr Thr Ala Tyr Ile Ser Leu Tyr Thr Val
            1940                1945                1950
Ala Arg Ile Leu Pro Gly Glu Thr Val Leu Ile His Ala Gly Ala Gly
            1955                1960                1965
Gly Val Gly Gln Ala Ala Ile Ile Leu Ala Gln Leu Thr Gly Ala Glu
            1970                1975                1980
Val Phe Thr Thr Ala Gly Ser Glu Thr Lys Arg Asn Leu Leu Ile Asp
1985                1990                1995                2000
Lys Phe His Leu Asp Pro Asp His Val Phe Ser Ser Arg Asp Ser Ser
            2005                2010                2015
Phe Val Asp Gly Ile Lys Thr Arg Thr Arg Gly Lys Gly Val Asp Val
            2020                2025                2030
Val Leu Asn Ser Leu Ala Gly Pro Leu Leu Gln Lys Ser Phe Asp Cys
            2035                2040                2045
Leu Ala Arg Phe Gly Arg Phe Val Glu Ile Gly Lys Lys Asp Leu Glu
            2050                2055                2060
Gln Asn Ser Arg Leu Asp Met Ser Thr Phe Val Arg Asn Val Ser Phe
2065                2070                2075                2080
```

-continued

Ser Ser Val Asp Ile Leu Tyr Trp Gln Gln Ala Lys Pro Ala Glu Ile
            2085                2090                2095

Phe Gln Ala Met Ser Glu Val Ile Leu Leu Trp Glu Arg Thr Ala Ile
            2100                2105                2110

Gly Leu Ile His Pro Ile Ser Glu Tyr Pro Met Ser Ala Leu Glu Lys
            2115                2120                2125

Ala Phe Arg Thr Met Gln Ser Gly Gln His Val Gly Lys Ile Val Val
            2130                2135                2140

Thr Val Ala Pro Asp Asp Ala Val Leu Val Arg Gln Glu Arg Met Pro
2145                2150                2155                2160

Leu Phe Leu Lys Pro Asn Val Ser Tyr Leu Val Ala Gly Gly Leu Gly
            2165                2170                2175

Gly Ile Gly Arg Arg Ile Cys Glu Trp Leu Val Asp Arg Gly Ala Arg
            2180                2185                2190

Tyr Leu Ile Ile Leu Ser Arg Thr Ala Arg Val Asp Pro Val Val Thr
            2195                2200                2205

Ser Leu Gln Glu Arg Gly Cys Thr Val Ser Val Gln Ala Cys Asp Val
            2210                2215                2220

Ala Asp Glu Ser Gln Leu Glu Ala Ala Leu Gln Gln Cys Arg Ala Glu
2225                2230                2235                2240

Glu Met Pro Pro Ile Arg Gly Val Ile Gln Gly Ala Met Val Leu Lys
            2245                2250                2255

Asp Ala Leu Val Ser Gln Met Thr Ala Asp Gly Phe His Ala Ala Leu
            2260                2265                2270

Arg Pro Lys Val Gln Gly Ser Trp Asn Leu His Arg Ile Ala Ser Asp
            2275                2280                2285

Val Asp Phe Phe Val Met Leu Ser Ser Leu Val Gly Val Met Gly Gly
            2290                2295                2300

Ala Gly Gln Ala Asn Tyr Ala Ala Ala Gly Ala Phe Gln Asp Ala Leu
2305                2310                2315                2320

Ala Glu His Arg Met Ala His Asn Gln Pro Ala Val Thr Ile Asp Leu
            2325                2330                2335

Gly Met Val Gln Ser Ile Gly Tyr Val Ala Glu Thr Asp Ser Ala Val
            2340                2345                2350

Ala Glu Arg Leu Gln Arg Ile Gly Tyr Gln Pro Leu His Glu Glu Glu
            2355                2360                2365

Val Leu Asp Val Leu Glu Gln Ala Ile Ser Pro Val Cys Ser Pro Ala
            2370                2375                2380

Ala Pro Thr Arg Pro Ala Val Ile Val Thr Gly Ile Asn Thr Arg Pro
2385                2390                2395                2400

Gly Pro His Trp Ala His Ala Asp Trp Met Gln Glu Ala Arg Phe Ala
            2405                2410                2415

Gly Ile Lys Tyr Arg Asp Pro Leu Arg Asp Asn His Gly Ala Leu Ser
            2420                2425                2430

Leu Thr Pro Ala Glu Asp Asp Asn Leu His Ala Arg Leu Asn Arg Ala
            2435                2440                2445

Ile Ser Gln Gln Glu Ser Ile Ala Val Ile Met Glu Ala Met Ser Cys
            2450                2455                2460

Lys Leu Ile Ser Met Phe Gly Leu Thr Asp Ser Glu Met Ser Ala Thr
2465                2470                2475                2480

Gln Thr Leu Ala Gly Ile Gly Val Asp Ser Leu Val Ala Ile Glu Leu
            2485                2490                2495

```
Arg Asn Trp Ile Thr Ala Lys Phe Asn Val Asp Ile Ser Val Phe Glu
            2500                2505                2510

Leu Met Glu Gly Arg Thr Ile Ala Lys Val Ala Glu Val Val Leu Gln
        2515                2520                2525

Arg Tyr Lys Ala
    2530

<210> SEQ ID NO 11
<211> LENGTH: 249
<212> TYPE: PRT
<213> ORGANISM: Aspergillus terreus

<400> SEQUENCE: 11

Met Ala Thr Gln Glu Phe Leu Ser Asp Val Ser Ser Gly Phe Leu Ser
  1               5                  10                  15

Ala Glu Ala Ile Arg Tyr Arg Val Lys Thr Gly Val Ser Met Asp Gly
             20                  25                  30

Trp Met Lys Arg Gly Tyr Ser Cys Asn Ser Val Arg Thr Asp Asp Lys
         35                  40                  45

His His Leu Arg His Leu Thr Asn Ile Gly Leu Asp Thr Pro Pro Cys
     50                  55                  60

Pro Lys Ser Leu Pro Ala Ala His Ser Ala Val Ala Ser Cys Leu Thr
 65                  70                  75                  80

Phe Val Pro Pro Asp Pro Cys Glu Asn Trp Glu Ala Leu Gln Val Ala
                 85                  90                  95

Trp Asp Lys Ala Cys Cys Arg Asn Pro Thr Pro Leu Phe Phe Ile Cys
            100                 105                 110

Val Ser Leu Leu Phe Ser Phe Tyr Ser Leu Trp Leu Gln Arg Gly Gly
        115                 120                 125

Cys Gly Arg Tyr Gly Gly Leu His Arg Val Ser Lys Val Phe Pro Lys
    130                 135                 140

Val Trp Pro Asp Asp Met Asp Ser Gln Leu Pro Ser Arg Leu Gln Thr
145                 150                 155                 160

Leu Val Ser Lys Arg Lys Pro Glu Pro Ala Pro Asn Asn Ser Thr Tyr
                165                 170                 175

Ile Ser Lys Gly Tyr Ala Thr Phe Phe Asn Gln Phe Ser Leu Pro Ser
            180                 185                 190

Val Asp Val Thr Gln Ile Leu Asn Gln Thr Leu Gln His His Asp Val
        195                 200                 205

Glu Thr Ile Asn Leu Asp Cys Gly Ser Gly Leu Leu Thr Leu Arg Thr
    210                 215                 220

Gln Leu Arg Ile Leu Leu Ile Gly Lys Pro Lys Ile Ile Lys Pro Phe
225                 230                 235                 240

Ser Gly Leu Arg Thr Ser Ile Asn Glu
                245

<210> SEQ ID NO 12
<211> LENGTH: 742
<212> TYPE: PRT
<213> ORGANISM: Aspergillus terreus

<400> SEQUENCE: 12

Met Glu Ser Ala Glu Leu Ser Ser Lys Arg Gln Ala Phe Pro Ala Cys
  1               5                  10                  15

Asp Glu Cys Arg Ile Arg Lys Val Arg Cys Ser Lys Glu Gly Pro Lys
             20                  25                  30
```

-continued

```
Cys Ser His Cys Leu Arg Tyr Asn Leu Pro Cys Glu Phe Ser Asn Lys
         35                  40                  45

Val Ala Arg Asp Val Glu Lys Leu Gly Ser Arg Val Gly Asp Ile Glu
 50                  55                  60

His Ala Leu Gln Arg Cys Leu Ser Phe Ile Asp Ala His Gln Gly Phe
 65                  70                  75                  80

Arg Asp Leu Ser Arg Pro Gln Ser Gln Glu Ser Gly Tyr Thr Ser Ser
             85                  90                  95

Thr Ser Ser Glu Glu Cys Glu Val Asn Leu Tyr Ser Gly Lys His Thr
            100                 105                 110

Ser Pro Thr Glu Glu Asp Gly Phe Trp Pro Leu His Gly Tyr Gly Ser
        115                 120                 125

Phe Val Ser Leu Val Met Glu Ala Gln Ala Ala Asn Ala Asn Leu Thr
130                 135                 140

Ser Trp Leu Pro Val Asp Met Thr Ser Gly Gln Val Ala Glu Met Val
145                 150                 155                 160

Ala Phe Asp Arg Gln Ala Val Ser Ala Val Arg Ser Lys Val Ala Glu
                165                 170                 175

Ala Asn Glu Thr Leu Gln Gln Ile Ile Glu Asp Ile Pro Thr Leu Ser
            180                 185                 190

Ala Ser Glu Asn Asp Thr Phe Leu Pro Ser Leu Pro Pro Arg Ala Leu
        195                 200                 205

Val Glu Pro Ser Ile Asn Glu Tyr Phe Lys Lys Leu His Pro Arg Leu
210                 215                 220

Pro Ile Phe Ser Arg Gln Thr Ile Met Asp Ala Val Glu Ser Gln Tyr
225                 230                 235                 240

Thr Ile Arg Thr Gly Pro Pro Asp Leu Val Trp Ile Thr Ser Phe Asn
                245                 250                 255

Cys Ile Val Leu Gln Ala Leu Thr Gln Thr Ser Ile Ala Asn Lys Val
            260                 265                 270

Val Gly Cys Thr Gly Gln Asp Ile Pro Ile Asp Tyr Met Ile Ile Ser
        275                 280                 285

Leu Leu Arg Asn Ile Arg Gln Cys Tyr Asn Arg Leu Glu Thr Leu Val
290                 295                 300

Lys Pro Arg Leu Ser Asn Ile Arg Ala Leu Phe Cys Leu Ala Leu Val
305                 310                 315                 320

Ala Met Glu Tyr Phe Asp Phe Ala Ile Phe Leu Thr Ile Phe Ala Gln
                325                 330                 335

Val Cys Glu Leu Ser Arg Leu Ile Gly Leu His Leu Thr Thr Thr Thr
            340                 345                 350

Pro Pro Thr Glu Asp Gly Ala Val Gly Asp Gln Pro Lys Asp Leu Phe
        355                 360                 365

Trp Ser Ile Phe Leu Val Asp Lys His Val Ser Ile Ile Gly Gly Lys
370                 375                 380

Ala Cys Leu Leu Pro Ser Tyr Asp Cys Ser Val Pro Leu Pro Pro Tyr
385                 390                 395                 400

Asp Ser Ala Ala Pro Leu Pro Asn Ala Phe Ala Ala Arg Ile Arg Leu
                405                 410                 415

Ala Phe Ile Leu Glu Glu Ile Tyr Leu Gly Leu Tyr Ser Ala Lys Ser
            420                 425                 430

Ser Lys Met Glu Gln Ser Arg Val Arg Arg Arg Ile Arg Arg Ile Ala
        435                 440                 445

Arg Lys Leu Ser Gln Trp His Val Gln His Glu His Val Leu Arg Thr
```

-continued

```
            450                 455                 460
Gly Asp Pro Asn Arg Pro Leu Glu Glu Tyr Ile Cys Ala Thr Gln Leu
465                 470                 475                 480

Arg Phe Ala Leu Ser Ser Cys Trp Val Leu Leu His Lys Arg Ile Trp
                485                 490                 495

Ser Gln Glu Arg Gly Ala Val Cys Leu Gln His Ala Arg Asp Cys Leu
            500                 505                 510

Met Leu Phe Lys Gln Leu Cys Asp Gly Cys Lys Ser Gly Phe Ser Asn
        515                 520                 525

Phe Asp Ser Ile Val Leu Asn Tyr Ser Leu Ile Ser Phe Met Gly Ile
    530                 535                 540

Tyr Val His Ile Val Glu Glu Asp Gln Pro Ile His Ser Gln Asp Met
545                 550                 555                 560

Glu Ile Leu Thr Phe Phe Ala Ile Tyr Thr Asn Arg Ser Ala Ser Asn
                565                 570                 575

Arg Ser Ser Ala Ser Ile Ser Tyr Lys Leu Ser Gln Val Ala Ser Arg
            580                 585                 590

Cys Ser Asp Ile Ala Leu Leu Leu Gln Asn Leu Arg Glu Arg Arg Phe
        595                 600                 605

Ile Pro Thr Thr Ile Ser Arg Ser Pro Thr Pro Ser Trp Asn Glu Pro
    610                 615                 620

Thr Tyr Met Asp Tyr Asp Val Ala Asn Ala Ser Thr Ser Thr Thr Ser
625                 630                 635                 640

Thr Gly Ser Ser Tyr Asn Leu Asn Ile Ser Pro Leu Gly Val Pro Gly
                645                 650                 655

Asp Gly Gln Val Trp Asp Ile Tyr Phe Asn Pro Arg Glu Ile Pro Met
            660                 665                 670

Asp Gly Thr Ile Ala Thr Pro Ser Glu Asp Ala Thr Gln Asp Leu Leu
        675                 680                 685

Ser Asn Asp Ala Gly Gln Cys Leu Gly Phe Pro Asp Phe Ser Leu Gly
    690                 695                 700

Ile Asp Asn Phe Ser Asp Phe Pro Leu Gly Ile Asp Met Thr Ser Gln
705                 710                 715                 720

Ser Glu Phe Gly Leu Ile Met Glu Glu Asp Ile Ile Arg Tyr Glu Arg
                725                 730                 735

Leu Leu Asp Arg Pro Val
            740

<210> SEQ ID NO 13
<211> LENGTH: 301
<212> TYPE: PRT
<213> ORGANISM: Aspergillus terreus

<400> SEQUENCE: 13

Met Glu Ser Lys Val Gln Thr Asn Val Pro Leu Pro Lys Ala Pro Leu
1               5                   10                  15

Thr Gln Lys Ala Arg Gly Lys Arg Thr Lys Gly Ile Pro Ala Leu Val
            20                  25                  30

Ala Gly Ala Cys Ala Gly Ala Val Glu Ile Ser Ile Thr Tyr Pro Phe
        35                  40                  45

Glu Ser Ala Lys Thr Arg Ala Gln Leu Lys Arg Arg Asn His Asp Val
    50                  55                  60

Ala Ala Ile Lys Pro Gly Ile Arg Gly Trp Tyr Ala Gly Tyr Gly Ala
65                  70                  75                  80
```

-continued

```
Thr Leu Val Gly Thr Thr Leu Lys Ala Ser Val Gln Phe Ala Ser Phe
                 85                  90                  95

Asn Ile Tyr Arg Ser Ala Leu Ser Gly Pro Asn Gly Glu Leu Ser Thr
            100                 105                 110

Gly Ala Ser Val Leu Ala Gly Phe Gly Ala Gly Val Thr Glu Ala Val
        115                 120                 125

Leu Ala Val Thr Pro Ala Glu Ala Ile Lys Thr Lys Ile Ile Asp Ala
    130                 135                 140

Arg Lys Val Gly Asn Ala Glu Leu Ser Thr Thr Phe Gly Ala Ile Ala
145                 150                 155                 160

Gly Ile Leu Arg Asp Arg Gly Pro Leu Gly Phe Phe Ser Ala Val Gly
                165                 170                 175

Pro Thr Ile Leu Arg Gln Ser Ser Asn Ala Ala Val Lys Phe Thr Val
            180                 185                 190

Tyr Asn Glu Leu Ile Gly Leu Ala Arg Lys Tyr Ser Lys Asn Gly Glu
        195                 200                 205

Asp Val His Pro Leu Ala Ser Thr Leu Val Gly Ser Val Thr Gly Val
    210                 215                 220

Cys Cys Ala Trp Ser Thr Gln Pro Leu Asp Val Ile Lys Thr Arg Met
225                 230                 235                 240

Gln Ser Leu Gln Ala Arg Gln Leu Tyr Gly Asn Thr Phe Asn Cys Val
                245                 250                 255

Lys Thr Leu Leu Arg Asn Glu Gly Ile Gly Val Phe Trp Ser Gly Val
            260                 265                 270

Trp Phe Arg Thr Gly Arg Leu Ser Leu Thr Ser Ala Ile Met Phe Pro
        275                 280                 285

Val Tyr Glu Lys Val Tyr Lys Phe Leu Thr Gln Pro Asn
    290                 295                 300

<210> SEQ ID NO 14
<211> LENGTH: 490
<212> TYPE: PRT
<213> ORGANISM: Aspergillus terreus

<400> SEQUENCE: 14

Met Thr Lys Gln Ser Ala Asp Ser Asn Ala Lys Ser Gly Val Thr Ala
  1               5                  10                  15

Glu Ile Cys His Trp Ala Ser Asn Leu Ala Thr Asp Asp Ile Pro Pro
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Ala Val Ile Leu Ala Ala Ile
    130                 135                 140

Val Gly Phe Glu Ser Gly Pro Arg Ile Gly Leu Lys Ala Ile Tyr Gly Ser
145                 150                 155                 160
```

-continued

```
Asp Leu Leu Asn Asn Gly Trp His Cys Gly Ala Val Tyr Gly Ala Pro
                165                 170                 175
Ala Gly Ala Leu Ala Thr Gly Lys Leu Leu Gly Leu Thr Pro Asp Ser
        180                 185                 190
Met Glu Asp Ala Leu Gly Ile Ala Cys Thr Gln Ala Cys Gly Leu Met
    195                 200                 205
Ser Ala Gln Tyr Gly Gly Met Val Lys Arg Val Gln His Gly Phe Ala
210                 215                 220
Ala Arg Asn Gly Leu Leu Gly Leu Ala His Gly Gly Tyr Glu
225                 230                 235                 240
Ala Met Lys Gly Val Leu Glu Arg Ser Tyr Gly Gly Phe Leu Lys Met
            245                 250                 255
Phe Thr Lys Gly Asn Gly Arg Glu Pro Pro Tyr Lys Glu Glu Val
        260                 265                 270
Val Ala Gly Leu Gly Ser Phe Trp His Thr Phe Thr Ile Arg Ile Lys
        275                 280                 285
Leu Tyr Ala Cys Cys Gly Leu Val His Gly Pro Val Glu Ala Ile Glu
    290                 295                 300
Asn Leu Gln Arg Arg Tyr Pro Glu Leu Leu Asn Arg Ala Asn Leu Ser
305                 310                 315                 320
Asn Ile Arg His Val His Val Gln Leu Ser Thr Ala Ser Asn Ser His
            325                 330                 335
Cys Gly Trp Ile Pro Glu Glu Arg Pro Ile Ser Ser Ile Ala Gly Gln
            340                 345                 350
Met Ser Val Ala Tyr Ile Leu Ala Val Gln Leu Val Asp Gln Gln Cys
    355                 360                 365
Leu Leu Ala Gln Phe Ser Glu Phe Asp Asp Asn Leu Glu Arg Pro Glu
    370                 375                 380
Val Trp Asp Leu Ala Arg Lys Val Thr Pro Ser His Ser Glu Glu Phe
385                 390                 395                 400
Asp Gln Asp Gly Asn Cys Leu Ser Ala Gly Arg Val Arg Ile Glu Phe
            405                 410                 415
Asn Asp Gly Ser Ser Val Thr Glu Thr Val Glu Lys Pro Leu Gly Val
        420                 425                 430
Lys Glu Pro Met Pro Asn Glu Arg Ile Leu His Lys Tyr Arg Thr Leu
    435                 440                 445
Ala Gly Ser Val Thr Asp Glu Thr Arg Val Lys Glu Ile Glu Asp Leu
    450                 455                 460
Val Leu Ser Leu Asp Arg Leu Thr Asp Ile Ser Pro Leu Leu Glu Leu
465                 470                 475                 480
Leu Asn Cys Pro Val Lys Ser Pro Leu Val
                485                 490

<210> SEQ ID NO 15
<211> LENGTH: 488
<212> TYPE: PRT
<213> ORGANISM: Aspergillus terreus

<400> SEQUENCE: 15

Met Gly Arg Gly Asp Thr Glu Ser Pro Asn Pro Ala Thr Thr Ser Glu
  1               5                  10                  15
Gly Ser Gly Gln Asn Glu Pro Glu Lys Lys Gly Arg Asp Ile Pro Leu
             20                  25                  30
Trp Arg Lys Cys Val Ile Thr Phe Val Val Ser Trp Met Thr Leu Val
```

-continued

```
                 35                  40                      45
Val Thr Phe Ser Ser Thr Cys Leu Leu Pro Ala Ala Pro Glu Ile Ala
             50                  55                  60
Asn Glu Phe Asp Met Thr Val Glu Thr Ile Asn Ile Ser Asn Ala Gly
 65                  70                  75                  80
Val Leu Val Ala Met Gly Tyr Ser Ser Leu Ile Trp Gly Pro Met Asn
                 85                  90                  95
Lys Leu Val Gly Arg Arg Thr Ser Tyr Asn Leu Ala Ile Ser Met Leu
                100                 105                 110
Cys Ala Cys Ser Ala Gly Thr Ala Ala Ile Asn Glu Lys Met Phe
             115                 120                 125
Ile Ala Phe Arg Val Leu Ser Gly Leu Thr Gly Thr Ser Phe Met Val
         130                 135                 140
Ser Gly Gln Thr Val Leu Ala Asp Ile Phe Glu Pro Val Tyr Arg Gly
145                 150                 155                 160
Thr Ala Val Gly Phe Phe Met Ala Gly Thr Leu Ser Gly Pro Ala Ile
                165                 170                 175
Gly Pro Cys Val Gly Gly Val Ile Val Thr Phe Thr Ser Trp Arg Val
             180                 185                 190
Ile Phe Trp Leu Gln Leu Gly Met Ser Gly Leu Gly Leu Val Leu Ser
         195                 200                 205
Leu Leu Phe Phe Pro Lys Ile Glu Gly Thr Ser Glu Lys Val Ser Thr
210                 215                 220
Ala Phe Lys Pro Thr Thr Leu Val Ser Ile Ile Ser Lys Phe Ser Pro
225                 230                 235                 240
Thr Asp Val Leu Lys Gln Trp Val Tyr Pro Asn Val Phe Leu Ala Val
                245                 250                 255
Ser Ala Trp Glu Ile Cys Pro Leu His Leu Leu Glu Thr Lys Cys Ser
             260                 265                 270
Cys Arg Lys Gln Lys Asp Leu Cys Cys Gly Leu Leu Ala Ile Thr Gln
         275                 280                 285
Tyr Ser Ile Leu Thr Ser Ala Arg Ala Ile Phe Asn Ser Arg Phe His
         290                 295                 300
Leu Thr Thr Ala Leu Val Ser Gly Leu Phe Tyr Leu Ala Pro Gly Ala
305                 310                 315                 320
Gly Phe Leu Ile Gly Ser Leu Val Gly Leu Lys Leu Ser Asp Arg Thr
                325                 330                 335
Val Arg Arg Tyr Ile Val Lys Arg Gly Phe Arg Leu Pro Gln Asp Arg
             340                 345                 350
Leu His Ser Gly Leu Ile Thr Leu Phe Ala Val Leu Pro Ala Gly Thr
         355                 360                 365
Leu Ile Tyr Gly Trp Thr Leu Gln Glu Asp Lys Gly Gly Met Val Val
370                 375                 380
Pro Ile Ile Ala Ala Phe Phe Ala Gly Trp Gly Leu Met Gly Ser Phe
385                 390                 395                 400
Asn Cys Leu Asn Thr Tyr Val Ala Val Glu Ala Leu Pro Arg Asn Arg
                405                 410                 415
Ser Ala Val Ile Ala Gly Lys Tyr Met Ile Gln Tyr Ser Phe Ser Ala
             420                 425                 430
Gly Ser Ser Ala Leu Val Val Pro Val Ile Asp Ala Leu Gly Val Gly
         435                 440                 445
Trp Thr Phe Thr Leu Cys Val Val Ala Ser Thr Ile Ala Gly Leu Ile
         450                 455                 460
```

```
Thr Ala Ala Ile Ala Arg Trp Gly Ile Asn Met Gln Arg Trp Ala Glu
465                 470                 475                 480

Arg Ala Phe Asn Leu Pro Thr Gln
                485

<210> SEQ ID NO 16
<211> LENGTH: 516
<212> TYPE: PRT
<213> ORGANISM: Aspergillus terreus

<400> SEQUENCE: 16

Met Thr Leu Gln Ile Ile Val Ile Ala Ala Thr Ala Val Ile Tyr Phe
  1               5                  10                  15

Leu Thr Arg Tyr Phe Asn Arg Thr Asp Ile Pro Lys Ile Lys Gly Ile
                 20                  25                  30

Pro Glu Ile Pro Gly Val Pro Ile Phe Gly Asn Leu Ile Gln Leu Gly
             35                  40                  45

Val Lys His Ala Thr Val Ala Arg Lys Trp Ser Lys Glu Phe Gly Pro
 50                  55                  60

Val Phe Gln Ala Arg Leu Gly Asn Arg Arg Val Ile Phe Ala Asn Thr
 65                  70                  75                  80

Phe Glu Ser Thr Arg Gln Leu Trp Ile Lys Glu Gln Ser Ser Met Ile
                 85                  90                  95

Ser Arg Pro Thr Phe His Thr Phe His Gly Val Val Ser Ser Ser Gln
            100                 105                 110

Gly Phe Thr Ile Gly Thr Ser Pro Trp Asp Glu Ser Cys Lys Arg Arg
        115                 120                 125

Arg Lys Ala Ala Thr Ala Leu Asn Arg Val Ala Val Gln Ser Tyr
130                 135                 140

Met Pro Ile Ile Asp Leu Glu Ser Met Ala Ser Ile Lys Glu Leu Leu
145                 150                 155                 160

Lys Asp Ser Gln Gly Gly Lys Ile Asp Ile Asn Pro Thr Pro Tyr Phe
                165                 170                 175

Gln Arg Phe Ala Leu Asn Thr Ser Leu Thr Leu Asn Tyr Gly Tyr Arg
            180                 185                 190

Ile Glu Gly Asn Val Asn Asp Gln Leu Leu Arg Glu Ile Cys Glu Val
        195                 200                 205

Gln Arg Gly Val Ala Asn Leu Arg Ser Thr Ser Asn Asn Trp Gln Asp
210                 215                 220

Tyr Val Pro Leu Leu Arg Leu Phe Ser Asn Arg Ser Asn Gln Ala Lys
225                 230                 235                 240

His Leu Arg Ala Arg Arg Asp Lys Tyr Met Ala Phe Leu Phe Asp Ile
                245                 250                 255

Leu Lys Asp Arg Met Ala Lys Gly Thr Asp Lys Pro Cys Ile Thr Gly
            260                 265                 270

Asn Ile Leu Lys Asn Pro Glu Thr Lys Leu Thr Asp Ala Glu Ile Lys
        275                 280                 285

Ser Ile Cys Leu Thr Met Val Ser Ala Gly Leu Asp Thr Val Pro Gly
290                 295                 300

Asn Leu Ile Met Gly Ile Ala Tyr Leu Ser Ser Glu Asp Gly Gln Arg
305                 310                 315                 320

Ile Gln Gln Lys Ala Tyr Glu Glu Ile Met Ser Val Tyr Pro Asn Gly
                325                 330                 335

Asp Ala Trp Glu Arg Cys Leu Val Glu Glu Lys Val Pro Tyr Ile Thr
```

```
                340              345              350
Ala Leu Val Lys Glu Thr Leu Arg Phe Trp Thr Val Met Pro Ile Cys
            355              360              365

Ile Pro Arg Val Asn Ile Lys Glu Val Ile Tyr Asn Gly Ala Arg Ile
370              375              380

Pro Ala Gly Thr Thr Phe Phe Met Asn Ala Trp Ala Ala Asn Tyr Asp
385              390              395              400

Glu Asp His Phe Asp Met Pro Asn Arg Phe Leu Pro Glu Arg Tyr Leu
            405              410              415

Glu Pro Ser Glu Gly Phe Gly Thr Pro His Tyr Ser Phe Gly Ala Gly
            420              425              430

Thr Arg Met Cys Ala Ala Ser His Leu Ala Ser Arg Glu Leu Tyr Thr
            435              440              445

Val Phe Leu Arg Phe Ile Val Ala Phe Thr Ile Glu Pro Ala Gln Asn
450              455              460

Pro Ala Asp Met Pro Val Leu Asp Ala Ile Glu Cys Asn Ala Thr Pro
465              470              475              480

Thr Ser Met Thr Thr Glu Pro Lys Pro Phe Lys Val Gly Phe Lys Pro
            485              490              495

Arg Asp Glu Thr Ser Leu Arg Arg Trp Ile Ala Glu Ser Glu Arg
            500              505              510

Thr Lys Glu Leu
        515

<210> SEQ ID NO 17
<211> LENGTH: 481
<212> TYPE: PRT
<213> ORGANISM: Aspergillus terreus

<400> SEQUENCE: 17

Met Lys Pro Ala Ile Leu Met Lys Tyr Trp Leu Phe Val Ser Ala Val
1               5               10              15

Ser Ala Ser Thr Leu Asn Gly Lys Leu Thr Leu Ser Glu Thr Lys Val
            20              25              30

Thr Gly Ala Val Gln Leu Ala Cys Thr Asn Ser Pro Pro Asp Ile Tyr
        35              40              45

Ile Asp Pro Asp Asp Ser Val Ser Val Val Arg Ala Ala His Asp Leu
    50              55              60

Ala Leu Asp Phe Gly Arg Val Phe Gly Lys Asn Ala Thr Val Arg Phe
65              70              75              80

Thr Asn Glu Thr His Pro Thr Ser Met Ala Ile Ile Ala Gly Thr Ile
            85              90              95

Asp Lys Ser Thr Phe Leu Gln Arg Leu Ile Ala Asp His Lys Leu Asp
        100             105             110

Val Thr Ser Ile Arg Gly Gln Trp Glu Ser Tyr Ser Ser Ala Leu Val
    115             120             125

Leu Gly Pro Ala Lys Gly Ile Gln Asn Ala Leu Val Ile Ala Gly Ser
130             135             140

Asp Arg Arg Gly Ala Ile Tyr Gly Leu Tyr Asp Ile Ser Glu Gln Ile
145             150             155             160

Gly Val Ser Pro Leu Phe Trp Trp Thr Asp Val Thr Pro Thr Lys Leu
            165             170             175

Asp Ala Ile Tyr Ala Leu Asp Val Gln Lys Val Gln Gly Pro Pro Ser
        180             185             190
```

Val Lys Tyr Arg Gly Ile Phe Ile Asn Asp Glu Ala Pro Ala Leu His
           195                 200                 205

Asn Trp Ile Leu Ala Asn Tyr Gly Glu Val Glu Asn Gly Asp Pro Ala
           210                 215                 220

Phe Ile Ser Arg Phe Tyr Ala His Val Phe Glu Leu Ile Leu Arg Leu
225                 230                 235                 240

Lys Gly Asn Tyr Leu Trp Pro Ala Met Trp Ser Asn Met Phe Tyr Val
           245                 250                 255

Asp Asp Thr Asn Asn Gly Pro Leu Ala Asp Tyr Tyr Gly Val Val Met
           260                 265                 270

Gly Thr Ser His Thr Gly Met Thr Val Gly Thr Pro Cys Leu Lys Ala
           275                 280                 285

His Ala Asp Tyr Glu Lys Glu Pro Met Ala Arg Ala Thr Asn Glu Gln
           290                 295                 300

Ser Gln Phe Leu Asn Gly Thr Trp Asp Trp Ile Ser Asn Glu Val Asn
305                 310                 315                 320

Val Lys Ala Phe Met Arg Glu Gly Val Ile Arg Ser Gln His Trp Glu
           325                 330                 335

Thr Ala Tyr Thr Met Gly Met Arg Gly Leu Gly Asp Ala Ala Ser Pro
           340                 345                 350

Thr Leu Asn Ala Thr Val Glu Glu Ser Ile Val Ser Trp Gln Glu Ser
           355                 360                 365

Val Leu Ser Asp Ile Leu Asn Lys Thr Asn Leu Ser Asn Val Val Gln
           370                 375                 380

Pro Phe Val Leu Phe Asp Glu Leu Gly Thr Tyr Tyr Glu Ser Gly Met
385                 390                 395                 400

Thr Val Pro Asp Gln Val Thr Leu Ile Tyr Pro Asp Asp Asn Ala Gly
           405                 410                 415

Asn Met Leu Arg Leu Pro Leu Gln Asn Glu Thr Gly Arg Ser Gly Gly
           420                 425                 430

Ala Gly Ile Tyr Tyr His Phe Asp Met Asn Ala Pro Pro Arg Cys Tyr
           435                 440                 445

Lys Trp Ile Asn Thr Ala Gln Leu Ile Arg Thr Trp Asp Gln Leu Arg
           450                 455                 460

Ala Ala Tyr Ser His Gly Ala Gln Thr Val Trp Val Ala Asn Ile Gly
465                 470                 475                 480

Asp

<210> SEQ ID NO 18
<211> LENGTH: 33000
<212> TYPE: DNA
<213> ORGANISM: Aspergillus terreus

<400> SEQUENCE: 18
tggattttct tcctgtaggc ccgtagctat gtaatctagc taaacagagc g cgtatttta      60 aatattagaa actgctcgcg tatcttatcc agagcgttag ctaggtaggt t acctggtct     120 gttttagcaa gctggacggc ctgcagggcg actaatattt aggctatttt t ataagcccg    180 gaaagatagc ttatatagct ataaggcttt agaaagatct actgcttaat a tctatttct    240 aaaataataa gaaatctaat aagagtactt ttaaagagat ctttcttaag a gtatggtcg    300 agtaagataa ttaaaaatat taaacaggcc taattaagca gttctttagt t tgctgctgc    360 tgattaacgc gctacaatag tttaagatct tagctttaga ttaggagatt a actagctgc    420 cggctataaa ttttatcta attaagcgcg gtaaactagg cagtatttag c tagtggcgg    480

-continued

```
agtaaaatta gctggttagt ccggctacta tggtaggcga agtaaataag a cactgctag        540 atctagtagt actaacagta cgtcgctagc cgtagataga tctagattag c tggttttag        600 atccccggcc ggcggaagaa gatattaatc taaatttagt tgaatttatt a atccggccc        660 ttcttaatcg cgtaataggt ctaattaatt agttgctgga cgctagcagt a aattacttt        720 agtaaagatt tagctatagg attagaaaag ctgccgagta gggcgactgc g gtttaatct        780 taattataaa ggtattccgg ctattaaata agctctagct ataaggaaat t gtagttaga        840 tgtagattaa taatagagat ctagtcgtta gtcctatccg cggtagccta a ttttttat        900 aaagcctgct cgacccgagc ctgaataatt atagctaagg tctttagaga g acggctttc        960 tctagtcttt aattagaaga ggcctcggta tatattactt taaagaatta a ctagtagat       1020 tagctgataa agaagcgctg atagctaata atatactctg ttagtcgggc g cgaagccta       1080 gcttatattt aagtaatagt cttctaactc tattttcttc gtgccctatt a taattagta       1140 tagttttaat tttaatattt atttattgtc tgtcggcact aatagatata t ttataatat       1200 aggcagctat aactacggta gactggaaga cctaaaatca gagagctact t agaggggg        1260 aaataaataa tctcctactt tagattaatt tagagctgct gaagtattac a gttaaagca       1320 gcttgttaga gggccggaat agtggtatta gaataaaagc tataacgcgt t tggaggtag       1380 ataataaaag tagtagaaga aactatatac tagtaggaag gtgtagtata g atctagatc       1440 ttataggtta agttatagag aaagagctct attgttaatt ctaggctcta a gagaaaagt       1500 acctagagag ttaagaataa aggaaaatag gtttctataa ggagctattt t cttttaat       1560 atttattata ttttttaaag atatattaat ggcgcgtcgg atacacgtag t aaaaagtaa       1620 attcgtgtct gctattgctt attcctgaag ataaaatata gatataatct c gctaggtcc       1680 tctttaaata agatagaacg gcggagctgt ctgttcgggg cacgcatgta a ggcgacggg       1740 agcacggcga aatattaaat cttgaccaat tagcaggcga gaaaatggat c gaaggttgg       1800 gtgaacttgg gcctagggac taggcaacca ccaagagaca tcctggctac t atagtccct       1860 attggcaatg gcctgattcg ctcggtccaa gctctgcgcg atcaaactcg a cgagttcgc       1920 cttgacgtgg accgcaacgt cacacatgaa aaccgcatag ggatccgggt c agatcccag       1980 cgcatcctgg cacgtatccg catcgggcag ctggatcgat ccggagttca t aagcgcggt       2040 aatttcgtct gtctcggtcg cgttcgtgct ctcggctgtc gtgtctccaa c aatcgcgat       2100 atcgggccat gcggatagga agaagtaagt gtttgggttg tcgggtctg g ttcttgggt        2160 tccgggctcg caccagcggt ggccgtcaaa tcgcgcgtcc atatcgatgt a atggatctg       2220 ctccgtattc cggcggtgt tgatgtcgga aatggtggat tggattaacg a gttgagcat        2280 gcggacgagg tcgttgagtt ccttgcgtag gtcggtcgtg agccacacat a gttgccgga       2340 ttgctgcggg tcgtagtgtg ggctttcgta ccagaaggtg gttgagtcgc a gtcggtggt       2400 gtcttcgttg aagaaggtga catagccagg gacgtagagg ttgaacgact a aagtaaagt       2460 cagcgcgacg aaggacagca cgacaggaat aaataaggat aacagggaga t atacgctag       2520 agccagatct atccaggatc ttttcatacg cagccctaag tttcgagccg a gtccgtcag       2580 accctgtatc ctgcatcagg ttgcgggctt tctcttcagt ctccagacac c actggcggt       2640 attgctcaag cgagtaccac cacattgtta gcacgcagtt ggaaaccaga t cgctgaaga       2700 acacatcgtt ccctccaatt gtcagggttg ccatggtagt ccccgtgggg t cctgtccta       2760 gccactggtc gatctttta ttcagcccaa ccgttgtatc tccagagcac g catagttgg       2820
```

-continued

| | | | | |
|---|---|---|---|---|
| tataagtgaa | atcctcagta | tcaaaccact | cctggacgag | ctttccgtag c tgttacttc | 2880 |
| ccacgcggca | actgtcaccg | gttgtggttc | ctgtacccat | cccagcggcg t aggagtcac | 2940 |
| cgaagtgaac | ataatcgttg | acgccgtaca | cagtgtcagc | atcataagac g aatcatcgt | 3000 |
| aggccggaca | gctggagtca | tccgccgaag | aagcagactc | ctcaggaagg g gaatctgtc | 3060 |
| gaccacatat | cttggtatag | tacccgccaa | gtacgacaag | agcccatgaa t ccgcattgt | 3120 |
| aggcggacaa | cttgctgtca | cagatgcctt | cttgcccgag | gttatttggg t ctgggcaaa | 3180 |
| gcaatctgcg | ttgccagtta | gcatcgccgg | ctatacggag | ctcattagcg g ctctttcag | 3240 |
| cctttctgcc | tctttcgata | cagtgtcgat | tgaaggtccc | tgcggcaaga t ctcgagctc | 3300 |
| ctttccatcc | atagacataa | tcgcgggtcc | tcctaaggtg | aaagaatcag t atcggcctg | 3360 |
| ggaatgagaa | aaaatatgtg | ataccaccca | ttctctccat | tgacaatctc c ataacatag | 3420 |
| tccgtatgcg | ttacttcgtg | caaaatcgcc | ccggctcgag | tgagatgggc a tcatgaaga | 3480 |
| ttaattgagt | cgcacctcgc | gagcactgac | ctggaactct | tcaactcatc t gtgaagaac | 3540 |
| tttgggcaga | aattaagccg | attcctattg | ttcatcatgg | ccaaccagcc g ttctcgtca | 3600 |
| cagccccgaa | ggttttttgca | agtgatcgtg | aacttttcgt | cgtcgaattg c gaagaccca | 3660 |
| gaaatcatgg | tgaccatccg | gtcgaacgta | taccttacat | ttatagtgaa g gtcaagctg | 3720 |
| tcggtgagtg | attcggcaaa | gaagatgtcc | ctatatgggc | gtatgcgcc g ccgctaaag | 3780 |
| tacgcaactt | ccgaggcagc | atcaagcgca | tattgcattt | cttcaaagag c gtctgcacc | 3840 |
| tgggccctag | tgcactcgct | gttgtcctga | taatgagggg | tgagctcgat g ggggctttt | 3900 |
| acaggagata | caggtagatt | ggggttagtt | atcgggccgt | catcgcctgt g tggtctttg | 3960 |
| gtggcacatt | cgttgtacca | cgtctgcgct | gtgttgttta | tggagttcca g atgctgtgc | 4020 |
| atgtctgcac | gaccgtcgcc | gttcagatca | gggaaataag | tgcatgagcc t tcaaccgcc | 4080 |
| cctcggtact | tgggaccctg | cggtccccat | tcgtatcgcg | atcccttgat a tcacgttgg | 4140 |
| ccaaggttgt | accacaccga | cccatctccc | gagaacttgt | ctgtccagat c atatcggcc | 4200 |
| tttccgtcgc | cgttgacgtc | ggcccagtgt | agattcgccc | tgtccttctc c tcggagtac | 4260 |
| ttgaattgat | caatgtagtc | ccatccatcg | tccccattga | cccagcccca g gtgcggccg | 4320 |
| tccttctcaa | cgcacagata | atcggccttg | ccgttgccag | aaacatcagc a aaatggacc | 4380 |
| ggccggtcaa | agaaaccaag | gcctcggtgc | tcggggcagt | aaagctcatc t gcagcattg | 4440 |
| atattgtagt | cccagtcaaa | actccccgtg | tctttgatct | tgttccgcca a acttgggcc | 4500 |
| ctgttcagat | tgtcgggatc | cgtccagatt | atatcgcagg | ctccgtcgcc g tcccagtct | 4560 |
| gcgagatgca | gatcgcgccg | gtcaagcttc | atgccaatct | gctcttgggg g tcgaagata | 4620 |
| atctcattcg | cccccccagaa | gctcgacccg | tcggcgggga | cttcaaccag g ccctattc | 4680 |
| ggataaagac | gcatatggcc | ggttgaatgg | atccaaatgt | agtccatcat a ccattgtcg | 4740 |
| tgcccatca | tattgcaata | cctgtctccg | tcggctataa | caattagcaa t caacctctc | 4800 |
| tatgagaact | tccttccata | cctttgatct | tagcccctcc | tgcgcccttg c tcttccaca | 4860 |
| catgaacgta | atacagcggc | ccaaaatact | tgtcagaggt | atccttcttg a tgaacacat | 4920 |
| agtcctgtct | cccgagctct | ccaaaatccg | ccacctcgcc | atagagtcgc g caaagtaga | 4980 |
| cctgatcccg | taatccggat | gtcccgaata | ttactcccat | tccgggatgc g acgggccag | 5040 |
| agttagcatc | ttggtagaac | ccctggcgcc | acacgacgtt | caacccgtca c cagactctc | 5100 |
| cttttgatgca | gctccgggag | ttggtgtatg | ttgtcgtagc | gccatcgtca t caacccaca | 5160 |
| tccagtcgtc | gcgcccgtcg | ccgttgatat | cctcgaatcg | cacgccgcgc a ggtctccca | 5220 |

-continued

```
tgactttccc cgtgaagcgc ttgcccagcg gctgccagta tgcggggata t cttcgatcc    5280 atccatttcg ccagcatgtg acgtcgccgt tgtcagccaa accgcagtag t cggcgcggc    5340 cgtcgccgtc gatatcagca aggcgtacat gtgcctgatc gtatccttcg g gactcttcc    5400 atagtccgat atcggtgaag gatggaggct tgttgctctt ggcgtcgccg t ctccattgt    5460 tgatgcttgc gtaggtggtc ccgtccaagg cgatgcagat gtagtcatca a gtccgtcgc    5520 ctatcattta tcacacataa atcagtccca gatggttcct cggcagacag a cacagtgct    5580 taccgttgat gtcgataaaa tgcacacccc ccgggttaca attattatga g tcgagaacg    5640 tccccccctt cgtaaactcc tgctcctcag tgtggacatt attcgtgtaa g aaacaaacg    5700 tcaccgcgcc ggagtcctta tctttgtgga agatcatcat gtcatcatac g ccctagtat    5760 aaagcctccc gaagaaaaag tgcagctcgt cgtcatcctt gtatggatcg g ctgcaccct    5820 tcccggcgcg gacagtaaac aacgccccgc tatactcgct gtcgtgtcga t agattccgt    5880 catcctcacc actcccttgc tgcgtgaacc cgccagcgta gactccgctc c cgtactctt    5940 tgtcacaggt ccccgtggat gagatgtcaa ggtccgccgg cttgacaatg a gctccgcca    6000 ccgcagcgtt gtagatcgcg ttataccaga tgtctgccat ctgggagtac c cgtagtcgt    6060 tggggtgctt gttatcggcg aagttatcgg ggtacgtgat ccagttgttt c cggggctgg    6120 gagccggcgg atccatatcg gccaggacga tggagacatt ctgcgcctcg c gcatgtcaa    6180 ggaccagctc gcggaactgc gcgttgacgg agggcctgtt agcttcgagg g ttgtggaac    6240 ccgaggggat cagggtcgac aggacgatga gcgtgttggc catgtccggg g cgccgatta    6300 gggtttcgat cagggagcgc atgcgctcgc cggcgttcgc agggtcgacg t tgtagtcgc    6360 agtcgttggt gccggcgttg atcagcacga cgttcggctt gtaggcgagc g agtttgcgg    6420 ccgcggtttg cacttgcgtt atcacgtcgc cgctgtgggc ttctacatcc t tttcccgcg    6480 tttatatgtc aattggtctg tctatctgtc ggagggtgg gggaagagag a tgcatacat    6540 tgtctaccat gtcaccgttg gacttactgc ccaccatgtc cacctcccag c cttcaaagc    6600 gaagtttgtc acggagaggt ttgcgatatc catttccggt tgaggatagg t atccccagg    6660 tgatggatgc gccaagaggg aggatccgta gagggacttt cagggcatca t ctcgttttg    6720 ctcttggacg ccattcagca gcgtcaaagt ctatatatct cgaatcgtct g tgggtcgcg    6780 agacagggac ggctgctcct gtggcagtag atgatagaag agccagtgtt a gattgaaca    6840 ccgtaaagaa aagtagagac gccattatcg atgctgactc tctgcaccct t cactcctct    6900 tccatactgc gagtcgcttt tatactttca cagccctcca gtcatttcat g tgtaagatg    6960 cctcggcgta tgtgccgttc tgaaacaagt gtacttccaa gaatcgcgag c tcgagtatg    7020 gtaccaggat aaacctggat acttaggtat caaagcatga gaccctggca t ttttcatgg    7080 caagtttggg ggccataatc ctgtggcaga ggttcatatg cggcggtcga g tcatgcaat    7140 gggtttattt ggcgtagttt acggagcaac caatcactgg cctgaatatg g taccaggat    7200 gaaccagaat agtaccaaag gatgagactg gcatccttca tagccataac t gttggggt    7260 catcatctgt gacagggaga tatgcagtga ttgagtggtg caacgggctt a aatgtaatc    7320 ggtgtttgca actacgcgga gtgctaggga ggcggctgat tggcatgata a gcaaaggct    7380 tagctgagac atggcactag gtagaggcta ggacctgcgt aagcattcat t ccgatgctc    7440 tattggataa gttatttaca atctccgcat taggcggcaa tccttaatat a gaatactag    7500 tatagagcac tatggacact ccgacgttca tttaatatct ccaccgtgt t accctctt    7560
```

-continued

```
tctgcctttg atctctatca agctggccct tctggcattt atccttgcat t aaacatgac    7620
tctaccaaca cttcctaact ggataaggat gtgcgtgcat ttgtcccttta c acatctcca   7680
tcagcaccgt tccccgaaat acgagtctat acctattaaa agtatccagg c taattcaca    7740
cagaatcctc atcatcctaa ccacagcctc cttctacccg cagatccggt g catccaact   7800
tcgaaactcc acgcacggca tctccactgc ctacatcctc ttcaacctaa t cagcgcaac   7860
agaacacttc accatcctat tcgcattgct ggtaaacagc ggcggagatg t cctcatcca   7920
tgagcccccc acgaccggcg acgggttgaa cctgtaccag cttttcgcag t gtggatggg   7980
atgcttagtc ctcttctgcc aagcaatcca tagcctccac gccaatccac g ccgcaaact   8040
catcctacta accatataca ttcaatacct atgcatttct atcttaccag a ggtcatcga   8100
cgcaatcacc actcccgagg aaacgagaaa acaaaggccg ccaacgggcg a gaggaactg   8160
gctgatcgga ctctttcttt ccgcgcacgc gatgaccgtc ctgccactat c ggccgtgct   8220
ccgcatcgcg ggattcatag atcagtcgcg actgatctcg cggcgcagac g ggagcagcc   8280
atcggtctta agcctgacag gcctggcgtg tcaggccgtg gtctttgctc t agtttctgg   8340
actctgggta ctcagggttc agcagcctgt tcctcgaatg ccgatgagaa g acctgtgga   8400
ttggatgtat tggtaccatg taattgggtg gccggttgtc gacgatgcgg t ttatgcgct   8460
gggacaatgg gttttgtttt ggtatgcggt ttgttggcgt tctcggggcg a tgctaggga   8520
tgaagcagtc catgctgggg agactgatga cctgttagga gaggatgaag g gcatgggta   8580
cggcggaacc gggacttctt agattgtctg tatatcattg tgccacgata t cgcgtgtaa   8640
caccatggtg tggaaggtat actcatcgcc atggattttt tgacaagctt g ctataatag   8700
ctcttggtta actctttttgc cttttttat tctgccatac ggtctcattc a gagcacgat   8760
ctgcagggga aagagaacag ctataccgtc gcatgatttc aaccttccaa a ctcttatta   8820
tcaaactggt aatagcaccg tgaatgggat ggcttaggct ttagatgaag g agttagagc   8880
ctggctgcaa gccctaaaca cctgtctagt ccacgttata atttagcaag t ctcccgagc   8940
tctcgcaagc ctaccactag cttatagtca atagattgtg gtatatccag g ggcctttta   9000
agtatttacg gctcatacaa aaagtaatat gagacagctc tactcttttt a catcatcta   9060
catctatcgc ctagattggt agctcgcagt gggtcatccc tatctgttac c ataagactt   9120
cccgtggtcg caattcaacc taatgcagga cttctctcgtg ggccgattta t tactagacc   9180
tattgatctt tgattgtggc ttcatccggt cgctattact tacagccaca g tgatcatag   9240
tattcgaatt acaatgttga acctctgcca cgattactat caggtccttc t agttggacc   9300
tctctccacc agcgttgaag tataatcccg tagactcaaa aaccaacccg a cctgatcca   9360
ataccaagtc taattataat cagaaaaaaa tattttaaaa attaaaatttt a tatagatat   9420
ctgctaatcc tcgcagacta tatataagaa acccgtaatc tgcgcggact a tagtagtat   9480
agatttagg acccgctccg cgcggagcgg agcggactgt ggatctgcgg a gagttagta   9540
tacaaaatac tagaggcggc gaggtcgagt tagcgcagtc tagtactaaa t aggaaagcg   9600
gttattttag cgcgaaaaca gggtactaat attttttggac ccccactgta c cttcacgga   9660
tagtaccaca caactacatt acgattatat atcatctttc cccctcccat g ttttcccca   9720
agcaccttac acgtggccgc cctcaactac ctagtttgtt gacagaagtg c agtaacagt   9780
gacctaactg agtgtagttt agagatatat attctactat aggggctaaa c cgtggtgg    9840
attacgcaga cttttttgcta aaagcataat agctacgata ggtagaatat a actatagat   9900
aaggtagatt agggtaggta cgactgcggc ggcttgatta ttccttgaaa a tgacgggct   9960
```

-continued

```
cttctggggt agactactgc tatagtgaac caggaaggcg gatatcctcg t cgcgccggc    10020 gcatcatgag cttcgtggtg ggatgaatgc gcacgctgaa agaatggcgg t agtactgca    10080 acggttcgtc ggggaccacc ttccagtcgt atcgtatgag caagtaggct a acatcatct    10140 tgatctcctt agaggcaaag aaccggccgg ggcaagcccg tggatgccaa c cgaagccga    10200 tgtggtcccc gttggtgttc tccagttggg cactgaacgc tttagccggg t cctctcgca    10260 ggcgcatata ccgtaagga tcgtattttg ccggctctgg ccagacctcg g ggttgctca    10320 tgcggtcggc agctaccgcc accagctctc cttttgggat aaaggttcca t tggagaaag    10380 tcacatcctg caatgcatag ctgcgcatgg tggcacattc gacgggcttg a cgcgctgtg    10440 actccttgag acaactatcc agcagtttga gcttgtacag cgaggcaggt g tccaacccc    10500 cttggccgat gaccgtccgg atctcatcac ggaggggctc aaggagatgg g gatgtcgga    10560 cgatgtccac caacccaccg atcagcaggt cggaggttcc gtagatacca g caaagtcca    10620 tggccagttg cgccccggct gcatcgtacc atttcccctt ggcagtatcc t cgaaccact    10680 ggatcgagtc tacgtagcga ggcggctcaa tgcccttt gc ccggcaggca t ctctttccg    10740 cacgtcgctc ctggataatg ggatcgagaa gttgccgggc tcgtcgaacc t gcgccgga    10800 gtttggctcc ctggggctcg agccaatgta caaggggcg cagaatgacg g gccagaggc    10860 gcagctggcg cgcttgaatt gccatcgtca ccgcgtggtg cttggcgatg t caagccact    10920 cctcattatg ggctaacttg ctcccgacca taataaagt cactgttcgg g tcactaagt    10980 ccagacactg gttatagaca ggcactgtgt gccattctga aagcaaaagc a catccctct    11040 tcatcagcta atggcctaaa aacaaaaata ctcatcatga tcacttacca t tgctgtcgc    11100 caaaaatatc cgtgataatc ccgctggctt cattggcaag aggcttgacg t acttgggag    11160 cttgggtctg gaactggttc ataaccacct tggtgatgag atgtgcatcc c tcgtgactt    11220 ccttgaatcc atcgaatccg ggaagatgag agtgaaagtc ctgatgagag c acgaagatc    11280 agtaagtcag gtcctcacag cggaagcagt tgcaaagaac ggtggactcc t taccgtgcc    11340 caagaacttg tacatacaga gctctttcat cttgcgaaac tcatcggcca t agaggaggg    11400 aagaatggtg cagtacccag agtcgactat gaaccgaatg ggcttatcat t ttgcgagaa    11460 ccagctctca atccatgacg gtgcattcgc atcaaaatcc cgtttggccc t catggtcgt    11520 cagttcccac catgttttcg gattgaacac cggcagatca gatctccggc c actcgagca    11580 caggtaaaga agaaggcata gtagccccgc actggtagtg accaagggcg c aaaccacga    11640 gccatgttgc tgcgtgtcat tccaagccag cgacagaagg tggtgcggct g tgtgagcgc    11700 gtcgacagtc atggctagga gaccaggtgt ggttgaggga taagatatcg a gagtgatgt    11760 gagcaaaaga tccgggaaag gtcgcgaagg aaagggcgtc tctcttacca a gaaagtctg    11820 ttccctatca tgcaatcacc gcttgctgta cggtggtgat gatgctggga t ggtggtggg    11880 tccccaccga ataacgccgg acagctgttg aagccgaatg acgccggcag g ccaaaagaa    11940 ccctaccttc acttactcaa tcggcgcttc ccctcctatc accaaatcgg a tgtaaatgg    12000 acgggcctta atagcgaccg gccgggccgg gaatccccaa acgtagatag a taggcatag    12060 acccgaaatc tttggcccgg catacatgag cacaggaagt ttcacgcgac g gcgcctttc    12120 ctgcctcagc ttcaatccaa gctcacgagt tctgtcgcct ctatcagtcg t gcaattgtc    12180 ctactgcaaa cagcatggct caatctatgt atcctaatga gcctattgtc g tggtcggca    12240 gtggttgtcg cttccctggt gacgccaaca caccctccaa gctctgggag c tactccagc    12300
```

```
atcctcgcga tgtgcagagt cgaatcccca agaacgatt  tgacgtcgac a cattttatc   12360 acccggacgg gaagcaccac gggcgaacaa atgcaccta  cgcctatgtt c tccaagacg   12420 atctgggcgc cttcgatgcg gccttcttca atatccaggc tggagaggcc g agagtatgg   12480 accccccagca ccggctgttg ctggagacgg tgtacgaggc cgtaacgaat g ctggaatgc  12540 gtatccagga tctgcaggga acttcgactg ctgtttacgt cggggtgatg a cgcacgact   12600 atgagactgt ctcaacccgc gacctggaga gcatcccac  ctactcggcg a cgggtgtcg   12660 cggtcagtgt tgcgtccaac cgcatctcgt attttttga  ctggcatgga c caagtgtaa   12720 gtcacccaat atcgtgtagc agtctaatca tgctctaacg gaccgggatg g ttgaaagat   12780 gacgatcgat acggcatgca gctcgtcgtt ggttgccgtt catctggcgg t gcaacagct   12840 acggacgggt caaagctcca tggcaattgc tgcgggtgcg aatctgattc t ggggcccat   12900 gacattcgtc cttgaaagca aattgagcat gctatccccc tcgggtcgat c ccgcatgtg   12960 ggacgccgga gctgacggct atgccagagg cgtgagtgtt tcttgagctc g tagatgaca   13020 gttcccatcg ctgaccgtga tcaggaagct gtttgctctg tagtgttgaa g acattgagt   13080 caagccttgc gcgatgggga cacgattgaa tgtgtcatcc gagaaactgg g gtgaatcaa   13140 gatggccgaa cgaccggaat tacgatgcca aaccatagtg ctcaggaggc a ctcatcaag   13200 gctacctacg cccaggctgg ccttgacatc accaaggccg aggacaggtg c caattcttc   13260 gaggctcatg gtcagcaaag agaacctgtt ctgttggcgc cctgcagctg a cattcgtat   13320 gatagggact ggtactccgg ccggagatcc ccaggaggcg gaggccattg c aacagcctt   13380 cttcggccac gagcaggtag cacgcagcga cggaaacgag agggcccctc t gttcgtggg   13440 cagtgcgaaa actgttgtcg ggcacaccga gggcacggcc ggtctggctg g tctcatgaa   13500 ggcgtcgttc gctgtccgcc atgggtaat  cccccccaac ctgctgttcg a caaaatcag   13560 cccgcgagtc gccccattct ataaaaacct gaggattccg acagaagcta c ccaatggcc   13620 agctctccca cccggacaac cgcgccgcgc cagtgtcaac tcctttggta a gcgaggatt   13680 gcccggagga accctcacaa gtactcgaat taatgctaac tgaaccgcgc c gatggacag   13740 gattcggcgg cacgaatgcg catgccatta ttgaggaata catggagcca g agcaaaacc   13800 agctgcgagt ctcgaataat gaggactgcc cacccatgac cggtgtcctg a gtttaccct   13860 tagtcctctc ggcgaagtcc cagcgctcct taaagataat gatggaggag a tgctgcaat   13920 tccttcagtc tcaccccgag atacacttgc acgacctcac ctggtcctta c tgcgcaagc   13980 ggtcagttct accccttccgc cgggctattg tcggccatag tcatgaaacc a tccgccggg   14040 ctttggagga tgccatcgag gatggtattg tgtcgagcga cttcactacg g aggtcagag   14100 gccagccatc ggtgttggga atcttcaccg ggcaggggcc gcagtggccg g ggatgttaa   14160 agaatctgat agaggcatcg ccatatgtgc ggaacatagt gagggagctg g acgactccc   14220 tgcagagctt gccggaaaaa taccggccct cgtggacgct actggaccag t tcatgctag   14280 aaggagaggc ctccaacgtc caatatgcta ctttctccca gccattatgc t gcgcggtgc   14340 aaattgtcct ggtccgtctc cttgaagccg cgagaatacg attcacggct g ttgttggac   14400 atagctccgg cgaaattgct tgcgcctttg ctgccgggct catcagtgcc t cgttggcga   14460 ttcggattgc ttacttacgt ggagtcgtct cggcaggggg cgccagaggc a caccgggag   14520 ccatgttggc cgccgggatg tccttttgagg aagcacaaga gatctgcgag t tggatgcct   14580 ttgagggccg catctgcgtg gctgccagca attcccaga  cagtgtaact t tctctggcg   14640 acgcgaacgc aattgatcac ctgaagggca tgttggagga tgagtccact t ttgcgagac   14700
```

```
tgctcaaggt cgatacagcg taccactcgc atcatatgct tccatgtgca g acccatata   14760 tgcaagccct agaagagtgt ggttgtgctg ttgccgatgc aggttcccca g ccggaagtg   14820 taccctggta ttcgtccgtg gacgccgaga acaggcaaat ggcagcaaga g acgtgaccg   14880 ccaagtactg gaaagataac ttagtatctc cggtgctatt ctcccacgca g tgcagcggg   14940 cagtcgtcac gcacaaggcg ctggatatcg ggattgaagt gggctgtcac c cagctctca   15000 agagcccatg cgtcgccacc atcaaggatg tcctatctgg ggttgacctg g cgtatacag   15060 gttgcttgga gcgaggaaag aatgatctcg attcattctc tcgagcactg g catatctct   15120 gggaaaggtt tggtgcctcc agtttcgatg cggacgagtt catgcgtgca g tcgcgcctg   15180 atcggccctg tatgagtgtg tcgaagctcc taccggccta tccatgggac c gctctcgtc   15240 gctactgggt ggaatcccga gcaactcgcc accatcttcg agggcccaag c cccatcttc   15300 tattaggaaa gctctccgaa tacagcactc cgctaagctt ccagtggctg a attttgtgc   15360 gcccacgaga cattgaatgg cttgatggac atgcattgca aggccagact g tcttccctg   15420 cggccggcta tcgtcatg gcaatggaag cagccttaat gattgctggc a cccacgcaa   15480 agcaggtcaa gttactggag atcttggata tgagcattga caaggcggtg a tatttgacg   15540 acgaagacag cttggttgag ctcaacctga cagctgacgt gtctcgcaac g ccggcgaag   15600 caggttcaat gaccataagc ttcaagatcg attcctgtct atcgaaggag g gtaacctat   15660 ccctatcagc caagggccaa ctggcccaa cgatagaaga tgtcaatccc a ggacgactt   15720 ccgctagcga ccagcaccat cttcccccgc cagaagagga acatcctcat a tgaaccgtg   15780 tcaacatcaa tgcttcctac cacgagctgg ggttgatggg gtacaactac a gtaaggact   15840 tccggcgtct ccataacatg caacgagcag atcttcgagc cagcggcacc t tagacttca   15900 ttcctctgat ggacgagggt aatggctgtc ctctcctgct gcatcctgca t cattggacg   15960 tcgccttcca gactgtcatc ggcgcatact cctccccagg tgatcggcgt c tacgctgtc   16020 tgtatgtacc cactcacgtt gatcgcatca cacttgtccc atccctttgc c tggcaacgg   16080 ctgagtccgg atgcgagaag gttgccttca atactatcaa tacgtacgac a agggagact   16140 acttgagcgg tgacattgtg gtgtttgacg cggagcagac caccctgttc c aggttgaaa   16200 atattacttt taagcccttt tcaccccccgg atgcttcaac tgaccatgcg a tgtttgccc   16260 gatggagctg gggtccgttg actccggact cgctgctgga taaccgggag t attgggcca   16320 ccgcgcagga caaggaggcg attcctatta tcgaacgcat cgtctacttc t atatccgat   16380 cgttcctcag tcagcttacg ctggaggagc gccagcaggc agccttccat t tgcagaagc   16440 agatcgagtg gctcgaacaa gtcctggcca gcgccaagga gggtcgtcac c tatggtacg   16500 accccgggtg ggagaatgat actgaggccc agattgagca ccttttgtact g ctaactcct   16560 accaccctca tgttcgcctg gttcagcgag tcggccaaca cctgctcccc a ccgtacgat   16620 cgaacggcaa cccattcgac cttctggacc acgatgggct cctgacggag t tctatacca   16680 acacactcag cttcggaccc gcactacact acgcccggga attggtggcg c agatcgccc   16740 atcgctatca gtcaatggat attctggaga ttggagcagg gaccggcggc g ctaccaagt   16800 acgtgttggc cacgccccag ctgggggttca acagctacac atacaccgat a tctccaccg   16860 gattcttcga gcaagcgcgg gagcaatttg ccccccttcga ggaccggatg g tgtttgaac   16920 ccctcgatat ccgccgcagt cccgccgagc agggcttcga gccgcatgcc t atgatctga   16980 tcattgcctc caatgtgcta catgcgacac ccgacctaga gaaaaccatg g ctcacgccc   17040
```

```
gctctctgct caagcctgga ggccagatgg ttattctgga gattacccac a agaacaca    17100 cacggctcgg gtttatcttt ggtctgttcg ccgactggtg ggctggggtg g atgatggtc   17160 gctgcactga gccgtttgtc tcgttcgacc gctgggatgc gatcctaaag c gtgtcgggt   17220 tttccggtgt ggacagtcgc accacggatc gggacgcaaa tctattcccg a cctctgtgt   17280 ttagtaccca tgcaattgac gccaccgtgg agtacttaga cgcgccgctt g ccagcagcg   17340 gcaccgtcaa ggactcttac cctcccttgg tggtggtagg agggcagacc c cccaatctc   17400 agcgtctcct gaacgatata aaagcgatca tgcctcctcg tccgctccag a catacaagc   17460 gcctcgtgga tttgctagac gcggaggagc tgccgatgaa gtccacgttt g tcatgctca   17520 cggagctgga cgaggaatta ttcgccgggc tcactgaaga gaccttcgag g caaccaagc   17580 tgctgctcac gtacgccagc aatacggtct ggctgacaga aaatgcctgg g tccaacatc   17640 ctcaccaggc gagcacgatc ggcatgctac gctccatccg ccgggagcat c ctgacttgg   17700 gagttcatgt tctggacgtc gacgcggttg aaaccttcga tgcaaccttc c tggttgaac   17760 aggtgcttcg gcttgaggag catacggatg agctggccag ttcaactaca t ggactcaag   17820 aacccgaggt ctcctggtgt aaaggccgcc cgtggattcc tcgtctgaag c gcgatctgg   17880 ctcgcaataa ccgaatgaac tcctcgcgcc gtcccatata cgagatgatc g attcgtcgc   17940 gggctcccgt ggcattacag acggctcggg attcatcatc ctacttcttg g agtccgctg   18000 aaacctggtt tgtgcctgag agtgttcagc agatggaaac aaagacgatc t atgtccact   18060 ttagctgtcc ccatgcgctt agggtcggac agctcgggtt tttctatctt g tgcagggtc   18120 acgtccagga gggcaatcgc gaagtgcccg tcgtggcctt agcagagcgt a acgcatcca   18180 ttgtgcacgt tcgtcccgat tatatatata ctgaggcaga taacaatctg t ctgagggtg   18240 gtggcagcct tatggtaacc gtcctcgccg cggcggtgtt ggcggagacg g tgatcagta   18300 ccgccaagtc cctgggggta actgactcaa tcctcgttct gaatccccc a gcatatgtg   18360 ggcagatgtt gctccatgct ggtgaagaga tcggtcttca agttcatctg g ccaccactt   18420 ctggcaacag gagttcggtt tctgctggag acgccaagtc ctggctaaca t tgcatgctc   18480 gcgacacgga ctggcacctg cgacgggtac tgccccgggg tgtccaggct t tagtcgact   18540 tatcagccga ccagagctgt gaaggtttga ctcagaggat gatgaaagtt c tgatgcctg   18600 gctgtgccca ttaccgtgcg gcagacctgt tcacagacac cgtttccact g aattgcata   18660 gcggatcgcg gcatcaagct tcactgcccg ccgcatattg ggagcatgtg g tatccttag   18720 cccgccaggg acttcctagt gtcagcgagg ggtgggaggt gatgccgtgc a ctcaatttg   18780 cagcgcatgc cgacaagacg cgcccggatc tctcgacagt tatttcctgg c cccgggagt   18840 cggacgaggc tacgcttcct accagggttc gctccattga cgctgagacc t ctttgcgg   18900 ccgacaaaac atatctcctg gtcggactga ctggagatct tggacgatca c taggtcgtt   18960 ggatggtcca gcatggggcc tgccacattg tacttacgag cagaaatccg c aggtgaacc   19020 ccaagtggct ggcgcatgtt gaagaactgg gtggtcgagt cactgttctt t ccatgtaag   19080 aggagtcctt ccttctgcaa ttcctcctta tgatcccgac taacgcagct g gcttcaggg   19140 acgtgacaag ccaaaactca gtggaagctg gcctggctaa actcaaggat c tgcatctgc   19200 caccagtggg gggtattgcc tttggccctc tggttctgca ggatgtgatg c taaataata   19260 tggaactgcc aatgatggag atggtgctca accccaaggt cgaaggcgtc c gcatcctgc   19320 acgagaagtt ctccgatccg accagtagca accctctcga cttcttcgtg a tgttctcct   19380 cgattgtggc cgtcatgggc aacccgggtc aggctaacta cagtgcggct a actgctacc   19440
```

-continued

```
ttcaagcgct ggcgcagcag cgagttgcat ccggattagc agtacgtttt c actccatcc   19500
tttgctaaac actcctatgg gcctttacta aaccgggcag gcgtccacca t cgacatcgg   19560
tgccgtgtac ggcgttgggt tcgtcactcg ggcggagctg gaggaggact t taatgcaat   19620
tcggttcatg ttcgattcgg ttgaggaaca tgaactgcat acactgtttg c tgaggcagt   19680
ggtggccggt cgacgagccg tgcaccagca agagcagcag cggaagttcg c gacagtgct   19740
cgacatggct gatctggaac tgacaaccgg aattccgccc ctggatccag c cctcaaaga   19800
tcggatcacc ttcttcgacg accccgcat aggcaactta aaaattccgg a gtaccgagg   19860
ggccaaagca ggcgaagggg cagccggctc caagggctcg gtcaaagaac a gctcttgca   19920
ggcgacgaac ctggaccagg tccgtcagat cgtcatcggt aagttgagcg a atccgggga   19980
atattctccc cttcctcact cagcggactg gagattaacc gcttcttttc t tttggcaga   20040
tggactctcc gcgaagctgc aagtgaccct gcagatcccc gatggggaaa g cgtgcatcc   20100
caccatccca ctaatcgatc aggggtggga ctctctgggc gcggtcaccg t gggaacctg   20160
gttctccaag cagctgtacc ttgatttgcc actcctgaaa gtgcttgggg g tgcttcgat   20220
caccgatctc gctaatgagg ctgctgcgcg attgccacct agctccattc c cctcgtcgc   20280
agccaccgac gggggtgcag agagcactga caatacttcc gagaatgaag t ttcgggacg   20340
cgaggatact gaccttagtg ccgccgccac catcactgag ccctcgtctg c cgacgaaga   20400
cgatacggag ccgggcgacg aggacgtccc gcgttccac catccactgt c tctcgggca   20460
agaatactcc tggagaatcc agcagggagc cgaagacccc accgtctta a caacaccat   20520
tggtatgttc atgaagggct ctattgacct taaacggctg tacaaggcgt t gagagcgt   20580
cttgcgccgc cacgagatct tccgcacggg gtttgccaac gtggatgaga a cgggatggc   20640
ccagctggtt tttggtcaaa ccaaaaacaa agtccagacc atccaagtgt c tgaccgagc   20700
cggcgccgaa gagggctacc gacaactggt gcagacacgg tataaccctg c cgcaggaga   20760
caccttgcgg ctggtggact tcttctgggg ccaggacgac catctgctgg t tgtggctta   20820
ccaccgactc gtcggggatg gatctactac agagaacatc ttcgtcgaag c gggccagct   20880
ctacgacggc acgtcgctaa gtccacatgt ccctcagttt gcggacctgg c ggcacggca   20940
acgcgcaatg ctcgaggatg ggagaatgga ggaggatctc gcgtactgga a gaaaatgca   21000
ttaccgaccg tcctcaattc cagtgctccc actgatgcgg ccctggtag g taacagtag   21060
caggtccgat actccaaatt tccagcactg tggaccctgg cagcagcacg a agccgtggc   21120
gcgacttgat ccgatggtgg ccttccgcat caaggagcgc agtcgcaagc a caaggcgac   21180
gccgatgcag ttctatctgg cggcgtatca ggtgctgttg gcgcgcctca c cgacagcac   21240
cgatctcacc gtgggcctcg ccgacaccaa ccgtgcgact gtcgacgaga t ggcggccat   21300
ggggttcttc gccaacctcc ttcccctgcg cttccgggat ttccgccccc a tataacgtt   21360
tggcgagcac cttatcgcca cccgtgacct ggtgcgtgag gccttgcagc a cgcccgcgt   21420
gccctacggc gtcctcctcg atcaactggg gctggaggtc ccgtcccga c cagcaatca   21480
acctgcgcct tgttccagg ccgtcttcga ttacaagcag ggccaggcgg a aagtggaac   21540
gattgggggt gccaagataa ccgaggtgat tgccacgcgc gagcgcaccc c ttacgatgt   21600
cgtgctggag atgtcggatg atcccaccaa ggatccgctg ctcacggcca a gttacagag   21660
ttcccgctac gaggctcacc accctcaagc cttcttggag agctacatgt c ccttctctc   21720
tatgttctcg atgaatcccg ccctgaagct ggcatgatgg cgcaaacata g aacatgata   21780
```

```
gcgcagcagg gacgatgtag atagagcttt gcttctgcgg gtggatctat a atatagtat    21840
atataaatat ggtgagccga acgaagaggg gggaatgcca caattattta c tgttttgcg    21900
ccgtacacga ggagaagacg tccagaacaa cataaatata tcactctagt g agacaccat    21960
atattcggag agactataaa aatatacatc tactccaatg tctggccgt c acacacagc     22020
ttacgaaaac gattaatgac ctccaacacg tcgcgcggtc gattgggaaa c tgatgctgc    22080
ccagcaaact ccaatacctg cgcctctcgg ggggagaaat ggcgcgccac c agcatcttc    22140
gatcctgcga gcgcaaaatc atcgcgaccc tgcagatgta atgtcggtat c gaatgacc    22200
agttcctcct gccactcggt atctttgctg tcgttgtcgt cgtcatggtt c ttcatcact    22260
tcgttcctca tatactggct tgcctcgtct tgataccagg gacagatcaa c agcgcaaca   22320
ctcatccggg gcaaccaggg caggtgaccc atctgctgct gccagaggag c aaggtcgtc   22380
accagggcac cttcggagaa accgatagca cccacgatag ggatgtgggg g tgttgagtc   22440
tgccagtcga caatggtgcg gcggatgggg tcgtggacgg cggcgaggcg t tcgctcacg    22500
gagggtccat tatgattgtt gtcgctgctg ctttcaaacc aggagtaata t ggccctagg    22560
tcggcgaaga cggggagaat cccaggccct gcagaggaag ggaacggagc t gtcacgtag    22620
acgaattcaa agttttcgcg cagcgcagcc cggagcttag acaattgcac g cggaagatg    22680
gcgggagagc agccagcccc atggatgcaa agaagcgctc gaggcgcctt c accagcgct    22740
ggagatgctt ggtaacgcat ggaggagggt acaatgggac tatatcctgg a tgcaagacg    22800
gggatgaggg agtgtcgagc ttacgcgttc accagcgatg aaccgctatt a ttgcaacgg    22860
aatatcctgt ctaacactct gcatctactc caggtggacg ggacaagcca g cgatgccga    22920
ttacatccat aggaacagca gtttgttcgg aacttccgct tcatccctc g atatcgggc     22980
gcaggatgcc ggcgccgaat aacgccgcac aaacccgaac gggtctgcag g tgatcccga    23040
agccctaatc caaggatcgt ccgtccttct gtctatgtct ttccgcatat g taggccgca    23100
gcgtaccaga tacgtcactc aacagttaac cagagaagac gaccgtgaca g actgccatg    23160
ggcgaccagc cattcattcc accaccgcag caaacagcgc tgacggtaaa t gaccatgat    23220
gaagtcaccg tctggaatgc cgcaccctgc cccatgctgc cccgcgacca g gtatacgtc    23280
cgcgtcgagg ccgtggcgat caatcccagt gacacgaaga tgcgcggaca g tttgccacg    23340
ccctgggcgt ttctcggaac ggactatgcc ggcacggtcg tcgcagtggg t tcggacgtg    23400
actcatatcc aagtgggtga ccgggtctac ggggcacaga acgagatgtg c ccacgcacc    23460
ccggatcagg gggcattctc gcagtacacg gtcacgcgag gccgtgtttg g gccaagatc    23520
cccaagggct tgtcgttcga gcaggctgcc gcgctacctg cgggcatcag t accgctgga    23580
ttggcgatga agttgcttgg gctgcctttg ccatcgcctt cggcagacca g ccacccacc    23640
cactccaagc cggtgtatgt gttggtctat ggggcagta cggccactgc c actgtcact    23700
atgcaaatgc tccgcctgta atgcttccct tgtcctgaga cttttctctc c gttggtcgt    23760
gggctgtaca agcgatggtt atactaagat ccgctggcag gtccggatat a ttccaattg    23820
caacatgctc cccccacaat ttcgacctgg ccaaatcgcg cggcgcagag g aggtctttg    23880
actatcgggc cccgaatctc gcgcagacga tcgtcagtga accctgcca c cgctctacc     23940
cctcccagtc cactttggcc ttacagaaca gactattgat attcttctag c gtacctaca    24000
ccaagaacaa tctccgctat gctctcgact gtatcaccaa cgtcgagtcc a ccacattct    24060
gcttcgcagc catcggccgc gcgggggggc actacgtctc cctgaacccg t tccctgaac    24120
acgcggccac gcgcaagatg gtcacgaccg actggaccct ggggccgacc a tctttggcg    24180
```

```
agggatcaac ctggcccgcc ccctatgggc gtcccggcag tgaggaagag c ggcagttcg   24240 gcgaggatct gtggcgcatc gcggggcagc tcgtcgaaga tggacgcctc g tccatcatc   24300 cgttgcgcgt ggtgcagggc ggcttcgatc acattaagca aggcatggag c tcgtccgga   24360 agggagagct gtcggggag  aaactcgtgg ttcggctcga ggggccgtaa a ctggattgc   24420 gcgttacgtc gagggagcaa gaaagctcca attttttctat caaccaatcc g tagacgcta   24480 aaacgtacat gggatattgc tgcgtggatt gggataaatc acgagtgata c acagggtgg   24540 ggttttaaga atacattgaa cacatactca gacaactctt tatgaactga t atacactac   24600 ttgctctctg ggaagatccc tgtccccagt atatcataga ttaagagaaa a aaaaaaaa    24660 acatccacgt catataccta taactatcgc tatatatata gatatatata t atatctata   24720 tatatgttag caagctcatt gtcttctaca gaacttaata atcgaaatac a aatagccaa   24780 tatcatcccc ggcatggctg ctatgcggat taaccctgct ggtactgcgc a tagatggca   24840 tgctcgaatg tgcgtgtcag atcacgacag accgggtcat tccagggttc c agttggaag   24900 aacgcaaggg tgcacaggcc ggctttgggg tcgatttgct aattacaata g cacttagta   24960 ggctggatca acattgaagg tgacataaac caaaggaatc taggagccga g cttacccac   25020 acaatgtttg ggccacccc aaaggtcaag gaaccttttc ggcgccagtt c tctccgtcc   25080 agatcctcca aggcgatgat ccccccagc ccaaagctgc gacgaaggac c atgggcatc   25140 ggcccaccgt agttgatatg tgggctggcg tccatgtgct ggttcatctg c tcttcgagt   25200 cgcggctcga gggcaggctg aaacatcaag tccacggtct gtggctgcag c aggagcccg   25260 tctcgcttca acagcgagtg aagcaccttc atataggacc cagggcccga g aacacccc    25320 tggccgccga agcactcctc tccatcggcc cggaagtaga ccgagtcgtc g tagcgcagg   25380 cgcccatccg ccgagttgcg gtgcgttgg tcggcccggc gcgcaagcat a tccggccgt    25440 tgctgcagct taaaggtcat gtcggtgatg cccagcggcg cacagatatt c cctgcagg    25500 tactgctcca ggtcgaggcc ggtggcccgc tcgacgagct taccgcccca g tccaggttg   25560 gcgccgtaga tccactccgc cccagggtcg ttgacggccg gcggcgccag g cgactctgg   25620 atgccaaact tttctgccga ctggaggtgg ccctgggcca tgtattcccg g agcaacgga   25680 tggaggaaga cgtacgacag tcccgatgta tgcgtcagca ggtgccgcag c gtgatcttc   25740 ccccgacgct ctcgcaatct tgcgtttccc gcgtcgtcaa accctccag c acgggcatc   25800 gcgctcaaat ccggaagcag cctatccacc gtctcatcca agtccacgag a ccgcgctcc   25860 atgcattgta gggccatgat cgtggtcagc agcttggtcg cactggcgag c cggcagggg   25920 gtgtcgacct gtagcggcgg cagctgattg cactcgtccc gtcgcaccgt c cgagccccg   25980 aagcagcgcg tataatttag attgcctagg tatgtcccgc tgtcattcgt c tcggtgtgc   26040 ttgtaattgt cgcaaagggg tccgattggg gtctctcacc actgcaatct c gggccatga   26100 tgaccgcccc ggggatctgc ctggatttca ggccttgcg  gaaggcggtt t ccatcagaa   26160 caaccggatc cgctgccgca gcagcatcaa tgatggatcc cattctgaat t ttttaattt   26220 ttttcccttt ttactaataa ataaatagat gaaataggg  aataaaaata a aaccaaaaa   26280 gaaagaaaat cggcgctta  ttttgtctgc ggctggggcc atagatcgga c cttacctac   26340 ctatccaagg gcgatcatcg gatcgggccg gcggatcgtt acatcaggcc g tccccgaa    26400 taagaccgac tcggtgactt tcggtgttat gcgccgctag gaacggtatt g tcttagact   26460 ctgtattgta aaagctacct aacctcactt aggtaggtag gtaggtacct a ggtactctc   26520
```

```
cagctgtatc ttacgtacag gtccgtgata ctactacctt acctacctaa g ttacatgac    26580 aaggtaggta cttttctacg taggtaggta tttttatatt cgatttgcac g aaatggatg    26640 tctcccgcat gttctaagat taccacatat accggtgttc taattgctcc g tactctgta    26700 ccggagatag cgtcctttga agctgccccg agaatcaatc acagcgatcc c ttcatttct    26760 tgactgtggc acccgcactg cgattgtgtt gcatatgggc attgaccaag t gacccgccg    26820 caagagccgc gcaggtactt aactcgccag ccagcacggc cgcggcgaca a tgcgggcca    26880 agcggcgcgc attggcgcca ggctccgtgg aatgtgcgcc ccggacacct a gcaagtcca    26940 acatggctcc ctgggcctca agaatggtgc ctccgccaat cgtgccgacc t ccatcgagg    27000 gcatcgagac agcgatgtgc aggtttccat cgatgctaga aacccaccat t agcaaacac    27060 acccacgtga atatatataa ccgggaggag aaaatcaaaa cgtagagaag c tacctactt    27120 tttcatggtc gtaatgcaac tactgctctc cacattctgc gccggatcct g accagtggc    27180 cagaaacacc gcctggacga ggttggaggc atgggcgttg aagccgccca g gctgcccgc    27240 catggcactc ccgaccaggt tcttggccgt gttgagctcg accagcgcat c gacgtcggt    27300 cttcaggacc tgtcggacag tctccgcggg gatcgtggct tcggcgatga c ggacttgcc    27360 gcggccgccg atccagttaa tggcggcgga tttcttgtcg aacagaaat t gccagataa    27420 ggtaaccgta tgcatgtcgg gaaatccacc ctcgcggcc atcgcctcca g gcttttc    27480 aacgcccttc gaaatcatat tcatgcccat cgcgtcgccc gtggtggtgc g gaaccggat    27540 gtagagatag atgcccgcct gggccaccgt cagggtttgg agccgcgcaa a ccggctggt    27600 cgcgttgaag gcggccgcca gaacctcgtg cccgagagga gactcaaccc a gcgctgggc    27660 ttcagctgca cgttgggccg acgggaatcg cagacaggga ccacgcgtca t accatcacc    27720 tttgagcatg gtagtggcac cgccgccagc attgatcgct ttgcatccgc g actggcgct    27780 cgcaacgagc acgccctcgg ttgtggccat gggaatgaac aacgcctgtc c atcgatcac    27840 catgggtccg gccactccca ggggcagagg caggtacccg accacgttct c acagcaggc    27900 gccatgcaca agctcgtagt tatagtcgcg ataagggagc aatgactccg c caggccgct    27960 gcagaggttc tgagtggagg gcgttttcga cacagcggca cggcgaatcc g cacggcacg    28020 cgtaaatgcc tccagccggg tcaccgagcg ggatgatccc gccgcaatcc g ctcgagagt    28080 cttctctaaa ctgtaccccg cgatcttacc ccggagacac agttccacca g ctcgtcgtc    28140 cgtcagagat tctgcttggt tcgatttgag gagggcctct gtttcttctg g ggggcgagt    28200 acagacttca ggggcagtgg cagagcatgg caccgacaag taggagccat c agggacggc    28260 ggactctctc gcttggggcc aagcatgcca gcgagcagcg tggatcaggt g gttgttgag    28320 gaccaggcta acgaccaatg cgcccatgag acatagtcga cccagcgggc t ttccaatcc    28380 atcgagcaca ccgtcaaatg tagaacgttt agtggctgat atattgaacc c agctgattc    28440 caagacgtac tgcagtggcg gcagaacggt tacgcgtgtc tcaaacccct c gacgcgcgc    28500 cgttaggtag atctcgttga gtccgttggc cgcttctttg aaaggactga c agcagtagg    28560 gggcagagta ccattagcca tatattctcc catgacccga tagaagaagg g cgacaattg    28620 gaggaagtga catagaacga agccgcccac cgtcaatagc ttccaccagg t gatgtttgt    28680 cgacttgacc ttgtgcccaa aaatccccga aggatgcttg gcattaactt g accaagccc    28740 tcctgggctc cggattcgcg tgatctctaa tttcacgcaa agaatggtgg c atagaaggt    28800 aaaagtaga acgcatcaa tcaggagtgt ccatgccgcc aggaagcaaa a atggccaag    28860 actatccttt ggccgaagga ccgcccctaa tgccaacgcg ccgatttcca g gaggtaaga    28920
```

```
tcgcacaata taccacccct ctcgatcaac cgcgagttgg atgatgttag g aatcaattg   28980 gttttgccgg ctatcatcac tgctggcgcc attgggaact tgccgctgcc c cccgcccca   29040 cagttcttcc gacacgcaga gaacagcacg ggttagttgg atcggcttct c aaagcccac   29100 tgtcagaacg aggtacggga ttccttcgaa aagaagaagc atgtcgacgg g cacgtcgca   29160 tgtagtcgtg attccaagcc cgagtacaaa agcaaaggca ccagacagca g gaccgaggc   29220 tgccaaccag aagcgtgagc cgaggtggcg catcacccga agagagaga c cacagtcat   29280 attcatggct aggtaactga gccctatgat caccaagtcg actgtctccg c atggtgaac   29340 acgatgaagg aatgacagcc atgagcttcc gagccagtgt cccagtgacc t gggacttcc   29400 ttcttcgcga ggagacctca gtctccaact atcatcctct ttttccgagg g tataatttc   29460 gacagcctgt agaaagccat ctagttggga gtagggaact cgaaacgtca a cgcggaatg   29520 atcgggtgag gggatgaat cggggtggg cgtggtctgt tccgcaccga g gaaccctga   29580 gagcgtgttt gataggaagg ggatactggc gtcgacagac gcacccggta g atcgagggt   29640 gacaagagcc cagtgaaagt cagactaatt gagagtagca cagggacggt c cggtcagca   29700 cgcagaattt ctcggaccaa tggagcgcag gagatctatc ataccctggcc a tcctccggc   29760 accttaggtc ggtcgtctat ctgccatttc catgcgctag cctctcccag g ctaacagtg   29820 cggcttcccc agagaaatga ctggacgttc aagggggttt ccttggccca g ggggccaga   29880 cctctgtgag tagcctgata tgtcccttcc agcacatgaa gatgggtcgt t gccgcggtc   29940 agcgccgtga ctagcagagt gtgaatggga tgtcgacacg cgtgtcccac a atggcacgc   30000 aatgctttgg tcactcgatg ctgcacccg ccagggtccg gctttctaac c accggatcc   30060 attgcgatga ctctcttggt gcgcgagaga ggggtgtgag tgcttgtgga t gatgtaaag   30120 acaagtacaa gattcgcaga aaggtcaaag agactagaaa aaaataaaat a aaaaaatta   30180 aaataaaatt aaaaaaaacc cctaaagaac aagaaaagaa gagagaaaga a agagagaga   30240 gagagagaac caagcctcag ggaaggaagg aaataagcca aggcaactcg c ttggtgcga   30300 cccaatgcta ggaggtccat gagactccgg tacttcctgg taatattgag c caaatatac   30360 ttattctagg taggcggtag ggatttaat gcgtatgcct atgatacaat a atggtacat   30420 gaaggcgact gcacaaacaa tcttacgccg tttggctcgc tggctagaag a gtaagcact   30480 aaacaaggcc agggttgggg aaatcttctc cactgtcaga cgtccttcgt a ccttagagg   30540 tactacctta ccgaggtaag gtactttatc tgaacacgga attacatcct c ttaccacga   30600 attttcagat ctcccaattt tgtaggttat gaaatattga aatttattga c ctgcccccg   30660 tccattggct aggtattaca cacggctgta tctctatctc atagaatggt a tctagtacg   30720 ctcttttcga tattacaaag gtggcttttt caggaaattt ggaaatatcc a gtgggaaga   30780 gggtgtacgt actctagtag gtaaggtacc ttacctacct taccttctgg a gtcctggta   30840 agattgtttg tgtaatgaat cgatcagctt agtgcgctaa aattcggtca c cctgtagaa   30900 acataacaat atttcctttc ttcagcccct acctaaatta ggtgttcaaa g ccaaggagt   30960 aatacatacc gtcagtattt ctaggttggc aggagggatt tgatgctgt c acccttggc   31020 gcatcatgca cgattcatga aacagactgc actatccgtc ttacgcgcct t agcgccgcg   31080 gctgaacgag taagcactca gccaaggagc ccacccctc ccggcccac c ccctggcag   31140 ggctgtcaaa gcggatcgag tctcattggg tttgcttatc aaaatcggtt g gtaatccag   31200 gtagcagtag catctggatg taaactaata aaaggcaga ctgtcgggac c ttaaaaggc   31260
```

-continued

```
caaagaggta cccatgcccg ggttcttcgg tcgccagaac tgcaatgtat c aaatgtctg    31320 atgctcatga cccaggacac agcacagtac aggggggcaa tggctgcaga t caaggtata    31380 ttcacgaact cggtcactct ctcgccagtg gagggttcac gcaccggtgg a acattaccc    31440 cgccgtgcat tccgacgctc ttgtgatcgg tgtcatgcac aaaagatcaa a tgtactgga    31500 aataaggagg ttactggccg tgctccctgt cagcgttgcc agcaggctgg a cttcgatgc    31560 gtctacagtg agcgatgccc aagcgcaag ctacgccaat ccagggcagc g gatctcgtc     31620 tctgctgacc cagatccctg cttgcacatg tcctcgcctc cagtgccctc a cagagcttg    31680 ccgctagacg tatccgagtc gcattcctca aatacctccc ggcaatttct t gatccaccg    31740 gacagctacg actggtcgtg gacctcgatt ggcactgacg aggctattga c actgactgc    31800 tgggggctgt cccaatgtga tggaggcttc agctgtcagt tagagccaac g ctgccggat    31860 ctaccttcgc ccttcgagtc tacggttgaa aaagctccgt tgccaccggt a tcgagcgac    31920 attgctcgtg cggccagtgc gcaacgagag cttttcgatg acctgtcggc g gtgtcgcag    31980 gaactggaag agatccttct ggccgtgacg gtagaatggc cgaagcagga a atctggacc    32040 cgtgcgtcgc cgcattcccc aactgcttcc cgtgagagga tagcacagcg c cgacaaaac    32100 gtatgggcaa actggctaac agacttgcat atgttctcac tagatcccat c ggaatgttt    32160 ttcaatgcgt cacgacggct tcttactgtc ctgcgccaac aagcgcaggc c gactgccat    32220 caaggcacac tagacgaatg tttacggacc aagaacctct ttacggcagt a cactgttac    32280 atattgaatg tgcggatttt gaccgccata tcggagttgc tcctgtcgca a attaggcgg    32340 acccagaaca gccatatgag cccactggaa gggagtcgat cccagtcgcc g agcagagac    32400 gacaccagca gcagcagcgg ccacagcagt gttgacacca taccttcttt agcgagaac     32460 ctccctattg gtgagctgtt ctcctatgtt gacccctga cacacgccct a ttctcggct     32520 tgcactacgt tacatgttgg ggtacaattg ctgcgtgaga atgagattac t ctgggagta    32580 cactccgccc agggcattgc agcttccatc agcatgagcg gggaaccagg c gaggatata    32640 gccaggacag gggcgaccaa ttccgcaaga tgcgaggagc agccgaccac t ccagcggct    32700 cgggttttgt tcatgttctt gagtgatgaa ggggcttcc aggaggcaaa g tctgctggt     32760 tcccgaggtc gaaccatcgc agcactgcga cgatgctatg aggatatctt t tccctcgcc    32820 cgcaaacaca acatggcat gctcagagac ctcaacaata ttcctccatg a accaatcca     32880 gcctttggaa gtgtgtgcaa ccactgcgta gcgcccctgtc attcggtgcc g gacagagtc    32940 tctcagtggg gtgggaagat ataggaaatc ggacatcgcc acatcgactc t tacacccac    33000
```

<210> SEQ ID NO 19
<211> LENGTH: 31328
<212> TYPE: DNA
<213> ORGANISM: Aspergillus terreus

<400> SEQUENCE: 19

```
ctaccacgaa acttcagatt ttcctatttc acggccttta gaatactgac a tccgttgat     60 cttccctat tttctgtgag gtagtaagtg tggcagtatc tccctcctat a tttggcagg     120 ctcttttcaa tattatatat agaagtggcc ttttcttaga aattggaatt t cctggcgag    180 agggcgtcgt ctgagactct agtcacttcc aactattgca gctacatgga g gagtacctg    240 ttgactaagt tgtactctgt gatttgtttg ataaacactc aataggtttc t agcacgttc    300 cagttgtagc tgagcactca actagctaac gggtgagaac attgaagcgt c aattcttt    360 tacccggaat acttttaaca gctatgtatg gttatttggg accggggaag g aattaaatc     420
```

-continued

```
acgcagggct tcttcttcac tcccatgcga cctactcaca ttgtgttcaa a gtacggac      480
gtgtctggat caatggctcc gacagacggc caagaaaacc aatgcatttg c caagaatac      540
aaatggctac gtactagtcg agtagggcgc ggtcctgctt gccgcctcca a aggaaaacg      600
ggcatttact agatttgttt gttgcaggta ttgtactcgg atagtccagc c cagggatca      660
attgactttg agacaagcag cgggccccgg cggccaatcg gcttttaagg c gggtagggg      720
tcgggtggtc tactgtatgc ggttcctccc gatcaccaca ttacgtctta c attgcatac      780
ctaggtaaat cttatggtac tgtaggtata cacaatattg gtgaaagtta c cggtaaaaa      840
gaaaatggaa aaactagaaa ggcagaaatt ttaccggtaa gataagtgaa t ttcgtttta      900
ttcgcagggc atgatggtat gataggtaca tttacgaaaa cttgaactca t gataatacg      960
gtaccacaga cagcttaggc gcccctgcat ccccttttgta ctctcgtact c catatagaa     1020
aagcttgtat gtttggctgg acctgctgcc acgagtcggc ctggtccgtc t tactacttg     1080
tatatcagag ccgctttgta aggttttggt tcgcctcggt tttgcgattc c atatgggggg    1140
cttttagggt acggaaatcc atgtaaacaa taccagctga agtacctact a ggtgccacc     1200
taggcgctaa ggtacctaag tacatcttca tcccaaaaac aaagataaag g agttctaaa    1260
ttacgttaga ttccgcattg ctgcagcgac acacgtgatt ttaggcttcc c atcaccagc     1320
aagctcacct ccaggaggcc cctttccctt ggacctgact aaggcatcgt g ttcgccggc     1380
aaccttacca taaggtagaa tgacatccca ccacggtgaa acagagaagc c acagagcaa     1440
cacggctcaa atgcagataa atcatgtcac tggcctcagg ctaggcctgg t tgtggtttc     1500
agtcactctg gtgcgtttc tgatgctctt ggatatgtcc atcattgtca c ggtcagcat      1560
ggcaccagcc tggagattgc tccgagcctt ggagacaact gactcttcac a ttcgcaggc     1620
gattcctcac attaccgccc agtttcattc cctgggcgat gtcggatggt a cggaagtgc     1680
gtatcttcta tcaaggtgat cgattttcca acccatgccc tcttcctttt c tccagccgg     1740
gtttctattg actccacgac acgtctagc tgtgccctcc aacccttggc a ggcaaacta     1800
tacactctgt tgaccctgaa atacaccttc ctcgcttttc tcgggttgtt t gagattgga     1860
tcggttcttt gcggcactgc tcgttcgtca accatgttga ttgtagggcg a gcagtggcc     1920
ggaatgggag ggtcggggct caccaatggc gcaatcacca ttctgtcggc g gcagctcca     1980
aagcaacagc aaccgcgtaa gtactgatag ccagacctat ctcaaccgtt g ttatgctat     2040
gctgacccgg atatttacac atagtcttga ttgggatcat gatgggccgt c agttcgcca    2100
acccattggg atccccggaa atcatcaagc atagtttctg actccattcc c agtaagcca     2160
aatcgccatt gtatgtggac cgttgcttgg gggtgctttc acgcagcacg c aagttggcg     2220
gtggtgtatg tatccccatt ggatttatcg gttcagtgct tgctttctca a aggacctttg    2280
gctacgactc cgccacgtca agatctttcg ctcacggtga ttctggtcca g gttttttaca   2340
tcaaccttcc cattggggcg tttgccacat ttctccttct cgtcatccag a tccccaaca     2400
gattgccatc cacgtcggat tcaaccacag acggcacaaa cccaagagaa gagggggctc      2460
gggacgtctt gacccaactg gatttccttg gattcgtgct cttcgccggt t ttgcgatca    2520
tgatatctct tgctttggag tggggtgggt ctgattatgc gtggaatagt t ccgtgatca     2580
tcggcttgtt ctgtgcggcg ggcgtgtcgc tggtgctgtt cggatgctgg g aacggcatg    2640
tcggcggtgc agtggccatg attcccattt ccgtggccag tcgtcgccaa g tctggtgct    2700
cctgcttctt cctcggcttt ttttccgggg ccctacttat tttctcctac t acctgccta    2760
```

```
tctacttcca ggcggtcaag aatgtttctc ccaccatgag tggagtgtat a tgctgccgg    2820 gcattggtgg acagatcgtc atggcgattg tgacgggtgc aatcagttga g ttgccacca    2880 ttccaccacc tttcttcgct tataacctat ggcgttactg acaaattgag g gtggtagtc    2940 ggtaaaacag gctattacgt tccgtgggcg ctcgcaagcg ggatccttgt g tccatatcc    3000 gccggactgg tatcgacctt ccagccggaa acctcgattg cagcatgggt c atgtatcag    3060 ttcctgggag gcgtgggccg aggatgcgga atgcaaaccg taggtgacct g gatcgtttc    3120 catcggtttg cgccgcactc ttatgcaaat gctcattgac tcggttgtcc c tcctttagc    3180 ctgtcgtcgc cattcaaaat gcgctgcctc cacaaacgag ccccatcggc a tttcgctag    3240 ccatgttcgg ccagacattc ggtggctcgc tttttctcac cctgaccgaa t tggttttta    3300 gcaatggttt ggactctggt ctgcgccaat atgcgccaac cctcaatgca c aggaggtaa    3360 cagccgcagg ggccaccggc ttccgccaag tggtccccgc tcctctcatc t ctcgggtcc    3420 tcttagcata cagtaaaggc gtggaccatg cattctacgt tgcggtcggt g cgtctggag    3480 ctaccttcat cttcgcctgg ggtatgggcc ggcttgcctg gagaggctgg c ggatgcagg    3540 agaaaggacg gagcgaatga atttaatcct atcgtaggga acgccaaaga a atattaata    3600 tttctatgga gatagccatg taccgtttgg caactcatac actctaccta c tcttctcaa    3660 accaaacgaa ccatttttat gacaggaaga gcaataatta atcacgaacc a gttgtgacg    3720 acagacccgt tcaactgtgg cctttttttg gcgcttcatg ggtaaacact t cagtgttga    3780 tgagattcct agcttgacct gagcagacct aaacctgcat tacctagtca t ggaaatatg    3840 cattcgaata cctgacatgt tctgttacga atccacggca tcggtatatt c aatggacat    3900 ggccttccag tatttgcttc tcttaaagaa agttccatgg ttccattgta a tggttaact    3960 gacggcttcc ttgtacacat tggccatcac aggtgatttg agcaagacag t cgaggagat    4020 caacattgag attcggtatc aagcactgat accacacaga actggcgggt a tgaagcagc    4080 ccgtcttggt agtgtggcag agaaatcgtg gcgtgtagca cctacgcttc a gagcaacta    4140 tcgcgccctc agaccgcag accaactgga gtaccggact cggcgttttg g tcggcgtta    4200 tcaaccgggg ttattgtacc gccaacccgt gcagctacct agctcactgt g gagaatgga    4260 taatgctagg cttcggtctg acgatgtcat tctattgctg atgatgttcc t ggcacccct    4320 ttatctacca tcctggcgag gtcgaatcag cccgcgtccg tcatactcca g gtgtgcgca    4380 gtaaggaagg cacatccatc aaacatcaaa ctagaagaaa ttggccacga t gacaccatt    4440 agatgcgccc ggtgcgcctg ctcccatagc tatggttggc atgggctgca g atttggcgg    4500 aggcgcaaca gatccccaga aactgtggaa attgctggag gaaggaggga g cgcctggtc    4560 taagattcct ccttcacgat tcaatgtcgg cggggtctac caccccaatg g ccagcgggt    4620 aggatcggtg agtatgaagg attctgggtt gagcattttt gaggcccata t cttcctgtt    4680 cagaacgata ggcgttgact gcgagtagat gcacgttcgc ggtggacact t tctcgacga    4740 agacccggct cttttcgatg cctcattttt caatatgagt actgaagttg c cagtgtacg    4800 tcccgcgatc gttgtccagt tgtgtatgga tcagaagcgg aataaaccca t gctaagact    4860 gccgaatagt gtatggaccc ccagtaccga ctcatacttg aagtcgttta t gaggcgctc    4920 gaagctggta tgtattatat tccttggttt cccacgtggg tattaactcc c catggctcc    4980 gcagcgggaa ttcctctcga acaggtctcc ggctccaaga ctgggttttt t gcaggaacc    5040 atgtatcacg actaccaagg ctccttccag cgccaaccag aagcccttcc a cggtatttc    5100 ataacaggaa atgctggcac catgctcgcg aatcgcgtct cccactttta t gaccttcgt    5160
```

-continued

```
gggcccagtg tctcgatcga cactgcctgt tccacaacct taacagcctt g catcttgcc   5220 attcagagct tgcgagctgg agaatctgat atggcgattg tcgctggcgc g aacctgcta   5280 cttaatcctg acgtctttac taccatgtcc aaccttgggt gagtctggtg t tcaatccat   5340 ctagtgatca gcattcttgt tgcacagaca atatgtgatg ttaactgtga t gtgctgcga   5400 ccagcttcct ttcgtccgat gggatttcct actcatttga ctcgagagcg g atggctatg   5460 gtcgcggaga aggagtggct gcgatcgtct tgaagactct gcccgatgcg g tgcgagacg   5520 gagacccgat ccgcctcata gtgcgcgaaa cggcaatcaa ccaagacggc c ggaccccag   5580 ccatcagcac gccgagcggc gaggcccagg agtgcctgat ccaagattgc t atcagaagg   5640 cccagttgga cccaaaacag acttcgtacg ttgaggccca tgggacggga a ccagagcag   5700 gagatccgct ggagcttgca gtcatctcgg ccgcgtttcc gggacagcag a tacaggtgg   5760 gctccgtgaa agccaatatc gggcatacag aggctgtcag tggtctggcg a gtttgataa   5820 aggtggctct ggctgttgaa aaggggggtta tcccgcctaa tgcaaggttc c tccagccga   5880 gcaagaagtt gctcaaggac actcatatcc aggtagcatt atcttcacga t tttttcctc   5940 tcattctatt ctttctattc cagctcctcg ctgatttaca aacagattcc a ctgtgtagc   6000 caatcatgga taccaaccga tggtgtccgt cgcgcatcaa taaacaactt c ggtttcgga   6060 ggcgcaaatg ctcatgcaat cgtggagcaa tatggcccgt ttgcagaaac a tcgatctgc   6120 ccacctaatg gttattctgg caactatgat ggcaatttag gaacggatca a gcgcatata   6180 tatgtgctga gtgccaagga tgagaacagt tgcatgagaa tggtttcaag g ctgtgcgac   6240 tatgctaccc acgccagacc agccgacgat ttgcaattgc tcgcgaatat a gcatacacg   6300 cttggttctc gtcgctcgaa cttccgatgg aaggcagtat gtacggcaca c agcctcacg   6360 ggtcttgccc agaatttggc gggagaaggc atgcggccaa gcaagtcagc c gaccaagta   6420 agactgggat gggtgttcac aggccaggga gcgcaatggt ttgcaatggg t cgtgagttg   6480 attgagatgt atcctgtctt taaagaggcc ctgctggaat gcgatggata t atcaaggaa   6540 atggggtcaa cctggtccat tataggtaaa gacccgcaac aagtccccgg c ccaggctat   6600 ggaaagcact cactcatgtc accattgcag aggaactcag tcgccctgaa a cggaaagtc   6660 gcgttgatca ggcagaattc agtctgccat tgtctacggc tcttcaaatt g cgcttgttc   6720 gtctgctctg gtcgtggaac atccaaccag tagccgtcac tagtcactcc a gcggagagg   6780 cagctgcagc gtacgctatc ggggcactaa cagcccgctc ggccattgga a taagctata   6840 tacgcggtgc attgacagca agagaccgcc tggcgtcggt acataagggg g gcatgttgg   6900 ctgtcggatt gagccgcagt gaagtgggta tatacatcag acaggttcca t tacagagtg   6960 aagaatgctt ggtggtgggg tgtgtcaaca gcccgtcgag tgtgacggtc t cgggagatt   7020 tgtccgccat tgccaagttg gaggaactgc tccatgctga tcgtatattt g cgagacggc   7080 tgaaagtcac ccaagccttt cactccagcc acatgaactc gatgacagat g ctttccgag   7140 ccggtcttac agaactcttc ggagcagacc ccagtgatgc agcaaacgcc a gtaaagatg   7200 tgatctacgc ttctcccaga accggggccc gcctgcacga catgaatcgt c ttcgggatc   7260 ctatacactg gtcgaatgc atgcttcacc cggttgagtt cgaatcagca t tccgtcgaa   7320 tgtgcctgga cgaaaacgac cacatgccaa aggtcgatag ggtcattgag a ttggacctc   7380 acggagcgct tggaggcccg atcaagcaga tcatgcagct tccagagctt g ccacgtgtg   7440 acatccctta tctgtcctgt ctttctcgtg ggaagagctc tctgagcacc c ttcgccttc   7500
```

-continued

```
tcgcatcaga acttatccgg gccggatttc ctgttgactt gaatgcgatc a actttcccc   7560 gcggatgtga agcagctcgg gtccaagtgt tgtctgatct accgccctac c cttggaacc   7620 acgagaccag atactggaaa gagccgcgca tcagccaatc tgcccggcag c ggaagggcc   7680 cagtccacga tctgatcgga ttgcaggagc cgttgaacct gccgttggcg c ggtcatggc   7740 acaatgtgct tcgtgtgtca gatttgccat ggctacgcga ccacgtcgtc g gctcgcata   7800 ttgtttccc tggggctggg ttcgtgtgta tggcagtgat gggaatcagc a cgctctgct    7860 cgtccgacca tgaatctgac gacatcagtt acatcctacg cgacgtgaac t ttgcgcagg   7920 ccctgattct acctgcggac ggggaagaag gaatagatct gcgcctcacg a tttgtgctc   7980 ccgatcagag tctgggttca caggactggc aaagattctt agttcattcg a tcactgctg   8040 acaagaatga ctggacggaa cactgtacgg gacttgttcg agcagagatg g accagcctc   8100 cctccagttt gtcgaaccaa caacggatag acccacggcc atggagccgt a aaacggcgc   8160 cgcaggagct gtgggactca ctacatcggg tgggaattcg tcatgggccc t tttttcgaa   8220 acattacgtg catcgaaagc gacgggcgag ggtcatggtg tacatttgcc a tcgcggaca   8280 cggcctccgc aatgccacac gcctacgaat cccagcacat tgttcaccca a ccacactag   8340 actctgcagt tcaggcagcc tataccactc ttccattcgc tgggagccgg a tcaaatctg   8400 cgatggtccc cgctcgcgtc ggctgcatga agatttcctc ccgacttgca g atttggagg   8460 ccagggacat gctgcgcgca caagcgaaga tgcacagcca aagtccttcc g cattggtaa   8520 ccgatgtagc agttttgat gaggcagatc cggttggagg gcctgttatg g agctcgaag   8580 ggctggtctt tcagtctctg ggggcaagtc tgggcacttc tgaccgggac t ccaccgacc   8640 ccgggaatac ttgcagctcc tggcattggg ctccagacat cagcttagtt a accccggct   8700 ggcttgaaaa accctgggc acaggtattc aggagcacga gatcagcctc a tattggagc    8760 ttcgacggtg ttcggtgcac ttcattcaag aggccatgga aagtttgagc g taggcgatg   8820 tcgagaggct gagtggtcat ctggccaaat tctatgcgtg gatgcagaaa c aactggcgt   8880 gtgcccaaaa tggcgagctg gggccagaga gctccagctg gactcgggat a gcgagcagg   8940 caagatgcag cctccgctct agagtggttg ctggtagcac caacggcgaa a tgatctgtc   9000 gcctgggctc cgtgctcccc gctatcctac gtcgggaagt tgatccgttg g aggtgatga   9060 tggatggcca cctgttgtcc cgctactatg tcgatgccct caagtggagt c ggtccaacg   9120 cgcaagccag cgagctcgtg cgcctctgct gccacaaaaa cccgcgcgct c gcatactgg   9180 aaatcggcgg aggcaccggg ggttgcaccc agctggtcgt ggactccttg g cccaaatc    9240 cgccggtagg ccgctatgac tttactgacg tctcggccgg gttttttgaa g cagcccgca   9300 agcggttcgc gggatggcag aatgtgatgg attttcggaa gttggacatc g aggacgatc   9360 cagaagcgca ggggttttgtg tgcggatcct acgacgtggt gttggcttgt c aggtcctgc   9420 atgccacttc taacatgcag cgcacattga ctaatgtgcg caagctgttg a agccaggag   9480 gcaaactcat tcttgtcgaa accaccagag acgagcttga cttgttttc a ctttcgggc    9540 ttctgcccgg ctggtggctc agcgaagaac cagaaagaca gtcgactccg t cactaagcc   9600 ctacgatgtg cgcagcatg ctgcacacta ctggattcaa tggtgtggaa g ttgaggctc    9660 gtgactgcga tagccacgag ttctatatga ttagcaccat gatgtccacg g ccgtacagg   9720 cgactccgat gtcatgctcg gtcaaattgc ctgaagtgct cttggtctat g ttgactcat   9780 ctacgcccat gtcttggata tcagatttgc agggagagat tcgcggcagg a attgttccg   9840 tcacttcgct acaggcactt cgtcaagttc ctcctaccga gggccaaata t gcgtattcc   9900
```

```
ttggagaggt ggaacactcc atgcttggtt cagtcaccaa cgacgacttc a cacttttga    9960
cctcaatgct acagctggct gggggaactt tatgggtcac ccaaggagcg a caatgaagt   10020
ctgatgatcc cctgaaggct ctacacctcg gattactacg taccatgcgt a atgaaagcc   10080
atggcaagcg atttgtctca cttgacctcg acccttcgcg taatccatgg a caggcgatt   10140
cgcgcgatgc cattgtcagt gttctggatt taattagcat gtcagatgaa a aggagtttg   10200
actatgcaga gcgggatgga gttatccatg ttcctcgggc atttagtgac t ccatcaatg   10260
gaggcgagga agacgggtat gccttggagc cattccagga cagccagcat c tcctgcgac   10320
tagatataca gactcctggg ctcctcgatt ccctgcactt cacaaagcgc a atgtggaca   10380
catatgaacc agataaatta ccggacgact gggtagagat tgaaccgagg g cgtttggtc   10440
ttaacttccg tgacatcatg gtcgcgatgg gtcaattgga atcaaacgtc a tgggcttcg   10500
aatgcgccgg cgtggttaca agtctcagcg agacagcaag aacaattgca c ccgggcttg   10560
cggtcggaga tcgggtttgc gccctcatga acggacactg ggcgtcgagg g tgaccacaa   10620
gccggaccaa cgtggtgcgc attccagaga ctcttagttt cccgcatgct g cctccatcc   10680
ctctggcctt cacaacagct tacatttcac tttacaccgt tgcccgcatt c tgccaggtg   10740
aaacggtgtt gatccatgcc ggggcaggag gcgtaggcca ggcggccatt a ttcttgctc   10800
aattaaccgg tgctgaagtc tttacaactg ctggcagtga gaccaagcgt a accttttga   10860
tcgataaatt ccacctcgac cctgatcatg tcttctcgag cagggactcc a gcttcgtcg   10920
acggtatcaa gacccgcacc cgtggcaagg gggtggacgt ggttttgaac t cgctagctg   10980
ggcctctcct tcagaagagc tttgactgtc tggctaggtt tggtcggttt g tagaaatcg   11040
gcaagaagga tcttgagcag aatagccgac tcgacatgtc gacgttcgtc c gcaatgtct   11100
ccttctcctc cgttgatatt ctctactggc agcaagcgaa gcccgctgaa a tcttccagg   11160
cgatgtccga ggtcatcttg ctgtgggagc gaacggcaat cggcctgatt c atccaatat   11220
cagagtatcc tatgtcggcc ctggagaagg cctttcgcac tatgcagagc g ccagcacg    11280
ttgggaagat tgttgtgaca gtagcccccg atgacgcggt cctcgttcgt c aggaacgaa   11340
tgccactatt tctgaagcct aacgtgtcgt atcttgttgc tgggggcctg g gtggtatcg   11400
gacggcggat ctgcgagtgg ctggtcgatc gcggggcgcg atatctcatc a ttctgtctc   11460
gaactgctcg cgtggacccg gtcgtgacga gtctccaaga gcggggctgc a ccgtttctg   11520
tacaggcgtg tgatgtggcc gatgaaagcc agcttgaagc ggctctccaa c agtgtcggg   11580
cggaggaaat gcctccgatt cggggcgtca tccaaggggc aatggttctc a aggacgccc   11640
tcgtctcgca aatgacggcg gacgggttcc atgccgccct gcggcccaag g ttcagggaa   11700
gttggaatct gcaccgaatt gcatcggacg tggatttctt cgtgatgctc t catccttgg   11760
tgggtgtcat gggaggcgca ggacaagcca actacgcggc tgccggagcg t ttcaggacg   11820
cgctcgcaga gcaccgcatg gctcacaacc agccagcggt caccatcgac c tcggaatgg   11880
tccagtcaat tgggtatgta gcagagacag attctgctgt ggcggaacga c tccaacgga   11940
tcggctatca accccttgcac gaagaggagg ttctggacgt cctcgagcaa g ctatatctc   12000
ctgtgtgttc cctgccgca cccacacggc ctgctgtcat cgtcaccggc a tcaacaccc   12060
gcccaggccc tcactgggca cacgccgact ggatgcaaga ggctcgcttt g cggggatca   12120
agtatcgtga tccgttgagg gacaatcatg gagctttgtc gctgacccg g cggaagatg    12180
acaatcttca cgccaggctg aaccgtgcaa tcagccaaca ggagtcaatc g ccgtgatca   12240
```

-continued

```
tggaggcgat gagctgcaag ctcatctcaa tgttcggcct gacggatagc g aaatgtccg    12300 ccactcagac attggcgggg atcggcgtgg actccctggt cgccattgag c tccggaact    12360 ggatcacagc taagttcaat gttgatatct cagttttcga gttgatggag g gccgaacga    12420 tcgccaaagt cgcggaagtg gtgctgcaga gatacaaagc ttagatatat a tgtatatgc    12480 atatctctcc ctatagctac atatatattg acatgcctcg atagtgtctg a ttttctctc    12540 ttacagcatc ccgttctgag atgcagattt gtttcttgcc tagcgtgaat a cgtcacttg    12600 ttgtgtgaca atgaataaat cagagccata gccatgcaag cgtaatccta t agagtcctt    12660 ggatgagacg aaggccatgt atcagcgcag cacatcttgc tgtctctttt a ttcattaat    12720 gctcgtccgt agaccggaaa atggttttat tatcttaggt ttccctatca a taagatcct    12780 tagctgggtc cgcagggtta agaggccact gccacaatcc aggttaatag t ctcaacatc    12840 gtggtgctgc aacgtctgat tgaggatctg tgtaacatct acggatggta a ggaaaattg    12900 gttgaagaat gttgcatagc cctttgagat gtatgtagag ttgtttgggg c aggttcggg    12960 tttacgctct aggatctgct gcagattacg ggttgaaacc ccccagacgt g ctgggttta    13020 gttagtgtag gttaattagg ataggtctat gaagctactt actacttact a aggtttgta    13080 gtcttgaggg tagctgggaa tccatgtcgt cgggccatac tttgggaaac a ctttagaga    13140 cacggtgcaa cccaccatat cgcccgcacc cgccacgctg cagccagagg g aatagaaag    13200 aaaacagaag agaaacgcag ataaagaaca acggcgttgg attcctgcaa c aagccttgt    13260 cccacgctac ctgcagcgcc tcccaatttt cacatgggtc cggcggaacg a acgtgagac    13320 aagatgctac cgccgagtgc gcagccggaa gggatttggg acacggaggc g tgtctaacc    13380 ctatattggt taggtgtctt aagtgatgtt tatcgtcggt tcgcacagag t tacacgaat    13440 atcccctttt cctgatatga tgtatattta tatgtaaggt gccatctcca c atacatcca    13500 tccatccatg gatacacccg tcttcactct gtaccttatg gcttcagcag a caagaatcc    13560 ggaggagaca tcgcttaaga attcctgcgt cgccatacct cccgtcaata t caccaccgc    13620 caccccaact gccctctccg cctacgcccc ctcgcgccaa cctcggagc c caccctcat    13680 cgaagaagag aaactcctga cccacaaaca caccttcgaa atcttatcaa g atgggtcta    13740 ccgccacatc gtcacctcgc caccgctcat cacatcccca catctggccg a tgtcgccgt    13800 acgagctctc caacgcgccg agccgggttt ttctctccac gacaagggag a tactacata    13860 tacttctgac tcggaggatt cgactccata taccgacacc gacacagacg a ggagttact    13920 ctactcgtat gcggcaattt gtccggcgtt ttcggcggga gatgcagagt a tcaacgtca    13980 ccaccggatg ggcgtatatc ccatgaattg ggtacgtatt accgacatat a tccttgcaa    14040 cgcaactcta ctgctaataa gttagcagtg ctattttcga ttgattgtgg g ttgcaaagc    14100 tagacacata ccagaacccc aaggcactct ctaaacgggc ctatctagta g tctctcata    14160 tcgaattatg tcctcctcca taataagacc aaattcgctt tggctagtca t gtcaatgcc    14220 aagtggaaag tcgagaagt tgtcaatgcc aagtgaaaag tcgggaaac c aaggcattg    14280 gccagcatca ttgctcagca aatcctgggt tgcatcctca gaaggagtcg c aattgtacc    14340 atccattggt atttctctcg ggttgaagta tatgtcccag acctggccgt c tccgggtac    14400 accaagcggg ctgatattca agttatatga agagccggtg ctagttgtgc t agtggacgc    14460 attggcgaca tcgtaatcca tgtaggttgg ctcgttccat gagggcgttg g acttcgtga    14520 tatcgttgtc ggaataaaac gcctctccct taaattctgg aggaggaggg c aatatcgct    14580 acagcgactg gccacttggc ttaatttgta cgagatagat gcagatgacc t attggatgc    14640
```

```
cgaacggttc gtgtatatgg cgaagaaagt gagtatctcc atgtcctgtg a atggatcgg    14700 ctggtcttcc tccacaatgt ggacatagat tcccatgaat gagatcaaag a atagttcag    14760 gacaatgcta tgaagtacat ccccaggtta ggatgctgtc aagagggtcg c acggaagac    14820 ttacctgtcg aaattgctga accagattt acacccatcg cacaattgct t gaacagcat     14880 cagacaatcc cgagcgtgtt gtaggcagac agcgccccctt tcctggctcc a aatgcgttt   14940 atgcagaagt acccaacagc tcgagagtgc aaacctcaac tgcgttgcac a gatatactc    15000 ttcgagaggc ctattcggat ctccggtacg cagtacatgc tcatgttgca c gtgccactg    15060 gctaagtttt cgagcaattc tgcggatacg gcggcggacg cgactctgtt c cattttgct    15120 ggattttgct gagtataagc ccagatatat ctcctcaaga atgaatgcca a gcgtatgcg    15180 tgccgcaaaa gcatttggta gtggcgcagc ggagtcatat ggaggcaatg g tacgctgca    15240 gtcatacgag gcaataggc aggccttgcc cccaatgatg gatacgtgct t ctaaatcct     15300 atagtaagcg aaatgctcag aaaacgaagc aagtttttga cgaacatcga c gaggaagat    15360 gctccagaac aagtctttag gctggtcgcc cacagcccca tcttccgttg g cggggtcgt    15420 tgtcgttaaa tggagtccaa tgagcctgga caactcgcag acttgagcaa a gatagtcag    15480 aaaaattgcg aaatcaaaat actccattgc cacaagtgcc ttagtataat a aagtcaggc    15540 cacgttccaa aggtagggtt gtaagacgca ccaaacaaaa gagggcccgt a tattcgata    15600 gccgggtttt aacaagagtt tccaatcgat tatagcactg cctgatatta c gcagcaggc    15660 ttatgatcat ataatctatt ggtatgtctt gtcctgtgca tcccacgact t tgttcgcaa    15720 ttgatgtttg agtcagggcc tgaagcacaa tgcagttgaa agaggtaatc c aaaccaggt    15780 ccggaggccc agttctgatt gtgtactgag attccactgc gtccataata g tctgtcgac    15840 taaatatagg gagtcgtgga tgcagcttct tgaaatattc gttgatagac g gctccacta    15900 gagcgcgggg tggaagagac gggagaaagg tatcgttttc ggatgccgat a gtgttggga    15960 tatcctcaat gatctgttga agcgtttcat tcgcctcagc caccttcgag c gcacagctg    16020 acacagcttg gcggtcaaat gcgaccatct ctgcgacttg gccgctggtc a tatcgaccg    16080 gtaaccaaga ggttaggttg gcgttagcag cctgtgcctc catgacgagt g aaacaaaag    16140 agccataacc gtggagaggc cagaatccat cttcctcggt gggtgaagtg t gtttgcctg    16200 agtacaagtt tacttcacac tcttctgagc tggttgagct tgtgtacccg c tttcttgtg    16260 actgtggcct tgatagatca cgaaagccct gatgggcatc aataaaggac a ggcatcgtt    16320 ggagggcatg ttcgatatct ccaacccgac tcccgagctt ctcgacgtcg c gcgccctga    16380 ctgagagtca gaaagacagg tatttgaccc aaatatagac catcttatca c ttacaattt    16440 tgctgtttgg ttgacccgtg taactttgtt ggagaattca cagggtaggt t atatcggag    16500 gcaatgggag cactttggac cctccttgct gcatcggacc ttacgdatcc g gcactcatc    16560 acatgcagga aatgcctgcc gcttcgacga cagctctgca ctctccatca t tcaactcta    16620 tgtgagatag aacatgagtg aacgatgagg gaaggccctg gtactcagat a agtccttga    16680 tgtctctgta gatctcaact gtgcaagacg aagactggtt tgaagtaagg c ccacagctg    16740 aagtggcatg ataagttcac ctgttggttt aatataccct attgttgatg a aagcctgac    16800 cttggccaaa gaagggagca gctgagtatc cgacatattt gataaggacc a gcggcaagc    16860 ttgggatctg ctgcatactc ggattacgcg aaaaggtagt cggagtacgt g aaaaggtac    16920 tcggagtacg cgaaaaggtt agattaagcg ctacggacgc cggcagtccc t gaatgaaac    16980
```

-continued

```
tctgcgggc  ccacttgccg  ctgacggtgg  cacgatgaac  cttctggccc  c tactctaat    17040 atagcacaag  gtgctcgaat  aacaaagctt  gtcgccatcg  tggcgttgac  g ccagcatgg   17100 ctctgcattt  gctgtactat  acggtaagct  tagtagggcc  aaatttatac  t atagtatgt   17160 tatttccgat  ttacgtacgg  aatgggaaag  aacttgtatg  cggccgcagg  c tgaaaaggg   17220 ccgaattaaa  gaactgccat  aactatgtgc  atcccgatga  tgcctcaagc  g cagcattca   17280 acagggcaa  aatatcgtca  caggtcagat  ttattactac  atcgggaagt  c ttcggagat    17340 tgattccgag  gcatagagtg  ccttggacta  gcgacgccaa  gtttctacta  t caggaaaag   17400 tgctagttcc  agattggaac  tagccaataa  gtagccagcg  gtaagctgaa  c aactaattt   17460 ttaaatatta  gatgaacaaa  tgcgtagttc  agagacacca  tgcacgttgt  c caatactat   17520 gaggctttag  caagacaaag  tggagcacac  gccacctggt  aaaagtgaac  a ccgtctgct   17580 gcaaaagctc  gtggagtttt  attttgatta  ctagaaagca  gacatcccct  c cttgtcccg   17640 gaatattgca  aatcagggaa  cattgaataa  gctgggccgc  taatgcgtgc  t aagaacagg   17700 gagtccacca  gagtgaggta  gatcccttcg  tatttcagct  gtggcaggac  a gcgatctgc   17760 ggagctccga  cggctagccg  tatggcattg  acagtgaagg  agatcggaac  c tctactcca   17820 gagtacattc  cgaaaagcca  taattattcg  gatgtacgga  atacggaggg  a tgataagcg   17880 ctagaaatag  ggtggatcct  actaaaattc  ggatccttta  gcttgtgcta  a cgtgtcaag   17940 ctggggcatc  ctgtagtccg  tgctactcct  ataggtttac  cggctatata  a atctggtgg   18000 agccagcggc  ccctgcacct  ctttaggaca  cgcggcccct  tcaaaaagt  c aaaatagca   18060 gtcaagagca  gtgaaagaga  cccatgctgt  ctcatagaaa  agcaaggaac  c tcgaaatcc   18120 acatgagatc  gatccacatg  gttctacttc  aagtgggtca  ttaattcccg  t cacctgaga   18180 catgagatac  ttagtagcta  agatatggta  catgctgttg  atcaaacgat  a tgagtgtca   18240 tgttggggtg  aatactaagg  aacatttcta  ccaacaatct  cgcggtgaat  a gaaaactga   18300 cctttaaatt  ccagcacggc  gaacgaacag  catccatatt  tcagtttggc  t cgtcaaga   18360 acttgtagac  tttctcgtac  cttgacgctc  tgtcagtgta  caagaatatc  a tgcctgtag   18420 attactccta  aacttacacg  ggaaacatga  tggccgaggt  aagggaaagt  c tccctgtcc   18480 gaaccagac  gccggaccag  aaaacccaa  tgccttcatt  gcgcagaagt  g ttttcacgc    18540 agttaaaggt  atttccgtac  agttgtcttg  cctgaagaga  ttgcattctg  g taacccgaa   18600 gtcgcatcca  agtcagcata  tacttatctg  ggcgggttac  tgtcgatctg  a gcagcactt   18660 accgcgtctt  gatcacgtcc  agtggctgtg  tcgaccaggc  gcaacaaact  c cagtaacag   18720 aaccgaccaa  ggtgcttgcc  agagggtgca  cgtcttcgcc  gttcttcgag  t attttcggg   18780 ccagcccaat  aagttcgtta  taaacagtga  acttcactgc  cgcattggac  g actgccgca   18840 aaattgtagg  accaaccgca  gagaagaatc  caagcggtcc  ccgatctcga  a ggattccag   18900 ctatcgcgcc  gaaagtcgta  cttaactctg  catttccaac  cttccttgca  t caatgctaa   18960 gagaacgaat  taagaactga  tcggataacg  ggtgagatgt  tgcaacttac  a ttttcgtct   19020 tgatcgcctc  cgctggggtt  acggctaaga  cagcctcggt  cacgccagcc  c caaacccag   19080 ccaggacgga  agctccagtt  gagagctctc  catttgggcc  cgagagggcc  g agcgataaa   19140 tattgaagga  ggcaaattct  gtttgttatt  gcaaacggtc  attcctttc  g ctccacgcg    19200 ggcttataag  ggggatcgct  acatacgaac  ggaggctttc  aatgtggttc  c taccaaggt   19260 ggctccatac  ccagcatacc  agcctcggat  tccaggtttt  atagctgcca  c atcatggtt   19320 tctccgctta  agctgggcgc  gagttttagc  cgctaccagc  ggaagcaata  g actgtcagt   19380
```

```
tggcggccac ggtaaagcgg aactcttaaa cacaggataa gctcacattc g aaagggtag   19440 gtgatggaga tttcaactgc cccagcacaa gcacccgcga ccaatgcagg a atgcctttc   19500 gtctatacat atattaagag aagacattgt cagtaacatg gcacacgcgc g accaagaag   19560 gaacacatac acgcttccca cgggcttttt gggtaagggg tgcctttggt a atggaacat   19620 ttgtctggac tttagactcc atgacgagga tgtgctgagt ccaaacaaag c ttttcttca   19680 cagagatagg gctgcagacg ttatttccag tttaccttcc ctgtgttcag t atcaggtct   19740 tatattgtat tatctcaatg cttatgactc taagtggaat acattggata t cagtttgtc   19800 acggagtcgg cacccgatgg ctatcgcaat cgtccctggt gggtcttgaa a tcgtatgtc   19860 acacttattc cggatgaaac acattccgga gcgcgcgttg atattgctaa a cagtataga   19920 cccaaatggt ctgcagaagg ccctaaatag taggtctcat tagccagtat t tagttgtga   19980 ttgcagatca ttgtcagcct aacatcagtg taggttacgg tgtgatattt a cttgcatag   20040 aaggttccag accacacggt tctagatcct ttgacagcag catgaatgga t tcccctcta   20100 ggtgccgggc gccgacgtgt gcgttgctcc gaaatttgta ggacggagct c ggataccta   20160 gccgctatgg gcatcggagg ttgtagcagc gtacacgctt ggatagttaa a taatcggat   20220 gtacacccac tgttggaaat gacggggggcc taaaacacga gattatctga t ccaatttct   20280 gttcgttggc attctatcat tcgcagcgaa gatcgtcctc ttaaattgac c atgaccaag   20340 caatctgcgg acagcaacgc aaagtcagga gttacgcccg aaatatgcca t tgggcatcc   20400 aacctggcca ctgacgacat ccctccggac gtattagaaa gagcaaaata c cttattctc   20460 gatggtattg catgtgcctg ggttggtgca agagtgcctt ggtcagagaa g tatgtgcag   20520 gcaacaatga gctttgagcc gccaggggcc tgcagggtga ttggatatgg a caagttagt   20580 tctatccaat ctgaacagtc tacaaagtat actgacgatc ctttgtatag a aactgggc   20640 ctgttgcagc agccatgacc aattctgctt tcatacaggc tacggagctt g acgactacc   20700 acagcgaagc ccccctacac tctgcaagca ttgtcctccc tgcggtcttt g cagcaagtg   20760 aggtcttagc cgagcagggc aaaacaattt ctggtatagc tgtcattcta g ccgccattg   20820 tgggggttttga atctggcccg cggatcggca aagcaatcta cggatcggac c tcttgaaca   20880 acggctggca ttgtggagcc gtgtatggtg ctccagccgg tgcgctggcc a caggaaagc   20940 tccttggtct gactccagac tccatggaag atgctctcgg aatcgcgtgc a cgcaagcct   21000 gtggcttaat gtcggcgcaa tacggaggca tggtcaagcg cgtgcaacat g gattcgcag   21060 cgcgtaatgg tcttcttggg ggactgttgg cccatggtgg gtacgaggcc a tgaagggtg   21120 tcctggagag atcttacggc ggtttcctca aaatgttcac caagggcaat g gcagagagc   21180 ctccctacaa agaggaggaa gtggtggccg gtctcggttc attctggcat a cctttacta   21240 ttcgcatcaa gctctatgcc tgctgcggac ttgtccatgg tccagtcgaa g ctatcgaaa   21300 accttcagag gaggtacccc gagctcttga atagagccaa cctcagcaac a ttcgccacg   21360 ttcatgtaca gctttcaaca gcctcgaaca gtcactgtgg atggatacca g aggagagac   21420 ccatcagttc aatcgcaggg cagatgagtg tcgcatacat cctcgccgtc c agttggtcg   21480 accagcaatg tcttctggcc cagttttccg agtttgatga caacttggag a ggccagaag   21540 tgtgggatct ggccaggaag gttactccat ctcatagcga agagtttgat c aagacggca   21600 actgtctcag tgcgggtcgc gtgaggattg agttcaacga tggctcttct g ttacggaaa   21660 ctgtcgagaa gcctcttgga gtcaaagagc ccatgccaaa cgaacggatt c ttcacaaat   21720
```

-continued

```
accgaaccct tgctggtagc gtgacggacg aaacccgggt gaaagagatt g aggatcttg    21780 tcctcagcct ggacaggctc accgacatta gcccattgct ggagctgctt a attgtcccg    21840 taaaatcgcc actggtataa atgggagcga tttcatgcca cgggcacaaa t cctagggca    21900 tatcgtacct gtatgatgga agcaccagcg gtttagcaga tagatgatag g ttccttctg    21960 ctctgcgttg cgttttgaat ttagttactt cgctggctta agaatttaga a tgaaatgca    22020 gtctctctta ttccttatta aactcacgta ctcccacatt cggcgactgg a ggatacgaa    22080 agcagtgttg gtgatgtttc ctgtaatgga tatcattttg ctgactgaat t attctatga    22140 cctttccctc caacggcgtt cttatctcga cactttagat gttgacgctg c cttgaggaa    22200 ctagctttgc gctgcgaagg ctatgagcag tggagctgca tcctttcgcc t agatatcca    22260 ttctgcatag atccaaggca gggcttcgta agaaaagttc acgttcactg t aagtccatg    22320 caagcggaac ggccgcttaa acaagtctat acagtaaagc ctgcctataa g caaccgccc    22380 atataaggaa tcccgcgata ttagcatcta aaatccgcgt ctgaattgat t ttctatata    22440 aataagcagt aaactgcttg aaaaagccct gctctcctat acaaagctac c ttaattaga    22500 aaatataggt tgactagcta aaaatgtgcc ttacaatatc gtattattat a taatactta    22560 tatgaccacc ggaggtaggc tagaaatata tatcgtaaag agattacccc t tagtaaaaa    22620 tatatatttg tatagacctg gctgtaagca atttcttatt ataagtaact t tttggtgag    22680 ctgaattcgt tgcttatagc caggtttgct gtaattgata aaaggtgcca a ttcatcata    22740 atctatcccg catcggatga attgttgacg atccacacca taaactgcat t atgttctac    22800 attttcctca ttggtatcta ttgggtaggc aggttgaaag ccctttctgc c caccttttgc    22860 atatttatcc cccaccgtgc gatggccgcc gtgatcaatc cagctatagt c gaagcaacc    22920 acacctgcaa caactgtgag catgtacatt gagaggtaag aagaaaggta c catacatag    22980 cgtgaacgtc catccaactc cgagggcgtc tatgacgggc acaacgagcg c actactccc    23040 tgcagaaaag gagtattgaa tcatatactt tcctgcaatg actgcagacc g gttccgtgg    23100 caaggcttct acttgcggtc agagacaaca ttattgtggg catgtacaca a aggggataa    23160 attaatgagg gtgtggaaca aaccagccac gtaagtgttc aggcagttaa a actgcccat    23220 gagcccccag cccgcgaaga acgccgcgat tatgggcact accatcccac c cttatcctc    23280 ttggagtgtc cacccgtaaa tgagcgttcc cgcaggcagc acggcaaaca a tgtgatgag    23340 cccgctgtgg agtcgatcct gagggagacg gaatccgcgc tttactatgt a tctccgaac    23400 ggtgcgatcc gaaagtttac cgccgacgag actccctatc aggaacccgg c acctggagc    23460 gaggtagaag agacccgata ctagggcagt cgttaaatga aaccgtgagt t gaatatagc    23520 acgagctgaa gtcaggatcg aatattgcgt aatcgccagg aggccacagc a taagtcctt    23580 ttgtttgcgg catgagcatt tcgtttccag tagatgcaga gggcatatct c ccaggcact    23640 tacggcaaga aagacatttg gatacaccca ctgcttgagc acatccgttg g ggagaattt    23700 cgatatgatt gaaacaagtg tggtcggttt aaacgccgtt gagaccttct c agaagttcc    23760 ttcgattttc gggaaaaata gcagggaaag cacgagcccc agtccgctca t acctagttg    23820 aagccagaag ataacacgcc aactcgtgaa agtgacgatg acccctccca c gcaggggcc    23880 tgatcaaaca gtcagttcct gttgggagtt ctagtacttt cagcagggta c gtacctatt    23940 gcagggccag aaagagtccc ggccatgaag aaacctacgg ccgtcccacg g taaacctgc    24000 gcacgaacgg attagttttc gcaattgggg agacaagggc gtgtgatgcg t acaggctca    24060 aagatatctg caagaacagt ttggcctgag accatgaacg aggttccggt t aagccgctc    24120
```

```
aatactctga acgctatgaa cattttctcg tttatcgccg ctgccgttcc a gcggagcac   24180 gcacaaagca ttgaaatggc cagattgtat gatgtccgcc tgccgactaa c ttgttcatg   24240 ggaccccata tgagggatga atatcccatg gcaaccaaga caccagcatt g gagatattg   24300 atagtctcga cagtcatatc aaattcattc gcgatttcag gggcggcagg a agaagacaa   24360 gtactggaga aagtaacgac tagagtcatc caactaacaa caaacgtaat g acacatttt   24420 ctccataatg gaatatcacg gcccttttc tctggctcgt tttgtccgct a ccttccgag    24480 gtcgtcgctg ggttcgggga ctcagtgtca ccgcggccca tttctgcaat g gatggcctt   24540 ctcgtcactg agcggactct tcaaaagaaa atatagaaca tggtcaccca a aacatggat   24600 gttcctgatt gacggtttat gtatactcta tcatcggcct gccacacatt t cgccgagac   24660 tacgttgata gtgtattgga gcgccgctag accttcggcc ttgctggccg a gacgggtac   24720 ctaataaggt agattgtgtc tttccgcaaa ggtattcatg tggatcagtc t agaatggct   24780 gcaaggccca ctgacttgac taatgcaagc caacgccagg atagttatat a aaatccaat   24840 gagggatcaa catcgggatc gacatcggga ccagcacccg gcatccacaa g gaccggatc   24900 cgaaaagtac ggccggccga aaggaaaccc atggaaggtg catagacctt c actgtacaa   24960 tacagtactc tgtggacaat gatattggcc accatctcac ccgtccgata a tccatgtca   25020 ttgatgactg tatttcaaaa tagattggat atctgagaag tgatgaagtc t atagtatgc   25080 tctcttctgt atgagggatt ttgttggttc aacagggttt atcattagtt t gtcactatc   25140 tggccttcgc cgtacaggaa tgcaccgcat gtgtttgtac tctctgtgac t ccctcgaga   25200 ctaaggacat acgtacgta tattggctaa ccaccattat taagaagcg g tggccgagt     25260 gagtacctta ataaggcttg tatgccctct tagtagttgt cggataattt c tccaataat   25320 agggtggata caggggtaac ggcggaacgg aaagaactcc gccgtcggcc t gcggcgcgc   25380 ggcccacctg cacaaccagg ctgaattctc ttgaattctc tttttgatac c ggaaggcgt    25440 gagaaggagg ggaaattcat catcttaagt gctcatctta tatctgcttg a cgaatgcag   25500 attgcccagt gcgctcaccg gagcccgagc aaaggggcta gagcgggtct g ggttacata   25560 acgacagtgc gacaccctct tcatgtaaag atctcgcctt attcactttc c acattttga   25620 acatccgcaa ctgtgccgta cccagtctcg tgaagccggt aaaatggcta a attcgcagt   25680 aaaatgcctc gatcacttgg tcctgactgt gcggtctatt ccaagaacga c tgcatttta   25740 taccaagcat cttggtatgc gacatgagac gttcacctcg ccacttaatc g aactatcca   25800 gaggtattcg cgcggaagtt gtgatctaga ttgtcgcgat tcggcttact g aacagtcaa   25860 actaggcatg cgctcatctt tggttctcag aagatcaacc tccatgagca t actaaggaa   25920 tttgaaccaa aagcacgtaa tgtgcaaccg gggagtgcag atctgtgttt c ttaacagat   25980 acagacgtct gccaagtgct caaggcattt agggacgccc agattgaggt a tgtgtagca   26040 aatgcttcta aaagcgcaag cactgaaggt taggtgcagg tactagaaga t tccaaagtt   26100 gtggatagaa caggggcaca aggcaagatc cggagtgttt atgtgcggga c cctgatgga   26160 aatctagttg agtaagtgtt cttgttattt aacagatttc ccttgcttct a acatgtgtt   26220 aagagtatca aactatgtct catctagcca ggctggcggt caataagctt t acaaggtta   26280 tatgacccgt aactgagttg cgcctgtacc gtgattagag acaacattca t tgttccatg   26340 ttggcctcgt tctgtcatca gttggttaca cactggctta taggcaacat t tcgcgtaga   26400 tttaggtagt tatttgctcc gcagttccgc ttgtaatcaa agaaaaccgg g ttctggaga   26460
```

-continued

```
atctgtttca tttcagggct cggcctggac agtgacggct gaggtctgat gggatatgc    26520 tgggtttagt ctccaccttta aacatagtcc acgtctcaat ggcgtattgg ataatatcga   26580
aggggatctg agttgctagt ccaacttaca cctaaagtag tcttgcaggc catataatat   26640
tcgacataac tataccactc cagtgatgga aatccataac ttatgatact tccgaatgaa   26700
cgtgtgtctt tcgtgtagat aagtccagtt cataaaatcc aatataccctc aataaaagct  26760 tcgtaaatca tccttgcatc agcaccctcc ccccgccccc tttgtttccc acgccttacc   26820
ggcatactca tgtaacctac aactcctttg tccgctcctc actctctgca atccacccttc 26880 tcaaactggt ctcatccctc ggcttaaaac caaccttgaa tggcttcggt tccgttgtca   26940
tcgatgtcgg agtagcgttg cactcaatag catcaagcac tggcatatcg gccgggtttt   27000
gagctggctc tatggtaaac gccacgataa accgaagaaa gaccgtgtat agctcgcggc   27060
tcgcgaggtg ggaggctgcg cacatgcgcg tcccggcgcc gaagctgtag tgagggtgc    27120 cgaagccttc gctcggctcg aggtatcgct ccgggagaaa gcggttgggc atgtcgaaat   27180
gatcttcgtc gtagtttgct gcccacgcat tctgacagat caattagtcc aggaatgacg   27240
ggataggacg ccgggggtta ggggttaggg ggattgattt taccatgaaa aaggtcgttc   27300
cagcagggat cctcgcgcca ttatagatga cctccttgat attcacacgc ggaatgcaga   27360
taggcattac ggtccagaag cgcagggtct ctttcacaag tgcagtgata tagggcactt   27420
tttcctccac tagacaccgc tcccaggcgt cgccattcgg atacacggac ataatttctt   27480
cgtaagcctt ctgctgaatg cgttggccgt cttccgaaga caggtacgcg atgcccatga   27540
tcaagttgcc aggaacggta tcaagtcccg cagaaaccat ggtcagacag atagacttga   27600
tttccgctga gaaaggttag tatatataat cacaaatcat atagtggtgc atcgctcgtg   27660
aaatagacat accatctgta agcttcgtct cgggattctt cagaatattc cccgtaatgc   27720
acggcttatc tgtccccttg gccatgcgat ccttcaaaat atcaaacaaa aggccatgt    27780 acttatctct ccgcgcacgg agatgcttcg cctgattgct tctgttcgag acaacctga    27840 gcagaggaac gtaatcctgc cagttgttgc tggttgaccg gagattggcc acgccgcgct   27900
gcacctcgca gatctctctg agaagctggt cgttcacatt gccctcgatg cggtagccat   27960
agttcagagt taaactggtg ttgagcgcaa accgctggaa gtagggagta ggggttgatat  28020 ctatcttccc gccctgtgaa tctttcagca actccttaat actggccata ctctccagat   28080
cgattatggg catataggac tgcaccgcga cacggttgag cgctgtcgca gccgccttac   28140
ggcgccgttt acatgactca tcccacggtg acgttccgat cgtaaagccc tgtgagctag   28200
agacaacacc atgaaatgtg tgaaatgtag ggcgcgatat catcgaagac tgctccttaa   28260
tccacagctg gcgggtggac tcgaaggtgt tggcgaagat gacgcgccta tgcccagac    28320 gcgcctggaa cacaggcccg aattccttttg accatttgcg agcgactgtg gcgtgtttga   28380
cacccagttg tatcagatta ccgaagatgg gcacgcctgg gatctcgggg attcccttaa   28440
tcttagggat gtcggttcgg ttgaagtagc gggtgaggaa gtagataacc gcggtagcgg   28500
cgatgacgat gatttggaga gtcatagtgg cgagatgcga atggtattga agatagata    28560 gataattctt ttactcaggt tggcatggat tgtggcccgg gctttatact tcaaccctct   28620
atcgacatca ttccttaaag accaggatat tccgtcatag taacggcgat agtgacgcgg   28680
ccgcgttctg tcagcccgcg atcagctctg tcatgtggcc aatattctga tctacattgg   28740
tttcagactg atggtctggc tcgaatcgaa gcttcaaagg gctctcacaa cgctgcgttt   28800
ccgattatcg gtcctatctt ggtgcctacg gacacggcgg ccggcgacga tcgagcggac   28860
```

-continued

```
ggccggcacc cggcgatgga tctgatctgc cgcacatctt aatgataggt a ttaatggac   28920
ggctgatcta accttataag ctataacact tatggagagt cgaatgcaga g ttgaaggag   28980
acgttggaag acaaacactg tagtatggcc gcctctaact agttcactga c aagggtgct   29040
gtaacaggca tagactgtta ggacggatca acccgaccta agctgaccca a taccaagtc   29100
tacggggtac tttctgtaaa gaggctggag accgcgacgt tcaattattc c aatctgttt   29160
ccaccactat cttatatgta taagttgtct tccctcggtt aacttgctct t catgttaca   29220
tcttgtcact aataggcatt tgatgtttga tttggctatt gactattgac a gaacctcct   29280
atgaatttcg cctttcagtt gccgtcggtg gttgctgtcg ggccgactac t tgttgccgc   29340
tggtgattga atgctactta tatatatcca tgtcttttg tcggctttta t cacgccact   29400
gccgccggat ttatccggta gaccctccta tcctgtcccc aaagcggggg a atgcgtcaa   29460
gatcttcggg gatgaaattt ccccgcatcc agctccctac ctatactaca c agttaccaa   29520
caattggcaa taaatagaca aacataacga acaaaaggca gctagaccgg a tattaccgg   29580
gtaaacgggt ttgtaaattg gacatcctgg ctctctccag agctacttaa g gattgtctg   29640
ttggagaagc caaatgagaa agaggtgctt gtattagctt ccgaagcgcg t ttctcgata   29700
cctacctagt caatgcgcct ttcaaattgg ggctacatgc ttcttgaggg t tttatcagg   29760
accaacttcg atctgtccgt tgcaagaacc aagaaacctt tccgccaaca a agcaaaact   29820
tgaccatgaa gcccgcaatc cttatgaaat actggctctt cgtctcagct g tgagcgcgt   29880
caaccctgaa cggcaagctc acattgagtg agacaaaggt gacggggcc g ttcagctgg   29940
cttgtaccaa tagtccaccg gacatctata tcgaccccga tgattcggtc t cagtggttc   30000
gcgcagccca cgatctggcc ctggactttg ggcgcgtctt tggtaaaaat g ccacagttc   30060
gcttcactaa cgagactcat ccaacatcga tggccatcat cgctggtacc a tagataagt   30120
caaccttcct tcagaggttg atagcggatc ataagctcga cgttaccagc a tccgtggcc   30180
agtgggaatc ctattcatca gcactggtgt tgggtccagc caaaggcata c agaatgcgc   30240
tagtcatagc tggcagtgac cgtcgtgggg ccatctatgg cttatacgat a tatctgaac   30300
aaattggcgt ctcgccattg ttctggtgga cggatgttac cccaaccaaa c ttgatgcca   30360
tctacgcgct agatgttcag aaagtccagg gtccaccgtc agtgaagtat c gtggaattt   30420
ttatcaacga cgaagcgccc gccttgcata actggattct tgcaaattat g gcgaggttg   30480
agaacgggga ccctgccttc atctcacgtt tctacgccca tgtcttcgag c tgatcctgc   30540
gcctgaaagg gaattacctc tggccggcga tgtggtcaaa tatgtttat g ttgatgaca   30600
ccaacaatgg cccactagcg gactactacg gagtggtaat gggcactagc c acactggta   30660
tgacggttgg gactccctgc ttgaaagccc atgctgacta cgaaaagaa c cgatggctc   30720
gagcaacaaa cgagcaatcc cagtttctaa acgggacgtg ggactggatt a gcaacgagg   30780
tcaatgttaa agcatttatg agggagggtg taattaggag ccaacactgg g agaccgcat   30840
acacaatggg catgcggggt ctaggcgatg ctgcatcgcc gacacttaac g caacagtgg   30900
aagaaagcat tgttagctgg caggaatccg tgctatcgga catcctgaat a aaaccaacc   30960
tgtcgaacgt ggttcaacca tttgtcctat ttgatgttag gatccattca c cctcaaata   31020
tatcgtttgc tgactgccag gtctgtgaca caggaactgg gaacttacta t gagagcggc   31080
atgactgtac cagaccaggt cacattgata tatcctgatg acaatgcagg c aatatgctg   31140
cgtctcccat tgcagaatga aactgggcgt tctgggggcg caggaattta c tatcatttt   31200
```

-continued

| | |
|---|---|
| gacatgaacg cgccgccgcg ctgttacaag tggatcaaca cagctcaact g atcaggacc | 31260 |
| tgggatcaac tgcgcgcggc atacagccac ggtgctcaga cagtatgggt t gccaatatt | 31320 |
| ggggatat | 31328 |

<210> SEQ ID NO 20
<211> LENGTH: 5053
<212> TYPE: DNA
<213> ORGANISM: Aspergillus terreus

<400> SEQUENCE: 20

| | |
|---|---|
| atggcgtctc tacttttctt tacggtgttc aatctaacac tggctcttct a tcatctact | 60 |
| gccacaggag cagccgtccc tgtctcgcga cccacagacg attcgagata t atagacttt | 120 |
| gacgctgctg aatggcgtcc aagagcaaaa cgagatgatg ccctgaaagt c cctctacgg | 180 |
| atcctccctc ttggcgcatc catcacctgg ggatacctat cctcaaccgg a aatggatat | 240 |
| cgcaaacctc tccgtgacaa acttcgcttt gaaggctggg aggtggacat g gtgggcagt | 300 |
| aagtccaacg gtgacatggt agacaatgta tgcatctctc ttcccccacc c ctccgacag | 360 |
| atagacagac caattgacat ataaacgcgg gaaaaggatg tagaagccca c agcggcgac | 420 |
| gtgataacgc aagtgcaaac cgcggccgca aactcgctcg cctacaagcc g aacgtcgtg | 480 |
| ctgatcaacg ccggcaccaa cgactgcgac tacaacgtca ccctgcgaa c gccggcgag | 540 |
| cgcatgcgct ccctgatcga aaccctaatc ggcgccccgg acatggccaa c acgctcatc | 600 |
| gtcctgtcga ccctgatccc ctcgggttcc acaaccctcg aagctaacag g ccctccgtc | 660 |
| aacgcgcagt tccgcgagct ggtccttgac atgcgcgagg cgcagaatgt c tccatcgtc | 720 |
| ctggccgata tggatccgcc ggctcccagc cccggaaaca actggatcac g taccccgat | 780 |
| aacttcgccg ataacaagca ccccaacgac tacgggtact cccagatggc a gacatctgg | 840 |
| tataacgcga tctacaacgc tgcggtggcg gagctcattg tcaagccggc g gaccttgac | 900 |
| atctcatcca cggggacctg tgacaaagag tacgggagcg gagtctacgc t ggcgggttc | 960 |
| acgcagcaag ggagtggtga ggatgacgga atctatcgac acgacagcga g tatagcggg | 1020 |
| gcgttgttta ctgtccgcgc cgggaagggt gcagccgatc catacaagga t gacgacgag | 1080 |
| ctgcactttt tcttcgggag gctttatact agggcgtatg atgacatgat g atcttccac | 1140 |
| aaagataagg actccggcgc ggtgacgttt gtttcttaca cgaataatgt c cacactgag | 1200 |
| gagcaggagt ttacgaaggg ggggacgttc tcgactcata taattgtaa c ccgggggt | 1260 |
| gtgcattta tcgacatcaa cggtaagcac tgtgtctgtc tgccgaggaa c catctggga | 1320 |
| ctgatttatg tgtgataaat gataggcgac ggacttgatg actacatctg c atcgccttg | 1380 |
| gacgggacca cctacgcaag catcaacaat ggagacggcg acgccaagag c aacaagcct | 1440 |
| ccatccttca ccgatatcgg actatggaag agtcccgaag gatacgatca g gcacatgta | 1500 |
| cgccttgctg atatcgacgg cgacggccgc gccgactact gcggtttggc t gacaacggc | 1560 |
| gacgtcacat gctggcgaaa tggatggatc gaagatatcc ccgcatactg g cagccgctg | 1620 |
| ggcaagcgct tcacggggaa agtcatggga gacctgcgcg gcgtgcgatt c gaggatatc | 1680 |
| aacggcgacg ggcgcgacga ctggatgtgg gttgatgacg atggcgctac g acaacatac | 1740 |
| accaactccc ggagctgcat caaggagag tctggtgacg ggttgaacgt c gtgtggcgc | 1800 |
| caggggttct accaagatgc taactctggc ccgtcgcatc ccggaatggg a gtaatattc | 1860 |
| gggacatccg gattacggga tcaggtctac tttgcgcgac tctatggcga g gtggcggat | 1920 |
| tttggagagc tcgggagaca ggactatgtg ttcatcaaga aggataccta t gacaagtat | 1980 |

```
tttgggccgc tgtattacgt tcatgtgtgg aagagcaagg gcgcaggagg g gctaagatc    2040 aaaggtatgg aaggaagttc tcatagagag gttgattgct aattgttata g ccgacggag    2100 acaggtattg caatatgatg ggccacgaca atggtatgat ggactacatt t ggatccatt    2160 caaccggcca tatgcgtctt tatccgaata ggggcctggt tgaagtcccc g ccgacgggt    2220 cgagcttctg gggggcgaat gagattatct tcgaccccca agagcagatt g gcatgaagc    2280 ttgaccggcg cgatctgcat ctcgcagact gggacggcga cggagcctgc g atataatct    2340 ggacggatcc cgacaatctg aacagggccc aagtttggcg gaacaagatc a aagacacgg    2400 ggagttttga ctgggactac aatatcaatg ctgcagatga gctttactgc c ccgagcacc    2460 gaggccttgg tttctttgac cggccggtcc attttgctga tgtttctggc a acggcaagg    2520 ccgattatct gtgcgttgag aaggacggcc gcacctgggg ctgggtcaat g gggacgatg    2580 gatgggacta cattgatcaa ttcaagtact ccgaggagaa ggacagggcg a atctacact    2640 gggccgacgt caacggcgac ggaaaggccg atatgatctg gacagacaag t tctcgggag    2700 atgggtcggt gtggtacaac cttggccaac gtgatatcaa gggatcgcga t acgaatggg    2760 gaccgcaggg tcccaagtac cgaggggcgg ttgaaggctc atgcacttat t tccctgatc    2820 tgaacggcga cggtcgtgca gacatgcaca gcatctggaa ctccataaac a acacagcgc    2880 agacgtggta caacgaatgt gccaccaaag accacacagg cgatgacggc c cgataacta    2940 accccaatct acctgtatct cctgtaaaag cccccatcga gctcaccccct c attatcagg    3000 acaacagcga gtgcactagg gcccaggtgc agacgctctt tgaagaaatg c aatatgcgc    3060 ttgatgctgc ctcggaagtt gcgtacttta gcggcggcgc atacgaccca t atagggaca    3120 tcttctttgc cgaatcactc accgacagct tgaccttcac tataaatgta a ggtatacgt    3180 tcgaccggat ggtcaccatg atttctgggt cttcgcaatt cgacgacgaa a agttcacga    3240 tcacttgcaa aaaccttcgg ggctgtgacg agaacggctg gttggccatg a tgaacaata    3300 ggaatcggct taatttctgc ccaaagttct tcacagatga gttgaagagt t ccaggtcag    3360 tgctcgcgag gtgcgactca attaatcttc atgatgccca tctcactcga g ccggggcga    3420 ttttgcacga agtaacgcat acggactatg ttatggagat tgtcaatgga g agaatgggt    3480 ggtatcacat atttttttctc attcccaggc cgatactgat tctttcacct t aggaggacc    3540 cgcgattatg tctatggatg gaaaggagct cgagatcttg ccgcagggac c ttcaatcga    3600 cactgtatcg aaagaggcag aaaggctgaa agagccgcta atgagctccg t atagccggc    3660 gatgctaact ggcaacgcag attgctttgc ccagacccaa ataacctcgg g caagaaggc    3720 atctgtgaca gcaagttgtc cgcctacaat gcggattcat gggctcttgt c gtacttggc    3780 gggtactata ccaagatatg tggtcgacag attcccccttc ctgaggagtc t gcttcttcg    3840 gcggatgact ccagctgtcc ggcctacgat gattcgtctt atgatgctga c actgtgtac    3900 ggcgtcaacg attatgttca cttcggtgac tcctacgccg ctgggatggg t acaggaacc    3960 acaaccggtg acagttgccg cgtgggaagt aacagctacg aaagctcgt c caggagtgg    4020 tttgatactg aggatttcac ttataccaac tatgcgtgct ctggagatac a acggttggg    4080 ctgaataaaa agatcgacca gtggctagga caggacccca cggggactac c atggcaacc    4140 ctgacaattg gagggaacga tgtgttcttc agcgatctgg tttccaactg c gtgctaaca    4200 atgtggtggt actcgcttga gcaataccgc cagtggtgtc tggagactga a gagaaagcc    4260 cgcaacctga tgcaggatac agggtctgac ggactcggct cgaaacttag g gctgcgtat    4320
```

-continued

| | |
|---|---|
| gaaaagatcc tggatagatc tggctctagc gtatatctcc ctgttatcct t atttattcc | 4380 |
| tgtcgtgctg tccttcgtcg cgctgacttt actttagtcg ttcaacctct a cgtccctgg | 4440 |
| ctatgtcacc ttcttcaacg aagacaccac cgactgcgac tcaaccacct t ctggtacga | 4500 |
| aagcccacac tacgacccgc agcaatccgg caactatgtg tggctcacga c cgacctacg | 4560 |
| caaggaactc aacgacctcg tccgcatgct caactcgtta atccaatcca c catttccga | 4620 |
| catcaacacc gcccggaata cggagcagat ccattacatc gatatggacg c gcgatttga | 4680 |
| cggccaccgc tggtgcgagc ccggaaccca agaaccagac cccgcaaacc c aaacactta | 4740 |
| cttcttccta tccgcatggc ccgatatcgc gattgttgga gacacgacag c cgagagcac | 4800 |
| gaacgcgacc gagacagacg aaattaccgc gcttatgaac tccggatcga t ccagctgcc | 4860 |
| cgatgcggat acgtgccagg atgcgctggg atctgacccg gatccctatg c ggttttcat | 4920 |
| gtgtgacgtt gcggtccacg tcaaggcgaa ctcgtcgagt ttgatcgcgc a gagcttgga | 4980 |
| ccgagcgaat caggccattg ccaataggga ctatagtagc caggatgtct c ttggtggtt | 5040 |
| gcctagtccc tag | 5053 |

<210> SEQ ID NO 21
<211> LENGTH: 987
<212> TYPE: DNA
<213> ORGANISM: Aspergillus terreus

<400> SEQUENCE: 21

| | |
|---|---|
| atgactctac caaacacttcc taactggata aggatgtgcg tgcatttgtc c cttacacat | 60 |
| ctccatcagc accgttcccc gaaatacgag tctataccta ttaaaagtat c caggctaat | 120 |
| tcacacagaa tcctcatcat cctaaccaca gcctccttct acccgcagat c cggtgcatc | 180 |
| caacttcgaa actccacgca cggcatctcc actgcctaca tcctcttcaa c ctaatcagc | 240 |
| gcaacagaac acttcaccat cctattcgca ttgctggtaa acagcggcgg a gatgtcctc | 300 |
| atccatgagc cccccacgac cggcgacggg ttgaacctgt accagctttt c gcagtgtgg | 360 |
| atgggatgct tagtcctctt ctgccaagca atccatagcc tccacgccaa t ccacgccgc | 420 |
| aaactcatcc tactaaccat atacattcaa tacctatgca tttctatctt a ccagaggtc | 480 |
| atcgacgcaa tcaccactcc cgaggaaacg agaaaacaaa ggccgccaac g ggcgagagg | 540 |
| aactggctga tcggactctt tctttccgcg cacgcgatga ccgtcctgcc a ctatcggcc | 600 |
| gtgctccgca tcgcgggatt catagatcag tcgcgactga tctcgcggcg c agacgggag | 660 |
| cagccatcgg tcttaagcct gacaggcctg gcgtgtcagg ccgtggtctt t gctctagtt | 720 |
| tctggactct gggtactcag ggttcagcag cctgttcctc gaatgccgat g agaagacct | 780 |
| gtggattgga tgtattggta ccatgtaatt gggtggccgg ttgtcgacga t gcggtttat | 840 |
| gcgctgggac aatgggtttt gttttggtat gcggtttgtt ggcgttctcg g ggcgatgct | 900 |
| agggatgaag cagtccatgc tggggagact gatgacctgt taggagagga t gaagggcat | 960 |
| gggtacggcg gaaccgggac ttcttag | 987 |

<210> SEQ ID NO 22
<211> LENGTH: 972
<212> TYPE: DNA
<213> ORGANISM: Aspergillus terreus

<400> SEQUENCE: 22

| | |
|---|---|
| atggtcggga gcaagttagc ccataatgag gagtggcttg acatcgccaa g caccacgcg | 60 |
| gtgacgatgg caattcaagc gcgccagctg cgcctctggc ccgtcattct g cgccccctt | 120 |

```
gtacattggc tcgagcccca gggagccaaa ctccggcgc aggttcgacg a gcccggcaa    180
cttctcgatc ccattatcca ggagcgacgt gcggaaagag atgcctgccg g gcaaaggc    240
attgagccgc ctcgctacgt agactcgatc cagtggttcg aggatactgc c aagggaaa    300
tggtacgatg cagccggggc gcaactggcc atggactttg ctggtatcta c ggaacctcc    360
gacctgctga tcgtgggtt ggtggacatc gtccgacatc cccatctcct t gagcccctc    420
cgtgatgaga tccggacggt catcggccaa ggggttgga cacctgcctc g ctgtacaag    480
ctcaaactgc tggatagttg tctcaaggag tcacagcgcg tcaagcccgt c gaatgtgcc    540
accatgcgca gctatgcatt gcaggatgtg actttctcca atggaacctt t atcccaaaa    600
ggagagctgg tggcggtagc tgccgaccgc atgagcaacc cgaggtctg g ccagagccg    660
gcaaaatacg atccttaccg gtatatgcgc ctgcgagagg accggctaa a gcgttcagt    720
gcccaactgg agaacaccaa cggggaccac atcggcttcg gttggcatcc a cgggcttgc    780
cccggccggt tctttgcctc taaggagatc aagatgatgt tagcctactt g ctcatacga    840
tacgactgga aggtggtccc cgacgaaccg ttgcagtact accgccattc t ttcagcgtg    900
cgcattcatc ccaccacgaa gctcatgatg cgccggcgcg acgaggatat c cgccttcct    960
ggttcactat ag                                                        972

<210> SEQ ID NO 23
<211> LENGTH: 771
<212> TYPE: DNA
<213> ORGANISM: Aspergillus terreus

<400> SEQUENCE: 23
atgcgttacc aagcatctcc agcgctggtg aaggcgcctc gagcgcttct t tgcatccat     60
ggggctggct gctctcccgc catcttccgc gtgcaattgt ctaagctccg g gctgcgctg    120
cgcgaaaact ttgaattcgt ctacgtgaca gctccgttcc cttcctctgc a gggcctggg    180
attctccccg tcttcgccga cctagggcca tattactcct ggtttgaaag c agcagcgac    240
aacaatcata atggaccctc cgtgagcgaa cgcctcgccg ccgtccacga c cccatccgc    300
cgcaccattg tcgactggca gactcaacac ccccacatcc ctatcgtggg t gctatcggt    360
ttctccgaag gtgccctggt gacgaccttg ctcctctggc agcagcagat g ggtcacctg    420
ccctggttgc cccggatgag tgttgcgctg ttgatctgtc cctggtatca a gacgaggca    480
agccagtata tgaggaacga agtgatgaag aaccatgacg acgacaacga c agcaaagat    540
accgagtggc aggaggaact ggtcattcgg ataccgacat tacatctgca g ggtcgcgat    600
gattttgcgc tcgcaggatc gaagatgctg gtggcgcgcc atttctcccc c gagaggcg    660
caggtattgg agtttgctgg gcagcatcag tttcccaatc gaccgcgcga c gtgttggag    720
gtcattaatc gttttcgtaa gctgtgtgtg acggcccaga cattggagta g           771

<210> SEQ ID NO 24
<211> LENGTH: 1253
<212> TYPE: DNA
<213> ORGANISM: Aspergillus terreus

<400> SEQUENCE: 24
atgggcgacc agccattcat tccaccaccg cagcaaacag cgctgacggt a aatgaccat     60
gatgaagtca ccgtctggaa tgccgcaccc tgccccatgc tgccccgcga c caggtatac    120
gtccgcgtcg aggccgtggc gatcaatccc agtgacacga agatgcgcgg a cagtttgcc    180
```

-continued

| | |
|---|---|
| acgccctggg cgtttctcgg aacggactat gccggcacgg tcgtcgcagt g ggttcggac | 240 |
| gtgactcata tccaagtggg tgaccgggtc tacggggcac agaacgagat g tgcccacgc | 300 |
| accccggatc aggggggcatt ctcgcagtac acggtcacgc gaggccgtgt t tgggccaag | 360 |
| atccccaagg gcttgtcgtt cgagcaggct gccgcgctac ctgcgggcat c agtaccgct | 420 |
| ggattggcga tgaagttgct tgggctgcct ttgccatcgc cttcggcaga c cagccaccc | 480 |
| acccactcca agccggtgta tgtgttggtc tatgggggca gtacggccac t gccactgtc | 540 |
| actatgcaaa tgctccgcct gtaatgcttc ccttgtcctg agactttcct c tccgttggt | 600 |
| cgtgggctgt acaagcgatg gttatactaa gatccgctgg caggtccgga t atattccaa | 660 |
| ttgcaacatg ctccccccac aatttcgacc tggccaaatc gcgcggcgca g aggaggtct | 720 |
| ttgactatcg ggccccgaat ctcgcgcaga cgatcgtcag tgaaccctg c caccgctct | 780 |
| accccctccca gtccactttg gccttacaga acagactatt gatattcttc t agcgtacct | 840 |
| acaccaagaa caatctccgc tatgctctcg actgtatcac caacgtcgag t ccaccacat | 900 |
| tctgcttcgc agccatcggc cgcgcggggg ggcactacgt ctccctgaac c cgttccctg | 960 |
| aacacgcggc cacgcgcaag atggtcacga ccgactggac cctggggccg a ccatctttg | 1020 |
| gcgagggatc aacctggccc gccccctatg ggcgtcccgg cagtgaggaa g agcggcagt | 1080 |
| tcggcgagga tctgtggcgc atcgcggggc agctcgtcga agatggacgc c tcgtccatc | 1140 |
| atccgttgcg cgtggtgcag ggcggcttcg atcacattaa gcaaggcatg g agctcgtcc | 1200 |
| ggaagggaga gctgtcgggg gagaaactcg tggttcggct cgaggggccg t aa | 1253 |

<210> SEQ ID NO 25
<211> LENGTH: 1394
<212> TYPE: DNA
<213> ORGANISM: Aspergillus terreus

<400> SEQUENCE: 25

| | |
|---|---|
| atgggatcca tcattgatgc tgctgcggca gcggatccgg ttgttctgat g gaaaccgcc | 60 |
| ttccgcaagg ccgtgaaatc caggcagatc cccggggcgg tcatcatggc c cgagattgc | 120 |
| agtggtgaga gaccccaatc ggaccccttt gcgacaatta caagcacacc g agacgaatg | 180 |
| acagcgggac atacctaggc aatctaaatt atacgcgctg cttcggggct c ggacggtgc | 240 |
| gacgggacga gtgcaatcag ctgccgccgc tacaggtcga caccccctgc c ggctcgcca | 300 |
| gtgcgaccaa gctgctgacc acgatcatgg ccctacaatg catggagcgc g gtctcgtgg | 360 |
| acttggatga gacggtggat aggctgcttc cggatttgag cgcgatgccc g tgctggagg | 420 |
| ggtttgacga cgcgggaaac gcaagattgc gagagcgtcg ggggaagatc a cgctgcggc | 480 |
| acctgctgac gcatacatcg ggactgtcgt acgtcttcct ccatccgttg c tccgggaat | 540 |
| acatggccca gggccacctc cagtcggcag aaaagtttgg catccagagt c gcctggcgc | 600 |
| cgccggccgt caacgaccct ggggcggagt ggatctacgg cgccaacctg g actgggcgg | 660 |
| gtaagctcgt cgagcgggcc accggcctcg acctggagca gtacctgcag g agaatatct | 720 |
| gtgcgccgct gggcatcacc gacatgacct ttaagctgca gcaacggccg g atatgcttg | 780 |
| cgcgccgggc cgaccaaacg caccgcaact cggcggatgg gcgcctgcgc t acgacgact | 840 |
| cggtctactt ccgggccgat ggagaggagt gcttcggcgg ccagggggtg t tctcgggcc | 900 |
| ctgggtccta tatgaaggtg cttcactcgc tgttgaagcg agacgggctc c tgctgcagc | 960 |
| cacagaccgt ggacttgatg tttcagcctg ccctcgagcc gcgactcgaa g agcagatga | 1020 |
| accagcacat ggacgccagc ccacatatca actacggtgg gccgatgccc a tggtccttc | 1080 |

-continued

```
gtcgcagctt tgggctgggg gggatcatcg ccttggagga tctggacgga g agaactggc     1140 gccgaaaagg ttccttgacc tttgggggtg gcccaaacat tgtgtgggta a gctcggctc     1200 ctagattcct ttggtttatg tcaccttcaa tgttgatcca gcctactaag t gctattgta     1260 attagcaaat cgaccccaaa gccggcctgt gcacccttgc gttcttccaa c tggaaccct     1320 ggaatgaccc ggtctgtcgt gatctgacac gcacattcga gcatgccatc t atgcgcagt     1380 accagcaggg ttaa                                                        1394
```

<210> SEQ ID NO 26
<211> LENGTH: 3504
<212> TYPE: DNA
<213> ORGANISM: Aspergillus terreus

<400> SEQUENCE: 26

```
atggatccgg tggttagaaa gccggaccct ggcggggtgc agcatcgagt g accaaagca      60 ttgcgtgcca ttgtgggaca cgcgtgtcga catcccattc acactctgct a gtcacggcg     120 ctgaccgcgc aacgacccca tcttcatgtg ctggaaggga catatcaggc t actcacaga     180 ggtctggccc cctgggccaa ggaaaccccc ttgaacgtcc agtcatttct c tggggaagc     240 cgcactgtta gctgggagga ggctagcgca tggaaatggc agatagacga c cgacctaag     300 gtgccggagg atggccaggt atgatagatc tcctgcgctc cattggtccg a gaaattctg     360 cgtgctgacc ggaccgtccc tgtgctactc tcaattagtc tgactttcac t gggctcttg     420 tcaccctcga tctaccgggt gcgtctgtcg acgccagtat cccctcccta t caaacacgc     480 tctcagggtt cctcggtgcg aacagacca cgcccacccc cgattcatcc c cctcaccgc     540 atcattccgc gttgacgttt cgagttccct actcccaact agatggcttt c tacaggctg     600 tcgaaattat accctcggaa aaagaggatg atagttggag actgaggtct c ctcgcgaag     660 aaggaagtcc caggtcactg ggacactggc tcggaagctc atggctgtca t ccttcatc     720 gtgttcacca tgcggagaca gtcgacttgg tgatcatagg gctcagttac c tagccatga     780 atatgactgt ggtctctctc tttcgggtga tgcgccacct cggctcacgc t tctggttgg     840 cagcctcggt cctgctgtct ggtgcctttg cttttgtact cgggcttgga a tcacgacta     900 catgcgacgt gcccgtcgac atgcttcttc ttttcgaagg aatcccgtac c tcgttctga     960 cagtgggctt tgagaagccg atccaactaa cccgtgctgt tctctgcgtg t cggaagaac     1020 tgtggggcgg ggggcagcgg caagttccca atggcgccag cagtgatgat a gccggcaaa     1080 accaattgat tcctaacatc atccaactcg cggttgatcg agagggtgg t atattgtgc     1140 gatcttacct cctggaaatc ggcgcgttgg cattaggggc ggtccttcgg c caaaggata     1200 gtcttggcca ttttttgcttc ctggcggcat ggacactcct gattgatgcc g ttctacttt     1260 ttaccttcta tgccaccatt ctttgcgtga aattagagat cacgcgaatc c ggagcccag     1320 gagggcttgg tcaagttaat gccaagcatc cttcggggat ttttgggcac a aggtcaagt     1380 cgacaaacat cacctggtgg aagctattga cgtgggcgc cttcgttcta t gtcacttcc     1440 tccaattgtc gcccttcttc tatcgggtca tgggagaata tatggctaat g gtactctgc     1500 cccctactgc tgtcagtcct ttcaaagaag cggcaacgg actcaacgag a tctacctaa     1560 cggcgcgcgt cgagggggttt gagacacgcg taaccgttct gccgccactg c agtacgtct     1620 tggaatcagc tgggttcaat atatcagcca ctaaacgttc tacatttgac g tgtgctcg     1680 atggattgga aagcccgctg ggtcgactat gtctcatggg cgcattggtc g ttagcctgg     1740
```

```
tcctcaacaa ccacctgatc cacgctgctc gctggcatgc ttggcccaa g cgagagagt    1800 ccgccgtccc tgatggctcc tacttgtcgg tgccatgctc tgccactgcc c ctgaagtct    1860 gtactcgccc cccagaagaa acagaggccc tcctcaaatc gaaccaagca g aatctctga    1920 cggacgacga gctggtggaa ctgtgtctcc ggggtaagat cgcggggtac a gtttagaga    1980 agactctcga gcggattgcg gcgggatcat cccgctcggt gacccggctg g aggcattta    2040 cgcgtgccgt gcggattcgc cgtgccgctg tgtcgaaaac gccctccact c agaacctct    2100 gcagcggcct ggcggagtca ttgctcccctt atcgcgacta taactacgag c ttgtgcatg    2160 gcgcctgctg tgagaacgtg gtcgggtacc tgcctctgcc cctgggagtg g ccggaccca    2220 tggtgatcga tggacaggcg ttgttcattc ccatggccac aaccgagggc g tgctcgttg    2280 cgagcgccag tcgcggatgc aaagcgatca atgctggcgg cggtgccact a ccatgctca    2340 aaggtgatgg tatgacgcgt ggtccctgtc tgcgattccc gtcggcccaa c gtgcagctg    2400 aagcccagcg ctgggttgag tctcctctcg ggcacgaggt tctggcggcc g ccttcaacg    2460 cgaccagccg gtttgcgcgg ctccaaaccc tgacggtggc ccaggcgggc a tctatctct    2520 acatccggtt ccgcaccacc acgggcgacg cgatgggcat gaatatgatt t cgaagggcg    2580 ttgaaaaagc cctggaggcg atggccgccg agggtggatt tccgacatgc c atacggtta    2640 ccttatctgg caatttctgt tccgacaaga aatccgccgc cattaactgg a tcggcggcc    2700 gcggcaagtc cgtcatcgcc gaagccacga tccccgcgga gactgtccga c aggtcctga    2760 agaccgacgt cgatgcgctg gtcgagctca acacggccaa gaacctggtc g ggagtgcca    2820 tggcggcag cctgggcggc ttcaacgccc atgcctccaa cctcgtccag g cggtgtttc    2880 tggccactgg tcaggatccg gcgcagaatg tggagagcag tagttgcatt a cgaccatga    2940 aaaagtaggt agcttctcta cgttttgatt ttctcctccc ggttatatat a ttcacgtgg    3000 gtgtgtttgc taatgtgggg tttctagcat cgatggaaac ctgcacatcg c tgtctcgat    3060 gccctcgatg gaggtcggca cgattggcgg aggcaccatt cttgaggccc a gggagccat    3120 gttggacttg ctaggtgtcc ggggcgcaca ttccacggag cctggcgcca a tgcgcgccg    3180 cttggcccgc attgtcgccg cggccgtgct ggctggcgag ttaagtacct g cgcggctct    3240 tgcggcgggt cacttggtca atgcccatat gcaacacaat cgcagtgcgg g tgccacagt    3300 caagaaatga agggatcgct gtgattgatt ctcggggcag cttcaaagga c gctatctcc    3360 ggtacagagt acggagcaat tagaacaccg gtatatgtgg taatcttaga a catgcggga    3420 gacatccatt tcgtgcaaat cgaatataaa aatacctacc tacgtagaaa a gtacctacc    3480 ttgtcatgta acttaggtag gtaa                                            3504
```

<210> SEQ ID NO 27
<211> LENGTH: 1512
<212> TYPE: DNA
<213> ORGANISM: Aspergillus terreus

<400> SEQUENCE: 27

```
atggctgcag atcaaggtat attcacgaac tcggtcactc tctcgccagt g gagggttca     60 cgcaccggtg gaacattacc ccgccgtgca ttccgacgct cttgtgatcg g tgtcatgca    120 caaaagatca aatgtactgg aaataaggag gttactggcc gtgctccctg t cagcgttgc    180 cagcaggctg gacttcgatg cgtctacagt gagcgatgcc ccaagcgcaa g ctacgccaa    240 tccagggcag cggatctcgt ctctgctgac ccagatccct gcttgcacat g tcctcgcct    300 ccagtgccct cacagagctt gccgctagac gtatccgagt cgcattcctc a aatacctcc    360
```

-continued

```
cggcaatttc ttgatccacc ggacagctac gactggtcgt ggacctcgat t ggcactgac      420 gaggctattg acactgactg ctggggctg tcccaatgtg atggaggctt c agctgtcag      480 ttagagccaa cgctgccgga tctaccttcg cccttcgagt ctacggttga a aaagctccg      540 ttgccaccgg tatcgagcga cattgctcgt gcggccagtg cgcaacgaga g cttttcgat      600 gacctgtcgg cggtgtcgca ggaactggaa gagatccttc tggccgtgac g gtagaatgg      660 ccgaagcagg aaatctggac ccgtgcgtcg ccgcattccc caactgcttc c cgtgagagg      720 atagcacagc gccgacaaaa cgtatgggca aactggctaa cagacttgca t atgttctca      780 ctagatccca tcggaatgtt tttcaatgcg tcacgacggc ttcttactgt c ctgcgccaa      840 caagcgcagg ccgactgcca tcaaggcaca ctagacgaat gtttacggac c aagaacctc      900 tttacggcag tacactgtta catattgaat gtgcggattt tgaccgccat a tcggagttg      960 ctcctgtcgc aaattaggcg gacccagaac agccatatga gcccactgga a gggagtcga     1020 tcccagtcgc cgagcagaga cgacaccagc agcagcagcg ccacagcag t gttgacacc     1080 ataccttct ttagcgagaa cctccctatt ggtgagctgt tctcctatgt t gaccccctg     1140 acacacgccc tattctcggc ttgcactacg ttacatgttg gggtacaatt g ctgcgtgag     1200 aatgagatta ctctgggagt acactccgcc cagggcattg cagcttccat c agcatgagc     1260 ggggaaccag gcgaggatat agccaggaca ggggcgacca attccgcaag a tgcgaggag     1320 cagccgacca ctccagcggc tcgggttttg ttcatgttct tgagtgatga a ggggctttc     1380 caggaggcaa agtctgctgg ttcccgaggt cgaaccatcg cagcactgcg a cgatgctat     1440 gaggatatct tttccctcgc ccgcaaacac aaacatggca tgctcagaga c ctcaacaat     1500 attcctccat ga                                                          1512
```

<210> SEQ ID NO 28
<211> LENGTH: 2161
<212> TYPE: DNA
<213> ORGANISM: Aspergillus terreus

<400> SEQUENCE: 28

```
atgacatccc accacggtga aacagagaag ccacagagca cacggctca a atgcagata       60 aatcatgtca ctggcctcag gctaggcctg gttgtggttt cagtcactct g gtggcgttt     120 ctgatgctct tggatatgtc catcattgtc acggtcagca tggcaccagc c tggagattg     180 ctccgagcct tggagacaac tgactcttca cattcgcagg cgattcctca c attaccgcc     240 cagtttcatt ccctgggcga tgtcggatgg tacggaagtg cgtatcttct a tcaaggtga     300 tcgatttttcc aacccatgcc ctcttccttt tctccagccg ggtttctatt g actccacga     360 cacgctctag ctgtgccctc caaccttggg caggcaaact atacactctg t tgaccctga     420 aatacacctt cctcgctttt ctcgggttgt ttgagattgg atcggttctt t gcggcactg     480 ctcgttcgtc aaccatgttg attgtagggc gagcagtggc cggaatggga g gtcgggc     540 tcaccaatgg cgcaatcacc attctgtcgg cggcagctcc aaagcaacag c aaccgcgta     600 agtactgata gccagaccta tctcaaccgt tgttatgcta tgctgacccg g atatttaca     660 catagtcttg attgggatca tgatgggccg tcagttcgcc aacccattgg g atccccgga     720 aatcatcaag catagtttct gactccattc ccagtaagcc aaatcgccat t gtatgtgga     780 ccgttgcttg ggggtgcttt cacgcagcac gcaagttggc ggtggtgtat g tatcccat     840 tggatttatc ggttcagtgc ttgctttctc aaaggacctt ggctacgact c cgccacgtc     900
```

-continued

```
aagatctttc gctcacggtg attctggtcc aggttttttac atcaaccttc c cattggggc    960 gtttgccaca tttctccttc tcgtcatcca gatccccaac agattgccat c cacgtcgga   1020 ttcaaccaca gacggcacaa accccaagag aagaggggct cgggacgtct t gacccaact   1080 ggatttcctt ggattcgtgc tcttcgccgg ttttgcgatc atgatatctc t tgctttgga   1140 gtggggtggg tctgattatg cgtggaatag ttccgtgatc atcggcttgt t ctgtgcggc   1200 gggcgtgtcg ctggtgctgt tcggatgctg ggaacggcat gtcggcggtg c agtggccat   1260 gattcccatt tccgtggcca gtcgtcgcca agtctggtgc tcctgcttct t cctcggctt   1320 tttttccggg gccctactta ttttctccta ctacctgcct atctacttcc a ggcggtcaa   1380 gaatgtttct cccaccatga gtggagtgta tatgctgccg ggcattggtg g acagatcgt   1440 catggcgatt gtgacgggtg caatcagttg agttgccacc attccaccac c tttcttcgc   1500 ttataaccta tggcgttact gacaaattga gggtggtagt cggtaaaaca g gctattacg   1560 ttccgtgggc gctcgcaagc gggatccttg tgtccatatc cgccggactg g tatcgacct   1620 tccagccgga aacctcgatt gcagcatggg tcatgtatca gttcctggga g gcgtgggcc   1680 gaggatgcgg aatgcaaacc gtaggtgacc tggatcgttt ccatcggttt g cgccgcact   1740 cttatgcaaa tgctcattga ctcggttgtc cctcctttag cctgtcgtcg c cattcaaaa   1800 tgcgctgcct ccacaaacga gccccatcgg catttcgcta gccatgttcg g ccagacatt   1860 cggtggctcg cttttctca ccctgaccga attggttttt agcaatggtt t ggactctgg   1920 tctgcgccaa tatgcgccaa ccctcaatgc acaggaggta acagccgcag g ggccaccgg   1980 cttccgccaa gtggtccccg ctcctctcat ctctcgggtc ctcttagcat a cagtaaagg   2040 cgtggaccat gcattctacg ttgcggtcgg tgcgtctgga gctaccttca t cttcgcctg   2100 gggtatgggc cggcttgcct ggagaggctg gcggatgcag agaaaggac g gagcgaatg   2160 a                                                                  2161
```

<210> SEQ ID NO 29
<211> LENGTH: 8035
<212> TYPE: DNA
<213> ORGANISM: Aspergillus terreus

<400> SEQUENCE: 29

```
atgacaccat tagatgcgcc cggtgcgcct gctcccatag ctatggttgg c atgggctgc     60 agatttggcg gaggcgcaac agatccccag aaactgtgga aattgctgga g gaaggaggg    120 agcgcctggt ctaagattcc tccttcacga ttcaatgtcg gcggggtcta c caccccaat    180 ggccagcggg taggatcggt gagtatgaag gattctgggt tgagcatttt t gaggcccat    240 atcttcctgt tcagaacgat aggcgttgac tgcgagtaga tgcacgttcg c ggtggacac    300 tttctcgacg aagacccggc tcttttcgat gcctcatttt tcaatatgag t actgaagtt    360 gccagtgtac gtcccgcgat cgttgtccag ttgtgtatgg atcagaagcg g aataaaccc    420 atgctaagac tgccgaatag tgtatggacc cccagtaccg actcatactt g aagtcgttt    480 atgaggcgct cgaagctggt atgtattata ttccttggtt tcccacgtgg g tattaactc    540 cccatggctc cgcagcggga attcctctcg aacaggtctc cggctccaag a ctggggttt    600 tgcaggaac catgtatcac gactaccaag gctccttcca gcgccaacca g aagcccttc    660 cacggtattt cataacagga aatgctggca ccatgctcgc gaatcgcgtc t cccactttt    720 atgaccttcg tgggcccagt gtctcgatcg acactgcctg ttccacaacc t taacagcct    780 tgcatcttgc cattcagagc ttgcgagctg gagaatctga tatggcgatt g tcgctggcg    840
```

```
cgaacctgct acttaatcct gacgtcttta ctaccatgtc caaccttggg t gagtctggt      900 gttcaatcca tctagtgatc agcattcttg ttgcacagac aatatgtgat g ttaactgtg      960 atgtgctgcg accagcttcc tttcgtccga tgggatttcc tactcatttg a ctcgagagc     1020 ggatggctat ggtcgcggag aaggagtggc tgcgatcgtc ttgaagactc t gcccgatgc     1080 ggtgcgagac ggagacccga tccgcctcat agtgcgcgaa acggcaatca a ccaagacgg     1140 ccggacccca gccatcagca cgccgagcgg cgaggcccag gagtgcctga t ccaagattg     1200 ctatcagaag gcccagttgg acccaaaaca gacttcgtac gttgaggccc a tgggacggg     1260 aaccagagca ggagatccgc tggagcttgc agtcatctcg gccgcgtttc c gggacagca     1320 gatacaggtg ggctccgtga aagccaatat cgggcataca gaggctgtca g tggtctggc     1380 gagtttgata aggtggctc tggctgttga aagggggtt atcccgccta a tgcaaggtt      1440 cctccagccg agcaagaagt tgctcaagga cactcatatc caggtagcat t atcttcacg     1500 atttttcct ctcattctat tctttctatt ccagctcctc gctgatttac a aacagattc      1560 cactgtgtag ccaatcatgg ataccaaccg atggtgtccg tcgcgcatca a taaacaact     1620 tcggtttcgg aggcgcaaat gctcatgcaa tcgtggagca atatggcccg t ttgcagaaa     1680 catcgatctg cccacctaat ggttattctg caactatga tggcaattta g gaacggatc      1740 aagcgcatat atatgtgctg agtgccaagg atgagaacag ttgcatgaga a tggtttcaa     1800 ggctgtgcga ctatgctacc cacgccagac cagccgacga tttgcaattg c tcgcgaata     1860 tagcatacac gcttggttct cgtcgctcga acttccgatg gaaggcagta t gtacggcac     1920 acagcctcac gggtcttgcc cagaatttgg cgggagaagg catgcggcca a gcaagtcag     1980 ccgaccaagt aagactggga tgggtgttca caggccaggg agcgcaatgg t ttgcaatgg     2040 gtcgtgagtt gattgagatg tatcctgtct ttaaagaggc cctgctggaa t gcgatggat     2100 atatcaagga aatggggtca acctggtcca ttataggtaa agaccccgcaa c aagtccccg     2160 gcccaggcta tggaaagcac tcactcatgt caccattgca gaggaactca g tcgccctga     2220 aacggaaagt cgcgttgatc aggcagaatt cagtctgcca ttgtctacgg c tcttcaaat     2280 tgcgcttgtt cgtctgctct ggtcgtggaa catccaacca gtagccgtca c tagtcactc     2340 cagcggagag gcagctgcag cgtacgctat cggggcacta acagcccgct c ggccattgg     2400 aataagctat atacgcggtg cattgacagc aagagaccgc ctggcgtcgg t acataaggg     2460 gggcatgttg gctgtcggat tgagccgcag tgaagtgggt atatacatca g acaggttcc     2520 attacagagt gaagaatgct tggtggtggg gtgtgtcaac agcccgtcga g tgtgacggt     2580 ctcgggagat ttgtccgcca ttgccaagtt ggaggaactg ctccatgctg a tcgtatatt     2640 tgcgagacgg ctgaaagtca cccaagcctt tcactccagc cacatgaact c gatgacaga     2700 tgctttccga gccggtctta cagaactctt cggagcagac cccagtgatg c agcaaacgc     2760 cagtaaagat gtgatctacg cttctcccag aaccggggcc cgcctgcacg a catgaatcg     2820 tcttcgggat cctatacact gggtcgaatg catgcttcac ccggttgagt t cgaatcagc     2880 attccgtcga atgtgcctgg acgaaaacga ccacatgcca aaggtcgata g ggtcattga     2940 gattggacct cacggagcgc ttggaggccc gatcaagcag atcatgcagc t tccagagct     3000 tgccacgtgt gacatccctt atctgtcctg tctttctcgt gggaagagct c tctgagcac     3060 ccttcgcctt ctcgcatcag aacttatccg ggccggattt cctgttgact t gaatgcgat     3120 caactttccc cgcggatgtg aagcagctcg ggtccaagtg ttgtctgatc t accgcccta     3180
```

-continued

```
cccttggaac cacgagacca gatactggaa agagccgcgc atcagccaat c tgcccggca      3240
gcggaagggc ccagtccacg atctgatcgg attgcaggag ccgttgaacc t gccgttggc      3300
gcggtcatgg cacaatgtgc ttcgtgtgtc agatttgcca tggctacgcg a ccacgtcgt      3360
cggctcgcat attgttttcc ctggggctgg gttcgtgtgt atggcagtga t gggaatcag      3420
cacgctctgc tcgtccgacc atgaatctga cgacatcagt tacatcctac g cgacgtgaa      3480
cttttgcgcag gccctgattc tacctgcgga cggggaagaa ggaatagatc t gcgcctcac      3540
gatttgtgct cccgatcaga gtctgggttc acaggactgg caaagattct t agttcattc      3600
gatcactgct gacaagaatg actggacgga acactgtacg ggacttgttc g agcagagat      3660
ggaccagcct ccctccagtt tgtcgaacca acaacggata gacccacggc c atggagccg      3720
taaaacggcg ccgcaggagc tgtgggactc actacatcgg gtgggaattc g tcatgggcc      3780
cttttttcga acattacgt gcatcgaaag cgacgggcga gggtcatggt g tacatttgc      3840
catcgcggac acggcctccg caatgccaca cgcctacgaa tcccagcaca t tgttcaccc      3900
aaccacacta gactctgcag ttcaggcagc ctataccact cttccattcg c tgggagccg      3960
gatcaaatct gcgatggtcc ccgctcgcgt cggctgcatg aagatttcct c ccgacttgc      4020
agatttggag gccagggaca tgctgcgcgc acaagcgaag atgcacagcc a aagtccttc      4080
cgcattggta accgatgtag cagttttttga tgaggcagat ccggttggag g gcctgttat      4140
ggagctcgaa gggctggtct ttcagtctct gggggcaagt ctgggcactt c tgaccggga      4200
ctccaccgac cccgggaata cttgcagctc ctggcattgg gctccagaca t cagcttagt      4260
taacccccggc tggcttgaaa aaaccctggg cacaggtatt caggagcacg a gatcagcct      4320
catattggag cttcgacggt gttcggtgca cttcattcaa gaggccatgg a aagtttgag      4380
cgtaggcgat gtcgagaggc tgagtggtca tctggccaaa ttctatgcgt g gatgcagaa      4440
acaactggcg tgtgcccaaa atggcgagct ggggccagag agctccagct g gactcggga      4500
tagcgagcag gcaagatgca gcctccgctc tagagtggtt gctggtagca c caacggcga      4560
aatgatctgt cgcctgggct ccgtgctccc cgctatccta cgtcgggaag t tgatccgtt      4620
ggaggtgatg atggatggcc acctgttgtc ccgctactat gtcgatgccc t caagtggag      4680
tcggtccaac gcgcaagcca gcgagctcgt gcgcctctgc tgccacaaaa a cccgcgcgc      4740
tcgcatactg gaaatcggcg gaggcaccgg gggttgcacc cagctggtcg t ggactcctt      4800
gggcccaaat ccgccggtag gccgctatga ctttactgac gtctcggccg g gttttttga      4860
agcagcccgc aagcggttcg cgggatggca gaatgtgatg gattttcgga a gttggacat      4920
cgaggacgat ccagaagcgc aggggtttgt gtgcggatcc tacgacgtgg t gttggcttg      4980
tcaggtcctg catgccactt ctaacatgca gcgcacattg actaatgtgc g caagctgtt      5040
gaagccagga ggcaaactca ttcttgtcga accaccagaa gacgagcttg a cttgttttt      5100
cactttcggg cttctgcccg gctggtggct cagcgaagaa ccagaaagac a gtcgactcc      5160
gtcactaagc cctacgatgt ggcgcagcat gctgcacact actggattca a tggtgtgga      5220
agttgaggct cgtgactgcg atagccacga gttctatatg attagcacca t gatgtccac      5280
ggccgtacag gcgactccga tgtcatgctc ggtcaaattg cctgaagtgc t cttggtcta      5340
tgttgactca tctacgccca tgtcttggat atcagatttg cagggagaga t cgcggcag      5400
gaattgttcc gtcacttcgc tacaggcact tcgtcaagtt cctcctaccg a gggccaaat      5460
atgcgtattc cttggagagg tggaacactc catgcttggt tcagtcacca a cgacgactt      5520
cacactttg acctcaatgc tacagctggc tgggggaact ttatgggtca c ccaaggagc      5580
```

-continued

```
gacaatgaag tctgatgatc ccctgaaggc tctacacctc ggattactac g taccatgcg    5640 taatgaaagc catggcaagc gatttgtctc acttgacctc gacccttcgc g taatccatg    5700 gacaggcgat tcgcgcgatg ccattgtcag tgttctggat ttaattagca t gtcagatga    5760 aaaggagttt gactatgcag agcgggatgg agttatccat gttcctcggg c atttagtga    5820 ctccatcaat ggaggcgagg aagacgggta tgccttggag ccattccagg a cagccagca    5880 tctcctgcga ctagatatac agactcctgg gctcctcgat tccctgcact t cacaaagcg    5940 caatgtggac acatatgaac cagataaatt accggacgac tgggtagaga t tgaaccgag    6000 ggcgtttggt cttaacttcc gtgacatcat ggtcgcgatg ggtcaattgg a atcaaacgt    6060 catgggcttc gaatgcgccg gcgtggtac aagtctcagc gagacagcaa g aacaattgc    6120 acccgggctt gcggtcggag atcgggtttg cgccctcatg aacggacact g ggcgtcgag    6180 ggtgaccaca agccggacca acgtggtgcg cattccagag actcttagtt t cccgcatgc    6240 tgcctccatc cctctggcct tcacaacagc ttacatttca ctttacaccg t gcccgcat    6300 tctgccaggt gaaacggtgt tgatccatgc cggggcagga ggcgtaggcc a ggcggccat    6360 tattcttgct caattaaccg gtgctgaagt ctttacaact gctggcagtg a gaccaagcg    6420 taaccttttg atcgataaat tccacctcga ccctgatcat gtcttctcga g cagggactc    6480 cagcttcgtc gacggtatca agacccgcac ccgtggcaag ggggtggacg t ggttttgaa    6540 ctcgctagct gggcctctcc ttcagaagag cttttgactgt ctggctaggt t tggtcggtt    6600 tgtagaaatc ggcaagaagg atcttgagca gaatagccga ctcgacatgt c gacgttcgt    6660 ccgcaatgtc tccttctcct ccgttgatat tctctactgg cagcaagcga a gcccgctga    6720 aatcttccag gcgatgtccg aggtcatctt gctgtgggag cgaacggcaa t cggcctgat    6780 tcatccaata tcagagtatc ctatgtcggc cctggagaag gcctttcgca c tatgcagag    6840 cggccagcac gttgggaaga ttgttgtgac agtagccccc gatgacgcgg t cctcgttcg    6900 tcaggaacga atgccactat ttctgaagcc taacgtgtcg tatcttgttg c tgggggcct    6960 gggtggtatc ggacggcgga tctgcgagtg gctggtcgat cgcggggcgc g atatctcat    7020 cattctgtct cgaactgctc gcgtggaccc ggtcgtgacg agtctccaag a gcggggctg    7080 caccgtttct gtacaggcgt gtgatgtggc cgatgaaagc cagcttgaag c ggctctcca    7140 acagtgtcgg gcggaggaaa tgcctccgat tcgggcgtc atccaagggg c aatggttct    7200 caaggacgcc ctcgtctcgc aaatgacggc ggacgggttc catgccgccc t gcggcccaa    7260 ggttcaggga agttggaatc tgcaccgaat tgcatcggac gtggatttct t cgtgatgct    7320 ctcatccttg gtgggtgtca tgggaggcgc aggacaagcc aactacgcgg c tgccggagc    7380 gtttcaggac gcgctcgcag agcaccgcat ggctcacaac cagccagcgg t caccatcga    7440 cctcggaatg gtccagtcaa ttgggtatgt agcagagaca gattctgctg t ggcggaacg    7500 actccaacgg atcggctatc aacccttgca cgaagaggag gttctggacg t cctcgagca    7560 agctatatct cctgtgtgtt cccctgccgc acccacacgg cctgctgtca t cgtcaccgg    7620 catcaacacc cgcccaggcc ctcactgggc acacgccgac tggatgcaag a ggctcgctt    7680 tgcgggatc aagtatcgtg atccgttgag ggacaatcat ggagctttgt c gctgacccc    7740 ggcggaagat gacaatcttc acgccaggct gaaccgtgca atcagccaac a ggagtcaat    7800 cgccgtgatc atgaggcga tgagctgcaa gctcatctca atgttcggcc t gacggatag    7860 cgaaatgtcc gccactcaga cattggcggg gatcggcgtg gactccctgg t cgccattga    7920
```

-continued

| gctccggaac tggatcacag ctaagttcaa tgttgatatc tcagttttcg a gttgatgga | 7980 |
| gggccgaacg atcgccaaag tcgcggaagt ggtgctgcag agatacaaag c ttag | 8035 |

<210> SEQ ID NO 30
<211> LENGTH: 888
<212> TYPE: DNA
<213> ORGANISM: Aspergillus terreus

<400> SEQUENCE: 30

| atggcgacgc aggaattctt aagcgatgtc tcctccggat tcttgtctgc t gaagccata | 60 |
| aggtacagag tgaagacggg tgtatccatg gatggatgga tgtatgtgga g atggcacct | 120 |
| tacatataaa tatacatcat atcaggaaaa ggggatattc gtgtaactct g tgcgaaccg | 180 |
| acgataaaca tcacttaaga cacctaacca atatagggtt agacacgcct c cgtgtccca | 240 |
| aatcccttcc ggctgcgcac tcggcggtag catcttgtct cacgttcgtt c cgccggacc | 300 |
| catgtgaaaa ttgggaggcg ctgcaggtag cgtgggacaa ggcttgttgc a ggaatccaa | 360 |
| cgccgttgtt ctttatctgc gtttctcttc tgttttcttt ctattccctc t ggctgcagc | 420 |
| gtggcgggtg cgggcgatat ggtgggttgc accgtgtctc taaagtgttt c ccaaagtat | 480 |
| ggcccgacga catggattcc cagctaccct caagactaca aaccttagta a gtagtaagt | 540 |
| agcttcatag acctatccta attaacctac actaactaaa cccagcacgt c tgggggtt | 600 |
| tcaacccgta atctgcagca gatcctagag cgtaaacccg aacctgcccc a aacaactct | 660 |
| acatacatct caaagggcta tgcaacattc ttcaaccaat tttccttacc a tccgtagat | 720 |
| gttacacaga tcctcaatca gacgttgcag caccacgatg ttgagactat t aacctggat | 780 |
| tgtggcagtg gcctcttaac cctgcggacc cagctaagga tcttattgat a gggaaacct | 840 |
| aagataataa aaccattttc cggtctacgg acgagcatta atgaataa | 888 |

<210> SEQ ID NO 31
<211> LENGTH: 2478
<212> TYPE: DNA
<213> ORGANISM: Aspergillus terreus

<400> SEQUENCE: 31

| atggagagtg cagagctgtc gtcgaagcgg caggcatttc ctgcatgtga t gagtgccgg | 60 |
| atccgtaagg tccgatgcag caaggagggt ccaaagtgct cccattgcct c cgatataac | 120 |
| ctaccctgtg aattctccaa caaagttaca cgggtcaacc aaacagcaaa a ttgtaagtg | 180 |
| ataagatggt ctatatttgg gtcaaatacc tgtctttctg actctcagtc a gggcgcgcg | 240 |
| acgtcgagaa gctcgggagt cgggttggag atatcgaaca tgccctccaa c gatgcctgt | 300 |
| cctttattga tgcccatcag ggctttcgtg atctatcaag gccacagtca c aagaaagcg | 360 |
| ggtacacaag ctcaaccagc tcagaagagt gtgaagtaaa cttgtactca g gcaaacaca | 420 |
| cttcacccac cgaggaagat ggattctggc ctctccacgg ttatggctct t ttgtttcac | 480 |
| tcgtcatgga ggcacaggct gctaacgcca acctaacctc ttggttaccg g tcgatatga | 540 |
| ccagcggcca agtcgcagag atggtcgcat ttgaccgcca agctgtgtca g ctgtgcgct | 600 |
| cgaaggtggc tgaggcgaat gaaacgcttc aacagatcat tgaggatatc c aacactat | 660 |
| cggcatccga aaacgatacc tttctcccgt ctcttccacc ccgcgctcta g tggagccgt | 720 |
| ctatcaacga atatttcaag aagctgcatc cacgactccc tatatttagt c gacagacta | 780 |
| ttatggacgc agtggaatct cagtacacaa tcagaactgg gcctccggac c tggtttgga | 840 |
| ttacctcttt caactgcatt gtgcttcagg ccctgactca acatcaattg cgaacaaag | 900 |

```
tcgtgggatg cacaggacaa gacataccaa tagattatat gatcataagc c tgctgcgta      960
atatcaggca gtgctataat cgattggaaa ctcttgttaa accccggcta t cgaatatac     1020
gggccctctt ttgtttggtg cgtcttacaa ccctaccttt ggaacgtggc c tgactttat     1080
tatactaagg cacttgtggc aatggagtat tttgatttcg caattttttct g actatcttt    1140
gctcaagtct gcgagttgtc caggctcatt ggactccatt taacgacaac g accccgcca     1200
acggaagatg gggctgtggg cgaccagcct aaagacttgt tctggagcat c ttcctcgtc     1260
gatgttcgtc aaaaacttgc ttcgttttct gagcatttcg cttactatag g atttagaag    1320
cacgtatcca tcattggggg caaggcctgc ctattgccct cgtatgactg c agcgtacca    1380
ttgcctccat atgactccgc tgcgccacta ccaaatgctt tgcggcacg c atacgcttg     1440
gcattcattc ttgaggagat atatctgggc ttatactcag caaaatccag c aaaatggaa    1500
cagagtcgcg tccgccgccg tatccgcaga attgctcgaa aacttagcca g tggcacgtg    1560
caacatgagc atgtactgcg taccggagat ccgaataggc ctctcgaaga g tatatctgt    1620
gcaacgcagt tgaggtttgc actctcgagc tgttgggtac ttctgcataa a cgcatttgg    1680
agccaggaaa ggggcgctgt ctgcctacaa cacgctcggg attgtctgat g ctgttcaag    1740
caattgtgcg atgggtgtaa atctggtttc agcaatttcg acaggtaagt c ttccgtgcg    1800
accctcttga cagcatccta acctggggat gtacttcata gcattgtcct g aactattct    1860
ttgatctcat tcatgggaat ctatgtccac attgtgagg aagaccagcc g atccattca    1920
caggacatgg agatactcac tttcttcgcc atatacacga accgttcggc a tccaatagg    1980
tcatctgcat ctatctcgta caaattaagc caagtggcca gtcgctgtag c gatattgcc    2040
ctcctcctcc agaatttaag ggagaggcgt tttattccga caacgatatc a cgaagtcca    2100
acgccctcat ggaacgagcc aacctacatg gattacgatg tcgccaatgc g tccactagc    2160
acaactagca ccggctcttc atataacttg aatatcagcc cgcttggtgt a cccggagac    2220
ggccaggtct gggacatata cttcaacccg agagaaatac caatggatgg t acaattgcg    2280
actccttctg aggatgcaac ccaggatttg ctgagcaatg atgctggcca a tgccttggt    2340
ttccccgact tttcacttgg cattgacaac ttctccgact ttccacttgg c attgacatg    2400
actagccaaa gcgaatttgg tcttattatg gaggaggaca taattcgata t gagagacta    2460
ctagataggc ccgtttag                                                    2478
```

<210> SEQ ID NO 32
<211> LENGTH: 1302
<212> TYPE: DNA
<213> ORGANISM: Aspergillus terreus

<400> SEQUENCE: 32

```
atggagtcta aagtccagac aaatgttcca ttaccaaagg cacccttac c caaaaagcc       60
cgtgggaagc gtgtatgtgt tccttcttgg tcgcgcgtgt gccatgttac t gacaatgtc     120
ttctcttaat atatgtatag acgaaaggca ttcctgcatt ggtcgcgggt g cttgtgctg    180
gggcagttga atctccatc acctaccctt tcgaatgtga gcttatcctg t gtttaagag     240
ttccgcttta ccgtggccgc caactgacag tctattgctt ccgctggtag c ggctaaaac    300
tcgcgcccag cttaagcgga gaaaccatga tgtggcagct ataaaacctg g aatccgagg    360
ctggtatgct gggtatggag ccaccttggt aggaaccaca ttgaaagcct c cgttcgtat    420
gtagcgatcc cccttataag cccgcgtgga gcgaaaagga atgaccgttt g caataacaa    480
```

-continued

| | |
|---|---|
| acagaatttg cctccttcaa tatttatcgc tcggccctct cgggcccaaa t ggagagctc | 540 |
| tcaactggag cttccgtcct ggctgggttt ggggctggcg tgaccgaggc t gtcttagcc | 600 |
| gtaacccag cggaggcgat caagacgaaa atgtaagttg caacatctca c ccgttatcc | 660 |
| gatcagttct taattcgttc tcttagcatt gatgcaagga aggttggaaa t gcagagtta | 720 |
| agtacgactt tcgcgcgat agctggaatc cttcgagatc ggggaccgct t ggattcttc | 780 |
| tctgcggttg gtcctacaat tttgcggcag tcgtccaatg cggcagtgaa g ttcactgtt | 840 |
| tataacgaac ttattgggct ggcccgaaaa tactcgaaga acggcgaaga c gtgcaccct | 900 |
| ctggcaagca ccttggtcgg ttctgttact ggagtttgtt gcgcctggtc g acacagcca | 960 |
| ctggacgtga tcaagacgcg gtaagtgctg ctcagatcga cagtaacccg c ccagataag | 1020 |
| tatatgctga cttggatgcg acttcggggtt accagaatgc aatctcttca g gcaagacaa | 1080 |
| ctgtacggaa ataccttaa ctgcgtgaaa acacttctgc gcaatgaagg c attggggtt | 1140 |
| ttctggtccg gcgtctggtt tcggacaggg agactttccc ttacctcggc c atcatgttt | 1200 |
| cccgtgtaag tttaggagta atctacaggc atgatattct tgtacactga c agagcgtca | 1260 |
| aggtacgaga aagtctacaa gttcttgacg cagccaaact ga | 1302 |

<210> SEQ ID NO 33
<211> LENGTH: 1529
<212> TYPE: DNA
<213> ORGANISM: Aspergillus terreus

<400> SEQUENCE: 33

| | |
|---|---|
| atgaccaagc aatctgcgga cagcaacgca aagtcaggag ttacggccga a atatgccat | 60 |
| tgggcatcca acctggccac tgacgacatc cctccggacg tattagaaag a gcaaaatac | 120 |
| cttattctcg atggtattgc atgtgcctgg gttggtgcaa gagtgccttg g tcagagaag | 180 |
| tatgtgcagg caacaatgag ctttgagccg ccagggggcct gcagggtgat t ggatatgga | 240 |
| caagttagtt ctatccaatc tgaacagtct acaaagtata ctgacgatcc t ttgtataga | 300 |
| aactgggggcc tgttgcagca gccatgacca attctgcttt catacaggct a cggagcttg | 360 |
| acgactacca cagcgaagcc ccctacact ctgcaagcat tgtcctccct g cggtctttg | 420 |
| cagcaagtga ggtcttagcc gagcagggca aaacaatttc tggtatagct g tcattctag | 480 |
| ccgccattgt ggggtttgaa tctggcccgc ggatcggcaa agcaatctac g gatcggacc | 540 |
| tcttgaacaa cggctggcat tgtggagccg tgtatggtgc tccagccggt g cgctggcca | 600 |
| caggaaagct ccttggtctg actccagact ccatggaaga tgctctcgga a tcgcgtgca | 660 |
| cgcaagcctg tggcttaatg tcggcgcaat acggaggcat ggtcaagcgc g tgcaacatg | 720 |
| gattcgcagc gcgtaatggt cttcttgggg gactgttggc ccatggtggg t acgaggcca | 780 |
| tgaagggtgt cctggagaga tcttacgcg gtttcctcaa aatgttcacc a aggcaatg | 840 |
| gcagagagcc tccctacaaa gaggaggaag tggtggccgg tctcggttca t tctggcata | 900 |
| cctttactat tcgcatcaag ctctatgcct gctgcggact tgtccatggt c cagtcgaag | 960 |
| ctatcgaaaa ccttcagagg aggtaccccg agctcttgaa tagagccaac c tcagcaaca | 1020 |
| ttcgccacgt tcatgtacag cttttcaacag cctcgaacag tcactgtgga t ggataccag | 1080 |
| aggagagacc catcagttca atcgcagggc agatgagtgt cgcatacatc c tcgccgtcc | 1140 |
| agttggtcga ccagcaatgt cttctggccc agttttccga gtttgatgac a cttggaga | 1200 |
| ggccagaagt gtgggatctg ccaggaagg ttactccatc tcatagcgaa g agtttgatc | 1260 |
| aagacggcaa ctgtctcagt gcgggtcgcg tgaggattga gttcaacgat g gctcttctg | 1320 |

| | |
|---|---|
| ttacggaaac tgtcgagaag cctcttggag tcaaagagcc catgccaaac g aacggattc | 1380 |
| ttcacaaata ccgaacccttt gctggtagcg tgacggacga aacccgggtg a aagagattg | 1440 |
| aggatcttgt cctcagcctg acaggctca ccgacattag cccattgctg g agctgctta | 1500 |
| attgtcccgt aaaatcgcca ctggtataa | 1529 |

<210> SEQ ID NO 34
<211> LENGTH: 1704
<212> TYPE: DNA
<213> ORGANISM: Aspergillus terreus

<400> SEQUENCE: 34

| | |
|---|---|
| atgggccgcg gtgacactga gtccccgaac ccagcgacga cctcggaagg t agcggacaa | 60 |
| aacgagccag agaaaaaggg ccgtgatatt ccattatgga gaaatgtgt c attacgttt | 120 |
| gttgttagtt ggatgactct agtcgttact ttctccagta cttgtcttct t cctgccgcc | 180 |
| cctgaaatcg cgaatgaatt tgatatgact gtcgagacta tcaatatctc c aatgctggt | 240 |
| gtcttggttg ccatgggata ttcatccctc atatggggtc ccatgaacaa g ttagtcggc | 300 |
| aggcggacat catacaatct ggccatttca atgctttgtg cgtgctccgc t ggaacggca | 360 |
| gcggcgataa acgagaaaat gttcatagcg ttcagagtat tgagcggctt a accggaacc | 420 |
| tcgttcatgg tctcaggcca aactgttctt gcagatatct ttgagcctgt a cgcatcaca | 480 |
| cgcccttgtc tccccaattg cgaaaactaa tccgttcgtg cgcaggttta c cgtgggacg | 540 |
| gccgtaggtt tcttcatggc cgggactctt tctggccctg caataggtac g taccctgct | 600 |
| gaaagtacta gaactcccaa caggaactga ctgtttgatc aggcccctgc g tggaggggg | 660 |
| tcatcgtcac tttcacgagt tggcgtgtta tcttctggct tcaactaggt a tgagcggac | 720 |
| tggggctcgt gctttccctg ctatttttcc cgaaaatcga aggaacttct g agaaggtct | 780 |
| caacggcgtt taaaccgacc acacttgttt caatcatatc gaaattctcc c caacggatg | 840 |
| tgctcaagca gtgggtgtat ccaaatgtct ttcttgccgt aagtgcctgg g agatatgcc | 900 |
| ctctgcatct actggaaacg aaatgctcat gccgcaaaca aaaggactta t gctgtggcc | 960 |
| tcctggcgat tacgcaatat tcgatcctga cttcagctcg tgctatattc a actcacggt | 1020 |
| ttcatttaac gactgcccta gtatcgggtc tcttctacct cgctccaggt g ccgggttcc | 1080 |
| tgatagggag tctcgtcggc ggtaaacttt cggatcgcac cgttcggaga t acatagtaa | 1140 |
| agcgcggatt ccgtctcct caggatcgac tccacgacgg gctcatcaca t tgtttgccg | 1200 |
| tgctgcctgc gggaacgctc atttacgggt ggacactcca agaggataag g gtgggatgg | 1260 |
| tagtgcccat aatcgcggcg ttcttcgcgg gctgggggct catgggcagt t taactgcc | 1320 |
| tgaacactta cgtggctggt tgttccaca ccctcattaa tttatcccct t tgtgtacat | 1380 |
| gcccacaata atgttgtctc tgaccgcaag tagaagcctt gccacggaac c ggtctgcag | 1440 |
| tcattgcagg aaagtatatg attcaatact ccttttctgc agggagtagt g cgctcgttg | 1500 |
| tgcccgtcat agacgccctc ggagttggat ggacgttcac gctatgtatg g tacctttct | 1560 |
| tcttacctct caatgtacat gctcacagtt gttgcaggtg tggttgcttc g actatagct | 1620 |
| ggattgatca cggcggccat cgcacggtgg gggataaata tgcaaaggtg g gcagaaagg | 1680 |
| gctttcaacc tgcctaccca atag | 1704 |

<210> SEQ ID NO 35
<211> LENGTH: 1704
<212> TYPE: DNA

<213> ORGANISM: Aspergillus terreus

<400> SEQUENCE: 35

| | | | | | |
|---|---|---|---|---|---|
| atgggccgcg | gtgacactga | gtccccgaac | ccagcgacga | cctcggaagg t | agcggacaa    60 |
| aacgagccag | agaaaaaggg | ccgtgatatt | ccattatgga | gaaatgtgt c | attacgttt   120 |
| gttgttagtt | ggatgactct | agtcgttact | ttctccagta | cttgtcttct t | cctgccgcc   180 |
| cctgaaatcg | cgaatgaatt | tgatatgact | gtcgagacta | tcaatatctc c | aatgctggt   240 |
| gtcttggttg | ccatgggata | ttcatccctc | atatggggtc | ccatgaacaa g | ttagtcggc   300 |
| aggcggacat | catacaatct | ggccatttca | atgctttgtg | cgtgctccgc t | ggaacggca   360 |
| gcggcgataa | cgagaaaat | gttcatagcg | ttcagagtat | tgagcggctt a | accggaacc   420 |
| tcgttcatgg | tctcaggcca | aactgttctt | gcagatatct | ttgagcctgt a | cgcatcaca   480 |
| cgccttgtc | tccccaattg | cgaaaactaa | tccgttcgtg | cgcaggttta c | cgtgggacg   540 |
| gccgtaggtt | tcttcatggc | cgggactctt | tctggccctg | caataggtac g | taccctgct   600 |
| gaaagtacta | gaactcccaa | caggaactga | ctgtttgatc | aggcccctgc g | tgggagggg   660 |
| tcatcgtcac | tttcacgagt | tggcgtgtta | tcttctggct | tcaactaggt a | tgagcggac   720 |
| tggggctcgt | gctttccctg | ctattttcc | cgaaaatcga | aggaacttct g | agaaggtct   780 |
| caacggcgtt | taaaccgacc | acacttgttt | caatcatatc | gaaattctcc c | aacggatg   840 |
| tgctcaagca | gtgggtgtat | ccaaatgtct | ttcttgccgt | aagtgcctgg g | agatatgcc   900 |
| ctctgcatct | actggaaacg | aaatgctcat | gccgcaaaca | aaaggactta t | gctgtggcc   960 |
| tcctggcgat | tacgcaatat | tcgatcctga | cttcagctcg | tgctatattc a | actcacggt  1020 |
| ttcatttaac | gactgcccta | gtatcgggtc | tcttctacct | cgctccaggt g | ccgggttcc  1080 |
| tgatagggag | tctcgtcggc | ggtaaacttt | cggatcgcac | cgttcggaga t | acatagtaa  1140 |
| agcgcggatt | ccgtctccct | caggatcgac | tccacagcgg | gctcatcaca t | tgtttgccg  1200 |
| tgctgcctgc | gggaacgctc | atttacgggt | ggacactcca | agaggataag g | gtgggatgg  1260 |
| tagtgcccat | aatcgcggcg | ttcttcgcgg | gctgggggct | catgggcagt t | ttaactgcc  1320 |
| tgaacactta | cgtggctggt | ttgttccaca | ccctcattaa | tttatcccct t | tgtgtacat  1380 |
| gcccacaata | atgttgtctc | tgaccgcaag | tagaagcctt | gccacggaac c | ggtctgcag  1440 |
| tcattgcagg | aaagtatatg | attcaatact | ccttttctgc | agggagtagt g | cgctcgttg  1500 |
| tgcccgtcat | agacgccctc | ggagttggat | ggacgttcac | gctatgtatg g | tacctttct  1560 |
| tcttacctct | caatgtacat | gctcacagtt | gttgcaggtg | tggttgcttc g | actatagct  1620 |
| ggattgatca | cggcggccat | cgcacggtgg | gggataaata | tgcaaaggtg g | gcagaaagg  1680 |
| gctttcaacc | tgcctaccca | atag | | | 1704 |

<210> SEQ ID NO 36
<211> LENGTH: 1503
<212> TYPE: DNA
<213> ORGANISM: Aspergillus terreus

<400> SEQUENCE: 36

| | | | | | |
|---|---|---|---|---|---|
| atgaagcccg | caatccttat | gaaatactgg | ctcttcgtct | cagctgtgag c | gcgtcaacc    60 |
| ctgaacggca | agctcacatt | gagtgagaca | aaggtgacgg | gggccgttca g | ctggcttgt   120 |
| accaatagtc | caccggacat | ctatatcgac | cccgatgatt | cggtctcagt g | gttcgcgca   180 |
| gcccacgatc | tggccctgga | ctttgggcgc | gtctttggta | aaaatgccac a | gttcgcttc   240 |
| actaacgaga | ctcatccaac | atcgatggcc | atcatcgctg | gtaccataga t | aagtcaacc   300 |

-continued

```
ttccttcaga ggttgatagc ggatcataag ctcgacgtta ccagcatccg t ggccagtgg    360 gaatcctatt catcagcact ggtgttgggt ccagccaaag gcatacagaa t gcgctagtc    420 atagctggca gtgaccgtcg tggggccatc tatggcttat acgatatatc t gaacaaatt    480 ggcgtctcgc cattgttctg gtggacggat gttacccaa ccaaacttga t gccatctac    540 gcgctagatg ttcagaaagt ccagggtcca ccgtcagtga agtatcgtgg a atttttatc    600 aacgacgaag cgcccgcctt gcataactgg attcttgcaa attatggcga g gttgagaac    660 ggggaccctg ccttcatctc acgtttctac gcccatgtct tcgagctgat c ctgcgcctg    720 aaagggaatt acctctggcc ggcgatgtgg tcaaatatgt tttatgttga t gacaccaac    780 aatggcccac tagcggacta ctacggagtg gtaatgggca ctagccacac t ggtatgacg    840 gttgggactc cctgcttgaa agcccatgct gactacgaaa aagaaccgat g gctcgagca    900 acaaacgagc aatcccagtt tctaaacggg acgtgggact ggattagcaa c gaggtcaat    960 gttaaagcat ttatgaggga gggtgtaatt aggagccaac actgggagac c gcatacaca   1020 atgggcatgc ggggtctagg cgatgctgca tcgccgacac ttaacgcaac a gtggaagaa   1080 agcattgtta gctggcagga atccgtgcta tcggacatcc tgaataaaac c aacctgtcg   1140 aacgtggttc aaccatttgt cctatttgat gttaggatcc attcaccctc a aatatatcg   1200 tttgctgact gccaggtctg tgacacagga actgggaact tactatgaga g cggcatgac   1260 tgtaccagac caggtcacat tgatatatcc tgatgacaat gcaggcaata t gctgcgtct   1320 cccattgcag aatgaaactg ggcgttctgg gggcgcagga atttactatc a ttttgacat   1380 gaacgcgccg ccgcgctgtt acaagtggat caacacagct caactgatca g gacctggga   1440 tcaactgcgc gcggcataca gccacggtgc tcagacagta tgggttgcca a tattgggga   1500 tat                                                                  1503
```